United States Patent [19]

Dehnert et al.

[11] 4,042,578

[45] * Aug. 16, 1977

[54] AZO DYES HAVING 2,6-DIAMINOPYRIDINE DERIVATIVES AS COUPLING COMPONENTS

[75] Inventors: Johannes Dehnert; Gunther Lamm, both of Ludwigshafen, Germany

[73] Assignee: Badische Anilin- & Soda-Fabrik Aktiengesellschaft, Ludwigshafen (Rhine), Germany

[ * ] Notice: The portion of the term of this patent subsequent to Dec. 21, 1993, has been disclaimed.

[21] Appl. No.: 338,859

[22] Filed: Mar. 7, 1973

[30] Foreign Application Priority Data

| | | |
|---|---|---|
| Mar. 10, 1972 | Germany | 2211663 |
| June 2, 1972 | Germany | 2226933 |
| Oct. 21, 1972 | Germany | 2251702 |
| Dec. 2, 1972 | Germany | 2259103 |
| Dec. 1, 1972 | Germany | 2258823 |
| Dec. 6, 1972 | Germany | 2259684 |

[51] Int. Cl.$^2$ .............................................. C09B 29/36

[52] U.S. Cl. .................................... 260/156; 260/154; 260/294.8 C; 260/294.8 G; 260/294.9; 260/295 R; 260/295 CA

[58] Field of Search .......................................... 260/156

[56] References Cited

U.S. PATENT DOCUMENTS

| | | | |
|---|---|---|---|
| 2,068,353 | 1/1937 | Schneiderwirth | 260/156 |
| 2,145,579 | 1/1939 | Binz et al. | 260/156 |
| 2,148,705 | 2/1939 | Mietzsch et al. | 260/156 |
| 2,681,906 | 6/1954 | Granatek | 260/156 |
| 3,531,457 | 9/1970 | Ackermann et al. | 260/154 |
| 3,531,458 | 9/1970 | Ackermann et al. | 260/154 |

FOREIGN PATENT DOCUMENTS

| | | | |
|---|---|---|---|
| 270,987 | 12/1950 | Cuba | 260/156 |
| 2,062,717 | 6/1972 | Germany | 260/156 |

*Primary Examiner*—Charles F. Warren
*Attorney, Agent, or Firm*—Keil, Thompson & Shurtleff

[57] ABSTRACT

Azo dyes having 2,6-diaminopyridine derivatives as coupling components which preferably bear cyano or carbamoyl as substituents in the 3-position. The dyes give brilliant yellow to blue colorations, particularly on synthetic polyesters, which are distinguished by outstanding fastness properties.

8 Claims, No Drawings

AZO DYES HAVING 2,6-DIAMINOPYRIDINE DERIVATIVES AS COUPLING COMPONENTS

The invention relates to dyes of the formula (I):

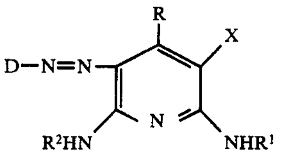

(I)

in which

D is the radical of a diazo component;

R is unsubstituted or substituted alkyl or unsubstituted or substituted phenyl;

X is hydrogen, cyano or unsubstituted or substituted carbamoyl;

$R^1$ is a radical of the formula: $C_6H_5$;

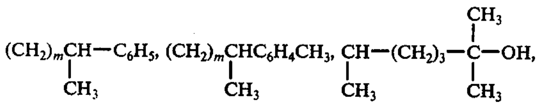

$(CH_2)_3OCH_2CH_2OH$ $(CH_2)_3O(CH_2)_6OH$,

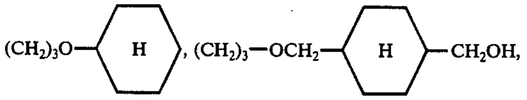

$(CH_2)_3OC_2H_4OR^7$, $(CH_2)_3(OC_2H_4)_qOR^8$, $(CH_2)_3OR^9$,

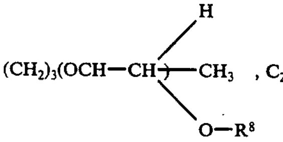

, $C_2H_4OC_6H_5$, $C_2H_4OC_6H_4CH_3$,

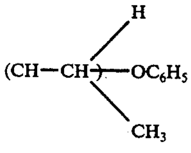

or

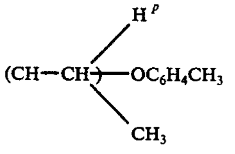

or the radical containing hydroxyl groups of the formula:

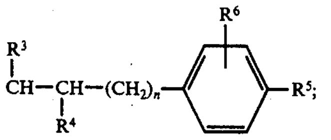

$R^2$ is hydrogen, $R^1$ or an unsubstituted or substituted aliphatic, cycloaliphatic, araliphatic or aryl radical;

$R^3$ is alkyl of one to three carbon atoms or hydroxyalkyl;

$R^4$ is hydrogen, alkyl of one to three carbon atoms or hydroxyalkyl;

$R^5$ is hydrogen or hydroxy;

$R^6$ is hydrogen, alkyl of one to four carbon atoms, methoxy, ethoxy or chloro;

$R^7$ is ethyl, propyl, butyl, cyclohexyl, benzyl, phenylethyl or methylphenyl;

$R^8$ is hydrogen, alkyl of one to four carbon atoms, cyclohexyl, phenyl, methylphenyl, benzyl or phenylethyl;

$R^9$ is cyclohexyl, phenyl, methylphenyl, benzyl or phenylethyl;

$m$ is 1 or 2;

$n$ is zero, 1 or 2;

$q$ is 2, 3 or 4; and $p$ is 1, 2, 3 or 4.

The radicals (D) of the diazo components may be derived for example from amines of the benzene, naphthalene, diphenyl, benzothiazole, benzoisothiazole, thiazole, thiadiazole, thiophene, triazole, benzotriazole, indazole, pyrazole, azobenzene or anthraquinone series.

The following are examples of substituents for the radical (D) of the diazo components: in the benzene series: chloro, bromo, nitro, cyano, trifluoromethyl, methylsulfonyl, ethylsulfonyl, phenylsulfonyl, p-(β-hydroxyethyl)-phenylsulfonyl, carbomethoxy, carboethoxy, carbobutoxy, carbo-β-methoxyethoxy, carbo-β-ethylhexoxy, carbo-β-hydroxyethoxy, carbamoyl, N-substituted carbamoyl, N-disubstituted carbamoyl, N-substituted sulfamoyl, N-disubstituted sulfamoyl, methyl, ethyl, methoxy and ethoxy;

Examples of N-substituents of carbamoyl or sulfamoyl are methyl, ethyl, propyl, butyl, β-ethylhexyl, cyclohexyl, benzyl, phenylethyl, β-hydroxyethyl, β-hydroxypropyl, β-methoxyethyl, γ-methoxypropyl, γ-ethoxypropyl, pyrrolidide, piperidide and morpholide.

In the azobenzene series; chloro, bromo, nitro, cyano, carbomethoxy, carboethoxy, methyl, ethyl, methoxy, ethoxy, hydroxy, acetylamino, formyl, β-hydroxyethoxy and ethoxycarbonylamino.

In the heterocyclic series; chloro, bromo, nitro, cyano, methyl, ethyl, phenyl, methoxy, ethoxy, methylmercapto, β-carbomethoxyethylmercapto, β-carboethoxyethylmercapto, carbomethoxy, carboethoxy, acetyl, methylsulfonyl and ethylsulfonyl.

The radical D may be derived for example from the following amines: aniline, o-toluidine, m-toluidine, p-toluidine, o-nitroaniline, m-nitroaniline, p-nitroaniline, o-cyanoaniline, m-cyanoaniline, p-cyanoaniline, 2,4-dicyanoaniline, o-chloroaniline, m-chloroaniline, p-chloroaniline, 3,4-dichloroaniline, 2,5-dichloroaniline, 2,4,5-trichloroaniline, 2,4,6-trichloroaniline, o-bromoaniline, m-bromoaniline, p-bromoaniline, 2,4,6-tribromoaniline, 2-chloro-4-nitroaniline, 2-bromo-4-nitroaniline, 2-cyano-4-nitroaniline, 2-methylsulfonyl-4-nitroaniline, 2-methyl-4-nitroaniline, 2-methoxy-4-nitroaniline, 4-chloro-2-nitroaniline, 4-methyl-2-nitroaniline, 4-methoxy-2-nitroaniline, 1-amino-2-trifluoromethyl-4-chlorobenzene, 2-chloro-5-aminobenzonitrile, 2-amino-5-chlorobenzonitrile, 1-amino-2-nitrobenzene-4-sulfonic acid n-butylamide, 1-amino-2-nitrobenzene-4-sulfonic acid β-methoxyethylamide, 2,4-dinitroaniline, 2,4-dinitro-6-chloroaniline, 2,4-dinitro-6-bromoaniline, 2,4-dinitro-6-cyanoaniline, 1-amino-2,4-dinitrobenzene-6-methylsulfone, 2,6-dichloro-4-nitroaniline, 2,6-dibromo-4-nitroaniline, 2-chloro-6-bromo-4-nitroaniline, 2,6-dicyano-4-nitroaniline, 2-cyano-4-nitro-6-chloroaniline, 2-cyano-4-nitro-6-bromoaniline, 1-aminobenzene-4-methylsulfone, 1-amino-2,6-dibromobenzene-4-methylsulfone, 1-amino-2,6-dichlorobenzene-4-methylsulfone, 1-amino-2,6-dinitrobenzene-6-carboxylic methyl ester or β-methoxyethyl ester, propyl 3,5-dichloroanthranilate, β-methoxyethyl 3,5-dibromoanthranilate, N-benzoyl-p-phenylenediamine, N-acetyl-p-phenylenediamine, N-phenylsulfonyl-p-phenylenediamine, N-phenylsulfonyl-m-phenylenediamine, 4-aminoacetophenone, 4-aminobenzophenone, 2-aminobenzophenone, 2-aminodiphenylsulfone, methyl 2-aminobenzoate, methyl 3-aminobenzoate, methyl 4-aminobenzoate and the corresponding ethyl, propyl, butyl, isobutyl, β-ethylhexyl, cyclohexyl, benzyl, phenyl, β-methoxyethyl, β-ethoxyethyl, β-butoxyethyl, methyl diglycol, ethyl diglycol, methyl triglycol, ethyl triglycol, β-hydroxyethyl, β-acetoxyethyl, β-(β'-hydroxyethoxy)-ethyl, β-hydroxypropyl, γ-hydroxypropyl, ω-hydroxybutyl, ω-hydroxyhexyl esters, methyl 5-nitroanthranilate and the corresponding isobutyl, methyl diglycol, β-methoxyethyl, β-butoxyethyl and β-acetoxyethyl esters of 5-nitroanthranilic acid, the dimethyl, diethyl, dipropyl or dibutyl ester of 3-aminophthalic acid, 4-aminophthalic acid, 5-aminoisophthalic acid or aminoterephthalic acid, the amide, methylamide, propylamide, butylamide, isobutylamide, cyclohexylamide, 62 -ethylhexylamide, γ-methoxypropylamide, α-ethoxypropuylamide or anilide of 3-aminobenzoic acid or 4-aminobenzoic acid, the dimethylamide, diethylamide, pyrrolidide, morpholide or N-methyl-N-β-hydroxyethylamide of 2-aminobenzoic acid, 3-aminobenzoic acid or 4-aminobenzoic acid, the diamide or bis-γ-methoxypropylamide of 5-aminoisophthalic acid, the bisdiethylamide of aminoterephthalic acid, the imide, β-hydroxyethylimide, γ-hydroxypropylimide, phenylimide or p-tolylimide of 3-aminophthalic acid or 4-aminophthalic acid, the β-hydroxyethylimide of 3-amino-6-nitrophthalic acid, the dimethylamide, diethylamide, pyrrolidide, morpholide or N-methylanilide of 2-aminobenzenesulfonic acid, 3-aminobenzenesulfonic acid or 4-aminobenzenesulfonic acid, 2'-aminophenyl methylsulfonate, 3'-aminophenyl methylsulfonate, 4'-aminophenyl methylsulfonate, 2'-aminophenyl ethylsulfonate, 3'-aminophenyl ethylsulfonate, 4'-aminophenyl ethylsulfonate, 2'-aminophenyl butylsulfonate, 3'-aminophenyl butylsulfonate, 4'-aminophenyl butylsulfonate, 2'-aminophenyl benzenesulfonate, 3'-aminophenyl benzenesulfonate, 4'-aminophenyl benzenesulfonate, the ethylimide, butylimide, β-methoxyethylimide or γ-methoxypropylimide of 4-aminonaphthalic acid, 1-aminonaphthalene, 2-aminonaphthalene, 1-amino-2-ethoxynaphthalene, 2-aminodiphenyl, 4-aminodiphenyl, 1-aminoanthraquinone, 1-amino-4-chloroanthraquinon, 3-aminodiphenylene oxide, 4-aminodiphenylene oxide, 2-aminobenzothiazole, 2-amino-6-methylsulfonylbenzothiazole, 2-amino-6-nitrobenzothiazole, 5,6-dichloro-2-aminobenzothiazole, 6,7-dichloro-2-aminobenzothiazole, 4-amino-5-bromo-7-nitrol-1,2-benzoisothiazole, 3-amino-5-nitro-2,1-benzoisothiazole, 3-amino-5-nitro-7-bromo-2,1-benzoisothiazole, 2-aminothiazole, 2-amino-5-nitrothiazole, 2-amino-b 4-methylthiazole-5-carboxylic ethyl ester, 2-amino-4-methyl-5-acetylthiazole, 2-amino-3-cyano-4-methylthiophene-5-carboxylic esters, 2-phenyl-5-amino-1,3,4-thiadiazole, 3-methylmercapto-5-amino-1,2,4-thiadiazole, 3-β-carbomethoxyethylmercapto-5-amino-1,2,4-thiadiazole, 3-amino-1,2,4-triazole, 4-amino-7-nitrobenzotriazole, 3-aminoindazole, 3-amino-5-chloroindazole, 3-amino-5-nitroindazole, 1-benzyl-5-aminopyrazole and 1-phenyl-5-aminopyrazole.

Examples of suitable diazo components of the aminoazo series are: 2',4-dimethyl-4-aminoazobenzene, 3',2-dimethyl-4-aminoazobenzene, 2,5-dimethyl-4-aminoazobenzene, 2-methyl-5-methoxy-4-aminoazobenzene, 2-methyl-4',5-dimethoxy-4-aminoazobenzene, 4'-chloro-2-methyl-5-methoxy-4-aminoazobenzene, 4'-nitro-2-methyl-5-methoxy-4-aminoazobenzene, 4'-hydroxy-2-methyl-5-methoxy-4-aminoazobenzene, 4'-(β-hydroxyethoxy)-2-methyl-5-methoxy-4-aminoazobenzene, 4'-hydroxy-2,2'-dimethyl-5-methoxy-4-aminoazobenzene, 4'-hydroxy-4-aminoazobenzene, 4'-hydroxy-2'-methyl-4-aminoazobenzene, 4'-hydroxy-3'-methyl-4-aminoazobenzene, 2'-hydroxy-5'-methyl-4-aminoazobenzene, 4'-hydroxy-2-methoxy-4-aminoazobenzene, 4'-hydroxy-2'-chloro-4-aminoazobenzene, 4'-hydroxy-2,5-dimethoxy-4-aminoazobenzene, 4'-hydroxy-2,6-dichloro-4-aminoazobenzene, 4-hydroxy-3-methoxy-4-aminoazobenzene, 4'-chloro-2-methyl-4-aminoazobenzene, 4'-formyl-2-methyl-4-aminoazobenzene, 4'-(ethoxycarbonylamino)-2-methyl-4-aminoazobenzene, 2,5-dimethoxy-4-aminoazobenzene, 4'-chloro-2,5-dimethoxy-4-aminoazobenzene, 4'-nitro-2,5-dimethoxy-4-aminoazobenzene, 4'-(hydroxyethoxy)-2,5-dimethoxy-4-aminoazobenzene, 4'-chloro-2,5-dimethyl-4-aminoazobenzene, 4'-methoxy-2,5-dimethyl-4-aminoazobenzene, 4'-nitro-4-aminoazobenzene, 3,5-dibromo-4-aminoazobenzene, 2,3'-dichloro-4-aminoazobenzene, 3-methoxy-4-aminoazobenzene, 1-phenylazo-4-aminonaphthalene and 2-phenylazo-3-ethoxy-4-aminonaphthalene.

Examples of radicals R are ethyl, n-propyl, isopropyl, butyl, pentyl, α-ethylpentyl, phenyl, methylphenyl and preferably methyl.

Examples of substituted carbamoyl radicals for X are N-methylcarbamoyl, N-ethylcarbamoyl, N-butylcarbamoyl, N-β-hydroxyethylcarbamoyl, N-γ-methoxypropylacarbamoyl, N,N-dimethylcarbamoyl, N,N-diethylcarbamoyl, N,N-dibutylcarbamoyl or N-methyl-N-β-hydroxyethylcarbamoyl. Unsubstituted carbamoyl is preferred because of its easier accessibility.

Examples of individual radicals $R^1$, in addition to those already specified, are: $(CH_2)_3OC_2H_4OC_2H_5$, $(CH_2)_3OC_2H_4—OCH(CH_3)_2$, $(CH_2)_3OC_2H_4OC_4H_9$, $(CH_2)_3OC_2H_4OCH_2C_6H_5$, $(CH_2)_3OC_2H_4OC_2H_4C_6H_5$,

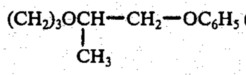

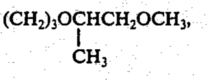

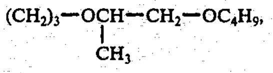

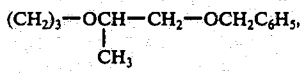

$(CH_2)_3(OC_2H_4)_2OCH_3$,

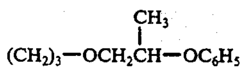

and the corresponding radicals in which the grouping $—OC_2H_4—$,

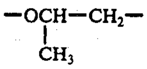 or 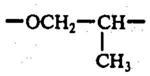

is present twice, thrice or four times, and compounds in which $C_6H_5$ has been replaced by $C_6H_4CH_3$.

Other examples are: $(CH_2)_3OC_6H_5$, $(CH_2)_3OCH_2C_6H_5$, $(CH_2)_3OC_2H_4C_6H_5$, $CH_2CH—OC_6H_5$, $—CH—CH_2—OC_6H_5$ and
$CH_3$ $CH_3$

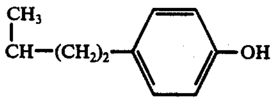

and the radicals having $C_6H_4CH_3$ instead of $C_6H_5$.

Radicals $R^2$ (in addition to being hydrogen or $R^1$) may for example be alkyl of one to eight carbon atoms which may be interrupted by oxygen atoms and may bear hydroxy, alkoxy, acyloxy, carboxy, carboxylic ester, cycloalkoxy, aralkoxy or aroxy as substituents, cycloalkyl of five to eight carbon atoms which may bear hydroxy, chloro, hydroxyalkyl, chloroalkyl or alkyl as substituents, aralkyl of seven to fifteen carbon atoms, phenyl which may bear chloro, hydroxy, alkoxy, alkyl, hydroxyalkyl or hydroxyalkoxy as substituents, and also alkenyl, pyrrolidonyalkyl and carboxyalkyl.

Examples of radicals $R^2$ are: unsubstituted or substituted alkyl radicals: $CH_3$, $C_2H_5$, n- and i-$C_3H_7$, n- and i-$C_4H_9$, $C_6H_{13}$, $CH_2—CH—C_4H_9$
$C_2H_5$ $CH_2CH=CH_2$, $CH_2CH_2OH$, $(CH_2)_3OH$, $CH_2CHOH$, $CH—CH_2OH$,
$CH_3$ $CH_3$ $(CH_2)_4OH$, $(CH_2)_6OH$, $(CH_2)_2O(CH_2)_2OH$, $(CH_2)_3O(CH_2)_4OH$,

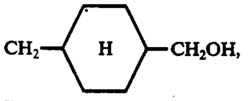

$(CH_2)_3OC_2H_4OCH_3$, $(CH_2)_3OC_2H_4OC_6H_5$, $CH_2CH_2OCH_3$, $CH_2CH_2OC_2H_5$, $CH_2Ch_2OC_3H_7$, $CH_2CH_2OC_4H_9$, $(CH_2)_3OCH_3$, $(CH_2)_3OC_2H_5$, $(CH_2)_3OC_3H_7$, $(CH_2)_3OC_4H_9$, $(CH_2)_3OCH_2CHC_4H_9$,
$C_2H_5$ $(CH_2)_3OC_6H_{13}$, $(CH_2)_3OC_8H_{17}$, $—CHCH_2OCH_3$, $CHCH_2OC_4H_9$, $CHCH_2—OC_6H_5$,
$CH_3$ $CH_3$ $CH_3$ $CHCH_2OCH_2C_6H_5$, $CH_2CHOCH_3$, $CH_2CH—OC_2H_5$,
$CH_3$ $CH_3$ $CH_3$ $CH_2CH—OC_4H_9$, $CH_2CH—OC_2H_4C_6H_5$ and $CH_2CH—OC_6H_5$;
$CH_3$ $CH_3$ $CH_3$ carboxyalkyl and carbalkoxyalkyl radicals of the formulae: $CH_2—COOE$, $CH_2—CH_2—COOE$, $(CH_2)_5—COOE$ or $(CH_2)_2—O—CO—(CH_2)_2—COOE$ where E may be for example hydrogen, methyl, ethyl, propyl, benzyl, β-hydroxyethyl, ω-hydroxyhexyl, δ-hydroxybutyl, β-methoxyethyl, γ-methoxypropyl, γ-ethoxypropyl, β-phenoxyethyl or β-hydroxyethoxyethyl; acyloxyalkyl radicals of the formulae: $CH_2—CH_2—O—$acyl, $(CH_2)_3—O—$acyl, $CH_2—CH—O—$acyl,
$CH_3$ $(CH_2)_6—O—$acyl, $(CH_2)_2—O—(CH_2)_2—O—$acyl or $(CH_2)_3—O—(CH_2)_4—O—$acyl in which acyl is for example $CO—H$, $CO—CH_3$, $CO—C_2H_5$, $CO—CH—(CH_2)_3—CH_3$,
$C_2H_5$ $CO—CH_2Cl$, $CO—CH_2—CO—CH_3$, $CO—CH=CH_2$,

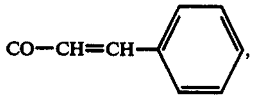, $CO—CH=CH—COOH$, $CO—(CH_2)_2—COOH$, $CO—(CH_2)_2—COOC_2H_5$,

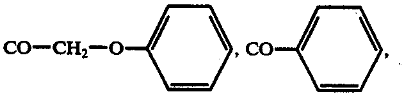,

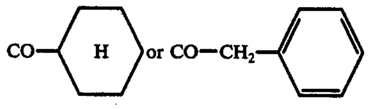

and the radicals $R^1$ containing a hydroxyl group may similarly be esterified with acyl.

Acyl radicals also include COOV and CONHB in which B may be for example alkyl or aryl. Examples are $COOCH_3$, $COOC_2H_5$, $COOC_4H_9$, $CONCH_3$, $CONHC_4H_9$, $CONHC_6H_5$, $CONHC_6H_4Cl$ and $CONHC_6H_3Cl_2$; pyrrolidonylalkyl radicals of the formulae:

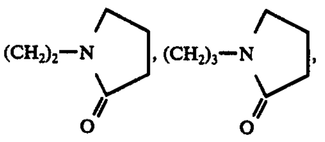,

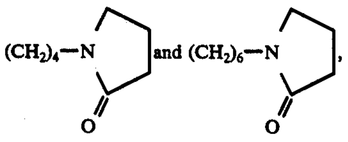, cycloalkyl radicals of the formulae:

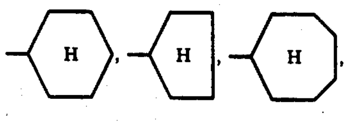,

-continued

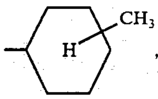,
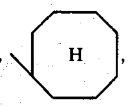,
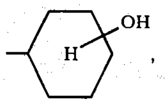,

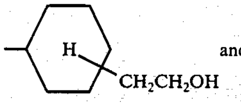
and
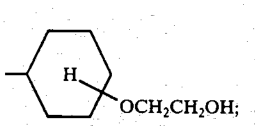

aralkyl radicals of the formulae: $CH_2—C_6H_5$, $C_2H_4—C_6H_5$,

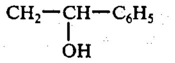

and with $C_6H_4—CH_3$ instead of $C_6H_5$ and the radicals of the formulae:

$C_6H_4Cl$, $C_6H_3Cl_2$, $C_6Cl_4CH_3$, $C_6H_3(CH_3)_2$, $C_6H_4CN$, $C_6H_4OH$, $C_6H_4OCH_2CH_2OH$, $C_6H_4OCH_3$, $C_6H_4OC_2H_5$ and $C_6H_4NHCOCH_3$.

Dyes of the formula (I) may be produced by reacting a diazo compound of an amine of the formula (II):

$$D—NH_2 \qquad (II)$$

with a coupling component of the formula (III):

(III)

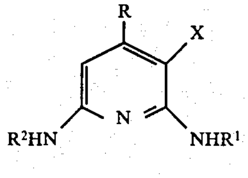

in which D, R, X, $R^1$ and $R^2$ have the meanings given above.

Diazotization of the amines is carried out conventionally. Coupling is also carried out conventionally in aqueous medium with or without the addition of solvents at a weakly to strongly acid pH.

Production of the coupling components of the formula (III) is described in principle in German Patent Specification No. 2,062,717 and the statements therein may be applied in the present case.

If the dye of formula (I) of the invention contains an ester group in the radical $R^1$ and/or $R^2$ the compounds of formula (I) may in principle be prepared by the said process if the appropriate ester group is already contained in the coupling component. In some cases however it is convenient to introduce the acid radical (acyl) into the finished dye of formula (I). The free acids, their anhydrides, chlorides or esters are suitable for this and conveniently an inert diluent or solvent is added such as monochlorobenzene, dichlorobenzene or trichlorobenzene, tetrahydrofuran, dioxane, dimethylformamide, N-methylpyrrolidone or pyridine.

In esterification with the free acid it may be advantageous to add an inorganic or organic catalyst, for example hydrogen chloride gas or p-toluenesulfonic acid and to allow the water formed to escape by evaporation from the reaction mixture. When an acid anhydride or chloride is used for esterification, the acid itself may in special cases be used as the solvent. Thus reaction with acetic anhydride may be carried out in glacial acetic acid. When using an acid chloride as the esterifying agent it is advantageous to add an acid-binding agent, for example sodium carbonate, sodium acetate, magnesium oxide or pyridine to the reaction mixture. The following are specific examples of esterifying agents: formic acid, acetic acid, chloroacetic acid and the esters, anhydrides and chlorides of these acids, also chloroformates, diketene or isocyanates. Conversion of the carboxyl group into the carboxylic ester group may similarly be carried out in the finished dye by conventional methods known from the literature.

Particular industrial value attaches to dyes and mixtures of dyes of the formula (Ia):

(Ia)

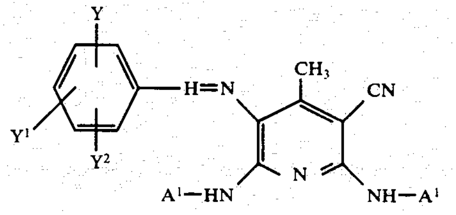

in which

Y is nitro, cyano, chloro, bromo, carbomethoxy, carboethoxy, β-methoxycarboethoxy, methylsulfonyl, ethylsulfonyl, methyl, methoxy or phenylazo;

$Y^1$ is hydrogen, nitro, chloro, bromo, cyano, methyl, methoxy, carbomethoxy, carboethoxy, methylsulfonyl or ethylsulfonyl;

$Y^2$ is hydrogen, chloro, bromo, cyano, methyl, methoxy, carbomethoxy or carboxethoxy;

one $A^1$ may be a radical of the formula $R^1$ and the other $A^1$ may be hydrogen or a radical containing a hydroxyl or alkoxy group and the hydroxyl group may be esterified by formyl or acetyl.

Preferred radicals $R^1$ are for example: $C_6H_5$,

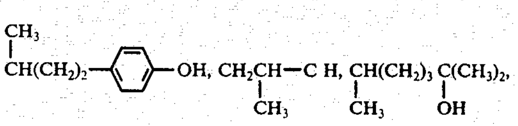

$(CH_2)_3—OC_2H_4OH$, $(CH_2)_3O(CH_2)_6OH$,

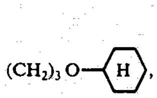, $(CH_2)_3OC_2H_4OC_6H_5$,

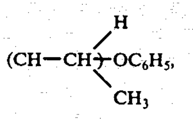

$(CH_2)_3OC_2H_4OCH_2C_6H_5$, $(CH_2)_3(OC_2H_4)_2OR^8$,

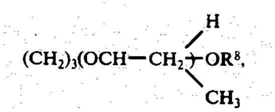

$(CH_2)_3OC_6H_5$, $(CH_2)_3OCH_2C_6H_5$ and $(CH_2)_3OC_2H_4C_6H_5$, $R_8$ having the meanings given above.

Examples of other preferred radicals $A^1$ are hydrogen, ω-hydroxybutyl, ω-hydroxyhexyl, β-hydroxyethyl, β-hydroxypropyl and radicals of the formulae: $C_2H_4OCH_3$, $C_3H_6OCH_3$, $CH_2CH_2OCHO$, $CH_2CH_2CH_2OCHO$, $CH_2—CH_2—OCOCH_3$, $(CH_2)_3O(CH_2)_4OH$, $(CH_2)_2O(CH_2)_2OH$,

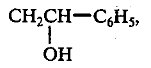

$(CH_2)_3OR^{10}$, $(CH_2)_3OC_2H_4OCH_3$ and $(CH_2)_3OC_2H_4OC_6H_5$, $R^{10}$ being hydrogen or alkyl of one to four carbon atoms. Preferred examples of acyl radicals are CHO, $COCH_3$ and $COC_2H_5$. Moreover the following are preferred:

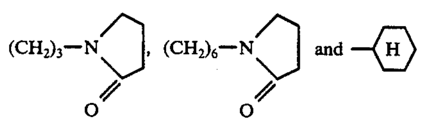

Another group of preferred dyes has the formula:

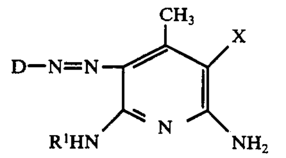

in which D, $R^1$ and X have the meanings given above.

The radicals $R^1$ and $R^2$ are advantageously chosen so that they contain at least one hydrogen atom or one or more oxygen atoms and the total number of carbon atoms is in the range from five to twenty, preferably from five to sixteen.

Those dyes are also particularly valuable which contain as dizao components benzothiazole, benzoisothiazole, thiazole, thidadiazole or thiophene which may bear nitro, chloro, bromo, cyano, methyl, methylmercapto, β-carbomethoxyethylmercapto, β-carboethoxyethylmercapto, carbomethoxy, carboethoxy, carboglycol ester or acetyl as substituents.

The following examples are given from among the particularly preferred diazo components: 4-nitroaniline, 2-chloro-4-nitroaniline, 2-bromo-4-nitroaniline, 2-cyano-4-nitronailine, 2-methoxy-4-nitroaniline, 2-amino-5-nitrophenylsulfonic acid dimethylamide, 2-amino-5-nitrophenylsulfonic acid butylamide, 2-amino-5-nitrophenylsulfonic acid β-methoxyethylamide, 2-aminobenzonitrile, 3-chloro-4-aminobenzonitrile, 2-chloro-5-aminobenzonitrile, 2-amino-5-chlorobenzonitrile, 2,5-dichloro-4-aminobenzonitrile, 1-amino-2,4-dicyanobenzene, 1-amino-2,4-dicyano-6-chlorobenzene, 2-chloro-4-amino-5-nitrobenzonitrile, 2-amino-3-chloro-5-nitrobenzonitrile, 1-amino-3-bromo-5-nitrobenzonitrile, 2,6-dicyano-4-nitroaniline, 2,5-dichloro-4-nitroaniline, 2,6-dichloro-4-nitroaniline, 2,6-dibromo-4-nitroaniline, 2-chloro-6-bromo-4-nitroaniline, 2,4-dinitroaniline, 2,4-dinitro-6-chloroaniline, 2,4-dinitro-6-bromoaniline, 2-amino-3,5-dinitrobenzonitrile, 1-amino-4-nitrobenzene-2-methylsulfone, 1-amino-4-nitrobenzene-2-ethylsulfone, 4-methylsulfonylaniline, 1-amino-2-chlorobenzene-4-methylsulfone, 1-amino-2,6-dibromobenzene-4-methylsulfone, 1-amino-2,6-dichlorobenzene-4-methylsulfone, 2-aminobenzoic acid esters, 4-aminobenzoic acid esters, 2-amino-5-nitrobenzoic acid esters, 2-amino-3-chloro-5-nitrobenzoic acid esters, 2-amino-3,5-dichlorobenzoic acid esters, 2-amino-3,5-dibromobenzoic acid esters, methyl 2-amino-3,5-dinitrobenzoate, β-methoxyethyl 2-amino-3,5-dinitrobenzoate, diethyl-2-aminoterephthalate, 4-aminoazobenzene, 2,3'-dimethyl-4-aminoazobenzene, 2',3-dimethyl-4-aminoazobenzene, 2,5-dimethyl-4-aminoazobenzene and 3,5-dibromo-4-aminoazobenzene.

The following are paricularly valuable heterocyclic diazo components: 2-amino-5-nitrothiazole, 2-amino-4-methyl-5-nitrothiazole, 2-amino-4-methylthiazole-5-carboxylic acid ethyl ester, 2-amino-5-phenyl-1,3,4-thiadiazole, 3-phenyl-5-amino-1,2,4-thiadiazole, 3-methylmercapto-5-amino-1,2,4-thiadiazole, 3-β-carbomethoxyethylmercapto-5-amino-1,2,4-thiadiazole, 3-β-carboethoxyethylamercapto-5-amino-1,2,4-thiadiazole, 2-amino-6-cyanobenzothiazole, 2-amino-6-carboxylic methyl ester benzothiazole, 2-amino-6-nitrobenzothiazole, 2-amino-3-cyano-4-methylthiophene-5-carboxylic esters, 3-amino-5-nitro-2,1-benzoisothiazole, 3-amino-5-nitro-7-chloro-2,1-benzoisothiazole, 3-amino-5-nitro-7-bromo-2,1-benzoisothiazole, 4-amino-7-nitro-1,2-benzoisothiazole, 4-amino-5-bromo-1,2-benzoisothiazole, 4-amino-5-bromo-7-nitro-1,2-benzoisothiazole, 4-amino-5-cyano-7-nitro-1,2-benzoisothiazole and 4-amino-5-chloro-7-nitro-1,2-benzoisothiazole.

The new dyes are yellow to blue and are suitable for coloring textile materials of acrylonitrile polymers, synthetic polyamides, cellulose esters such as secondary cellulose acetate or cellulose triacetate, and particularly linear polyesters such as polyethylene glycol terephthalate or polymers having a similar chemical constitution. Deep colorations are obtained which are distinguished by outstanding fastness properties.

The following Examples illustrate the invention. Parts and percentages are by weight unless otherwise stated.

EXAMPLE 1

A mixture of 187 parts of 2,6-dichloro-3-cyano-4-methylpyridine, 200 parts of isopropanol and 300 parts of aniline is stirred for eight hours at about 90° C to 100° C. The mixture is allowed to cool and poured while stirring into about 1500 parts of water, 200 parts of concentrated hydrochloric acid and 200 parts of ice. Stirring is continued for another hour and the deposited precipitate which probably has the formula:

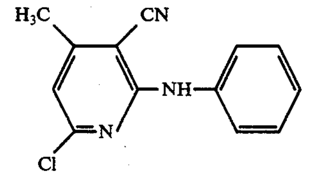

is suction filtered, washed with water until neutral and dried. About 240 parts of a colorless powder is obtained which melts at 135° to 140° C.

12.2 parts of this powder is stirred with 40 parts of γ-hydroxypropylamine for six hours at 245° to 160° C. The mixture is then allowed to cool and after 100 parts of water has been added it is acidified with hydrochloric acid to a pH of from about 0 to 1. If necessary a little glacial acetic acid or dimethylformamide is added and a solution of the coupling component of the probable formula:

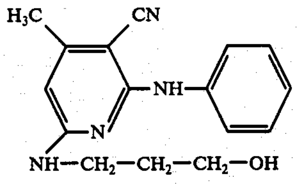

is obtained. A solution or suspension of this coupling component is cooled to 0° to 3° C by adding ice and a diazonium salt soultion is added which is obtained as follows: 6.9 parts of p-nitroaniline has added to it about 30 parts of concentrated hydrochloric acid (30%) and 80 parts of water, the mixture is cooled to 0° C and 15 parts by volume of 23% sodium nitrite solution is added in portions. The whole is stirred for another two hours, any excess of nitrous acid present is removed in the usual way and the product is filtered.

The filtrate is added to the coupling mixture and then such an amount of sodium acetate or caustic soda solution is added gradually while stirring until the pH of the coupling mixture is from about 2 to 3. Ice-water may be added to the mixture if it is difficult to stir. After coupling is over the mixture is heated to 70° to 80° C, filtered, washed with water and dried. About 20 parts of a reddish brown powder is obtained of the probable formula:

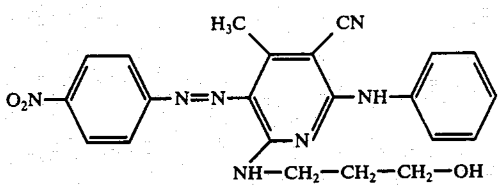

which dissolves in dimethylformamide with a red color and dyes polyethylene terephthalate cloth full, clear yellowish red shades having outstanding fastness properties.

The following dyes characterized by the diazo and coupling components may be obtained in an analogous manner.

TABLE 1

Coupling component:

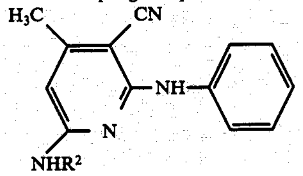

| Example No. | Diazo component | $R^2$ | Shade |
|---|---|---|---|
| 2 | 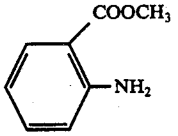 | $-CH_2-CH_2-CH_2-O-CH_3$ | reddish yellow |
| 3 | | $-CH_2-CH_2-OH$ | yellow |
| 4 | | $-CH_2-C_2-CH_2-OH$ | reddish yellow |
| 5 | | $-CH_2-CH(CH_3)-OH$ | reddish yellow |
| 6 | | $-CH_2-CH_2-O-CH_2-CH_2-OH$ | reddish yellow |
| 7 | | $-CH_2-CH_2-O-CH_3$ | yellow |
| 8 | 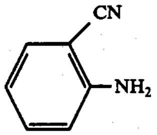 | H | reddish yellow |
| 9 | | $-CH_2-CH_2-OH$ | reddish yellow |
| 10 | | $-CH_2-CH_2-CH_2-OH$ | reddish yellow |
| 11 | | $-CH_2-CH(CH_3)-OH$ | reddish yellow |
| 12 | | $-CH_2-CH_2-O-CH_2-CH_2-OH$ | reddish yellow |
| 13 | 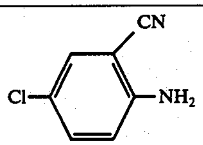 | $-H$ | reddish yellow |
| 14 | | $-CH_2-CH_2-OH$ | yellow |
| 15 | | $-CH_2-CH_2-CH_2-OH$ | yellow |
| 16 | | $-CH_2-CH_2(CH_3)-OH$ | yellow |
| 17 | | $-CH_2-CH_2-O-CH_2-CH_2-OH$ | yellow |

TABLE 1-continued

Coupling component:

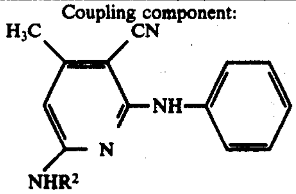

| Example No. | Diazo component | $R^2$ | Shade |
|---|---|---|---|
| 18 | 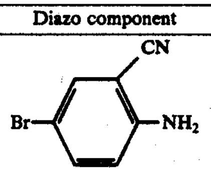 | $-H$ | yellow |
| 19 | | $-CH_2-CH_2-OH$ | yellow |
| 20 | | $-CH_2-CH_2-CH_2-OH$ | yellow |
| 21 | | $-CH_2-\underset{\overset{\vert}{CH_3}}{CH_2}-OH$ | yellow |
| 22 | | $-CH_2-CH_2-O-CH_2-CH_2-OH$ | yellow |
| 23 | 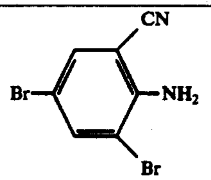 | H | reddish orange |
| 24 | | $-CH_2-CH_2-OH$ | yellowish red |
| 25 | | $-CH_2-CH_2-CH_2-OH$ | yellowish red |
| 26 | | $-CH_2-\underset{\overset{\vert}{CH_3}}{CH_2}-OH$ | yellowish red |
| 27 | | $-CH_2-CH_2-O-CH_2-CH_2-OH$ | yellowish red |
| 28 | 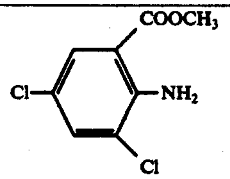 | H | reddish orange |
| 29 | | $-CH_2-CH_2-OH$ | yellowish red |
| 30 | | $-CH_2-CH_2-CH_2-OH$ | yellowish red |
| 31 | | $-CH_2-CH_2-O-CH_2-CH_2-OH$ | yellowish red |
| 32 | 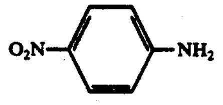 | H | orange |
| 33 | | $-CH_2-CH_2-OH$ | yellowish red |
| 34 | | $-CH_2-CH_2-CH_2-OCOCH_3$ | yellowish red |
| 35 | | $-CH_2-CH{<}^{OH}_{CH_3}$ | yellowish red |
| 36 | | $-CH_2-CH_2-O-CH_2-CH_2-OH$ | yellowish red |
| 37 | | $-CH_2-CH_2-O-CH_3$ | yellowish red |
| 38 | | $-CH_2-CH_2-CH_2-O-CH_3$ | yellowish red |
| 39 | | $-CH_2-CH_2-OCHO$ | reddish orange-yellowish red |
| 40 | | $-(CH_2)_6-OH$ | yellowish red |
| 41 | 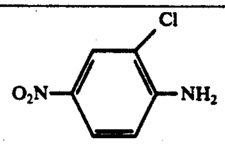 | $-H$ | yellowish red |
| 42 | | $-CH_2-CH_2-OH$ | yellowish red |
| 43 | | $-CH_2-CH_2-CH_2-OH$ | yellowish red |
| 44 | | $-CH_2-CH_2-O-CH_2-CH_2-OH$ | red |
| 45 | | $-CH_2-CH{<}^{OH}_{CH_3}$ | red |

TABLE 1-continued

Coupling component:

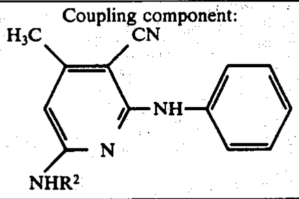

| Example No. | Diazo component | $R^2$ | Shade |
|---|---|---|---|
| 46 | | $-CH_2-CH_2-CH_2-O-CH_3$ | red |
| 47 | | $-CH_2-CH_2-CH_2-OCOCH_3$ | red |
| 48 | 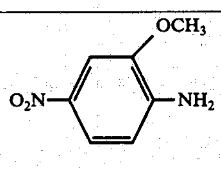 | $-CH_2-CH_2-OH$ | yellowish red |
| 49 | | $-CH_2-CH_2-CH_2-OH$ | yellowish red |
| 50 | | $-CH_2-CH_2-O-CH_2-CH_2-OH$ | yellowish red |
| 51 | 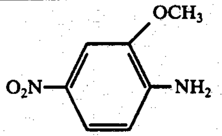 | $-CH_2-CH_2-OH$ | red |
| 52 | | $-CH_2-CH_2-CH_2-OH$ | red |
| 53 | | $-CH_2-CH_2-O-CH_2-CH_2-OH$ | red |
| 54 | 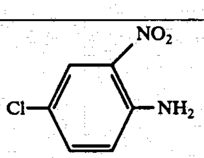 | $-CH_2-CH_2-OH$ | yellowish red |
| 55 | | $-CH_2-CH_2-CH_2-OH$ | yellowish red |
| 56 | 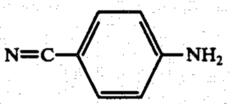 | $-CH_2-CH_2-OH$ | reddish yellow |
| 57 | | $-CH_2-CH_2-CH_2-OH$ | reddish yellow |
| 58 | | $-CH_2-CH_2-O-CH_2-CH_2-OH$ | reddish yellow |
| 59 | 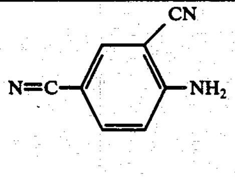 | $-CH_2-CH_2-OH$ | reddish orange |
| 60 | | $-CH_2-CH_2-CH_2-OH$ | reddish orange |
| 61 | | $-CH_2-CH_2-O-CH_2-CH_2-OH$ | reddish orange |
| 62 | 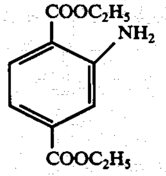 | $-CH_2-CH_2-OH$ | orange |
| 63 | | $-CH_2-CH_2-CH_2-OH$ | orange |
| 64 | | $-CH_2-CH_2-O-CH_2-CH_2-OH$ | orange |
| 65 | 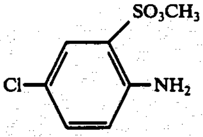 | H | orange |
| 66 | | $-CH_2-CH_2-OH$ | orange |
| 67 | | $-CH_2-CH_2-CH_2-OH$ | orange |
| 68 | | $-CH_2-CH_2-CH_2-O-CH_3$ | orange |
| 69 | 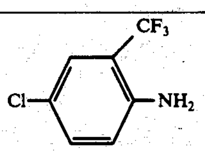 | $-CH_2-CH_2-OH$ | yellow |

TABLE 1-continued

Coupling component:

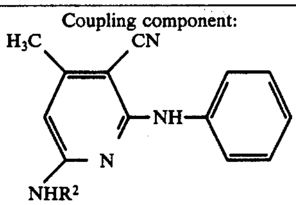

| Example No. | Diazo component | $R^2$ | Shade |
|---|---|---|---|
| 70 | | $-CH_2-CH_2-CH_2-OH$ | yellow |
| 71 | | $-CH_2-CH_2-O-CH_2-CH_2OH$ | yellow |
| 72 | 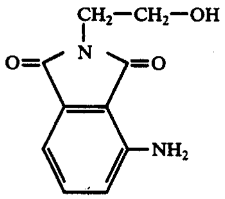 | $-H$ | yellow |
| 73 | | $-CH_2-CH_2-OH$ | orange |
| 74 | | $-CH_2-CH_2-CH_2-OH$ | orange |
| 75 | | $-CH_2-CH_2-O-CH_2-CH_2OH$ | orange |
| 76 | | $-CH_2-CH_2-O-CH_3$ | orange |
| 77 | 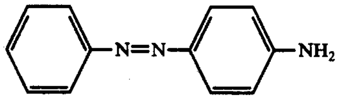 | $-CH_2-CH_2-CH_2-OH$ | red |
| 78 | | $-CH_2-CH_2-O-CH_2-CH_2$-<br>$-OH$ | red |
| 79 | 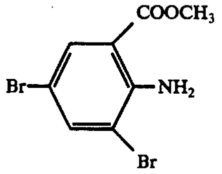 | $-CH_2-CH_2-CH_2-OH$ | yellowish red |
| 80 | | $-CH_2-CH_2-O-CH_2-CH_2$-<br>$-OH$ | yellowish red |
| 81 | 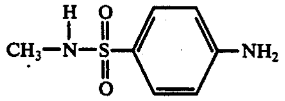 | $-CH_2-CH_2-OH$ | orange |
| 82 | | $-CH_2-CH_2-CH_2-OH$ | orange |
| 83 | | $-CH_2-CH_2-O-CH_2-CH_2$-<br>$-OH$ | orange |
| 84 | 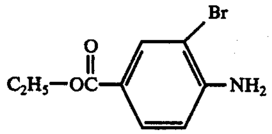 | $-CH_2-CH_2-OH$ | orange |
| 85 | | $-CH_2-CH_2-CH_2-OH$ | orange |
| 86 | | 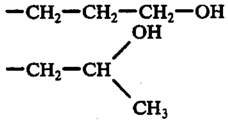 | orange |
| 87 | | $-CH_2-CH_2-O-CH_2-CH_2$-<br>$-OH$ | orange |
| 88 | 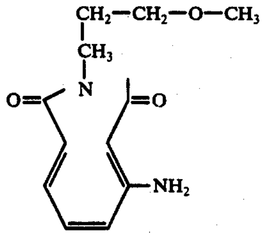 | $-CH_2-CH_2-OH$ | yellowish orange |
| 89 | | $-CH_2-CH_2-CH_2-OH$ | yellowish orange |
| 90 | | $-CH_2-CH_2-O-CH_2-CH_2$-<br>$-OH$ | yellowish orange |

TABLE 1-continued

Coupling component:

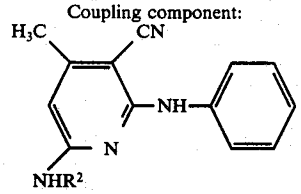

| Example No. | Diazo component | $R^2$ | Shade |
|---|---|---|---|
| 91 | 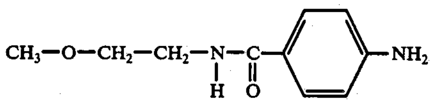 | $-CH_2-CH_2-OH$ | orange |
| 92 | | $-CH_2-CH_2-CH_2-OH$ | orange |
| 93 | 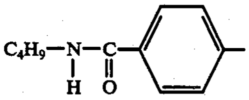 | $-CH_2-CH_2-OH$ | orange |
| 94 | | $-CH_2-CH_2-CH_2-OH$ | orange |

TABLE 2

Coupling component:

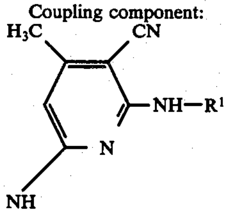

| Example No. | Diazo component | $R^1$ | Shade |
|---|---|---|---|
| 95 | 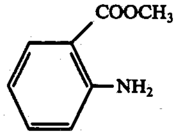 | $-CH_2-CH_2-OH$ | reddish yellow |
| 96 | | $-CH_2-CH_2-CH_2-OH$ | reddish yellow |
| 97 | | $-CH_2-CH_2-O-CH_2-CH_2-OH$ | reddish yellow |
| 98 | 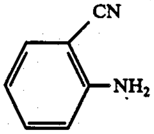 | $-CH_2-CH_2-OH$ | yellow |
| 99 | | $-CH_2-CH_2-CH_2-OH$ | yellow |
| 100 | | $-CH_2-CH_2-CH_2-O-CH_2-CH_2-OH$ | yellow |
| 101 | 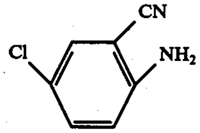 | $-CH_2-CH_2-OH$ | yellow |
| 102 | | $-CH_2-CH_2-CH_2-OH$ | yellow |
| 103 | | $-CH_2-CH_2-O-CH_2-CH_2-OH$ | yellow |
| 104 | 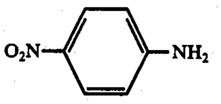 | $-CH_2-CH_2-OH$ | yellowish red |
| 105 | | $-CH_2-CH_2-CH_2-OH$ | yellowish red |
| 106 | | $-CH_2-CH_2-O-CH_2-CH_2-OH$ | yellowish red |
| 107 | 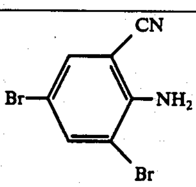 | $-CH_2-CH_2-CH_2-OH$ | yellowish red |
| 108 | | $-CH_2-CH_2-O-CH_2-CH_2-OH$ | yellowish red |

TABLE 2-continued

Coupling component:

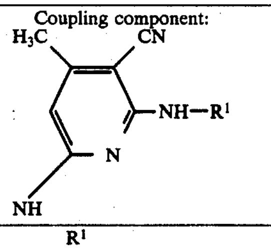

| Example No. | Diazo component | $R^1$ | Shade |
|---|---|---|---|
| 109 | 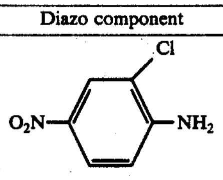 | $-CH_2-CH_2-CH_2-OH$ | red |
| 110 | | $-CH_2-CH_2-O-CH_2-CH_2-OH$ | red |
| 111 | 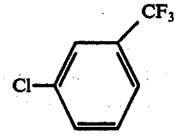 | $-CH_2-CH_2-CH_2-OH$ | yellow |
| 112 | | $-CH_2-CH_2-O-CH_2-CH_2-OH$ | yellow |
| 113 | 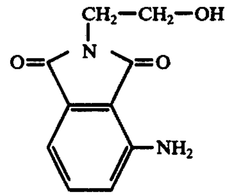 | $-CH_2-CH_2-OH$ | orange |
| 114 | | $-CH_2-CH_2-CH_2-OH$ | orange |
| 115 | | $-CH_2-CH_2-CH_2-O-CH_3$ | orange |

EXAMPLE 116

24.4 parts of the reaction product of aniline with 2,6-dichloro-3-cyano-4-methylpyridine (see Example 1) is stirred with 80 parts of γ-methoxypropylamine for eight hours under superatmospheric pressure at 140° to 160° C and then allowed to cool. 8 parts of 50% caustic soda solution is added and excess γ-methoxypropylamine and water are distilled off. The residue is treated with 100 parts of 85% sulfuric acid for five hours at 100° C and allowed to cool. The mixture is poured into a mixture of about 500 parts of water, 600 parts of ice and 100 parts of 50% caustic soda solution. The mixture, which contains the coupling component of the probable formula:

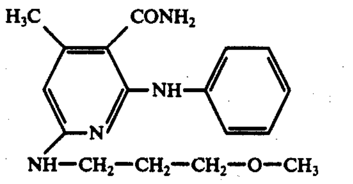

is cooled to 0° C and a solution of diazotized 3-amino-5-nitro-2,1-benzothiazole (prepared as follows) is then added in portions; 19.5 parts of 3-amino-5-nitro-2,1-benzoisothiazole is added in portions while stirring at 15° to 25° C to about 75 to 85 parts of 96% sulfuric acid and the whole is cooled to 0° to 4° C. 32.5 parts of 23% nitrosylsulfuric acid is then dripped in at the said temperature. Diazotization is over after stirring for about four hours at 0° to 5° C. After the diazonium solution has been added to the coupling mixture the pH of the mixture is raised to about 1.5 to 2.5 by adding an acid-binding agent such as sodium acetate (or caustic soda solution). It is convenient to add ice and ice-water to achieve efficient stirring at 0° to 5° C. After coupling is over the mixture is heated to 60° to 80° C and the precipitated dye is suction filtered, washed with hot water and dried. About 40 parts of a black dye powder of the probable formula:

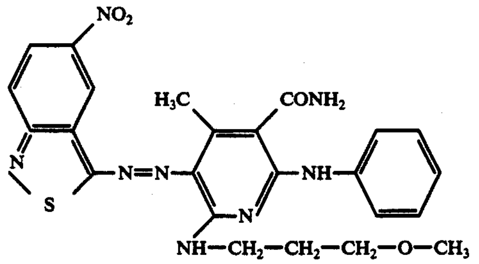

is obtained which dissolves in dimethylformamide with a blue color and dyes polyethylene terephthalate cloth greenish blue shades having very good fastness properties.

EXAMPLE 117

122 parts of the reaction product of aniline with 2,6-dichloro-3-cyano-4-methylpyridine (see Example 1) is treated with 150 parts of N-methylpyrrolidone and about 1000 parts of 25% ammonia for fifteen hours at 180° C in an autoclave. After cooling the precipitated product having the probable formula:

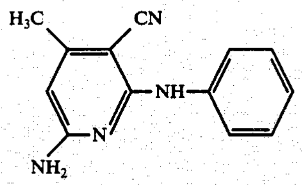

is filtered, washed with water and dried. About 108 parts of a colorless product is obtained.

22.4 parts of this product is dissolved in about 100 parts of glacial acetic acid, then cooled to 0° to 2° C with ice and some sulfamic acid is added. A solution of diazotized 2-amino-5-nitrobenzonitrile is added in portions to this coupling mixture at 0° C. The diazo solution is prepared as follows: 16.3 parts of 2-amino-5-nitrobenzonitrile is added in portions to a mixture, cooled to 0° C, of about 90 parts of 96% sulfuric acid and 32.5 parts of 23% nitrosylsulfuric acid. After stirring for about four to five hours at 0° to 4° C the diazotization is over.

In order to carry out coupling rapidly and completely the coupling mixture (which may be diluted with ice and ice-water) is adjusted at 0° to 5° C to pH about 2.5 by adding sodium acetate solution. After coupling is over the mixture is heated to about 80° C, the precipitated dye of the probable formula:

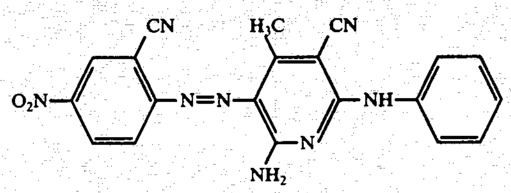

is filtered off, washed with hot water and dried. About 38 parts of a dark brown powder is obtained which dissolves in dimethylformamide with a red color and dyes polyethylene terephthalate cloth full pink to red shades having excellent fastness properties.

The dyes characterized in the following Table by the diazo and coupling components may be obtained analogously to the methods described in Example 1, 116 and 117.

TABLE 3

Coupling component

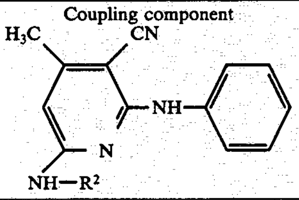

| Example No. | Diazo component | $R^2$ | Shade |
|---|---|---|---|
| 118 | 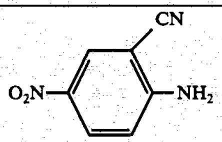 | $-CH_2-CH_2-OH$ | pink |
| 119 | | $-CH_2-CH_2-CH_2-OH$ | pink |
| 120 | | $-CH_2-CH(CH_3)-OH$ | pink |
| 121 | | $-CH_2-CH_2-O-CH_2-CH_2-OH$ | pink |
| 122 | | $-CH_2-CH_2-CH_2-OCHO$ | pink |
| 123 | | $-CH_2-CH_2-O-CH_3$ | pink |
| 124 | | $-(CH_2)_6-OH$ | pink |
| 125 | | $-CH_2-CH_2-O-COCH_3$ | pink |
| 126 | 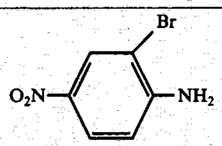 | $-CH_2-CH_2-OH$ | red |
| 127 | | $-CH_2-CH_2-CH_2-OH$ | red |
| 128 | | $-CH_2-CH(CH_3)-OH$ | red |
| 129 | | $-CH_2-CH_2-O-CH_2-CH_2-OH$ | red |
| 130 | | $-CH_2-CH_2-O-CH_3$ | yellowish red |
| 131 | 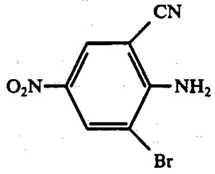 | $-H$ | red |
| 132 | | $-CH_2-CH_2-OH$ | red |
| 133 | | $-CH_2-CH_2-CH_2-OH$ | red |
| 134 | | $-CH_2-CH(CH_3)-OH$ | red |
| 135 | | $-CH_2-CH_2-O-CH_2-CH_2-OH$ | red |
| 136 | | $-CH_2-CH_2-O-CH_3$ | red |

TABLE 3-continued

Coupling component

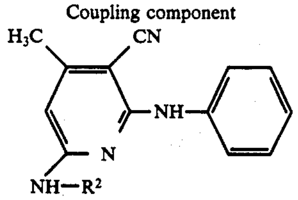

| Example No. | Diazo component | $R^2$ | Shade |
|---|---|---|---|
| 137 | | $-CH_2-CH_2-CH_2-O-CH_3$ | red |
| 138 | | $-CH_2-CH_2-O-COCH_3$ | red |
| 139 | 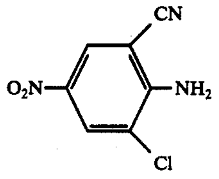 | $-H$ | red |
| 140 | | $-CH_2-CH_2-OH$ | red |
| 141 | | $-CH_2-CH_2-CH_2-OH$ | red |
| 142 | | $-CH_2-\underset{CH_3}{\underset{\vert}{CH}}-OH$ | red |
| 143 | | $-CH_2-CH_2-O-CH_2-CH_2-OH$ | red |
| 144 | | $-CH_2-CH_2-O-CH_3$ | red |
| 145 | | $-C_2H_5$ | red |
| 146 | 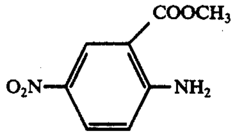 | $-CH_2-CH_2-OH$ | red |
| 147 | | $-CH_2-CH_2-CH_2-OH$ | red |
| 148 | | $-CH_2-CH_2-O-CH_2-CH_2-OH$ | red |
| 149 | 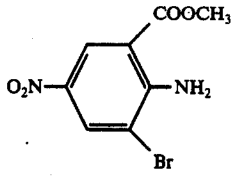 | $-CH_2-CH_2-OH$ | red |
| 150 | | $-CH_2-CH_2-CH_2-OH$ | red |
| 151 | | $-CH_2-CH_2-O-CH_2-CH_2-OH$ | red |
| 152 | 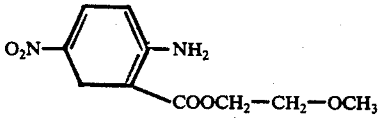 | $-CH_2-CH_2-OH$ | red |
| 153 | | $-CH_2-CH_2-CH_2-OH$ | red |
| 154 | 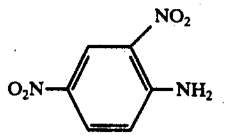 | $-H$ | red |
| 155 | | $-CH_2-CH_2-OH$ | red |
| 156 | | $-CH_2-CH_2-CH_2-OH$ | red |
| 157 | | $-CH_2-CH_2-O-CH_2-CH_2-OH$ | red |
| 158 | | $-CH_2-CH_2-O-CH_3$ | red |
| 159 | 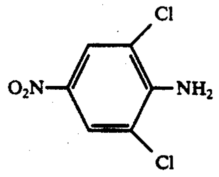 | $-CH_2-CH_2-OH$ | reddish brown |
| 160 | | $-CH_2-CH_2-CH_2-OH$ | reddish brown |
| 161 | | $-CH_2-CH_2-O-CH_2-CH_2-OH$ | reddish brown |
| 162 | | $-CH_2-CH_2-O-COCH_3$ | reddish brown |

TABLE 3-continued

Coupling component

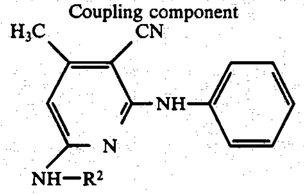

| Example No. | Diazo component | $R^2$ | Shade |
|---|---|---|---|
| 163 | 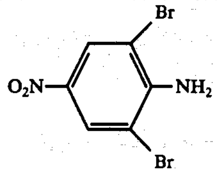 | $-CH_2-CH_2-OH$ | reddish brown |
| 164 | | $-CH_2-CH_2-CH_2-OH$ | reddish brown |
| 165 | | $-CH_2-\underset{CH_3}{CH}-OH$ | reddish brown |
| 166 | | $-CH_2-CH_2-O-CH_2-CH_2-OH$ | reddish brown |
| 167 | 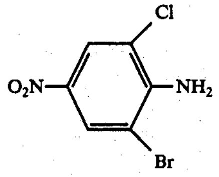 | $-CH_2-CH_2-OH$ | reddish brown |
| 168 | | $-CH_2-CH_2-CH_2-OH$ | reddish brown |
| 169 | | $-CH_2-CH_2-CH_2-O-CH_3$ | reddish brown |
| 170 | 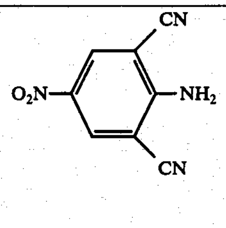 | $-CH_2-CH_2-O-H$ | violet |
| 171 | | $-CH_2-CH_2-CH_2-OH$ | violet |
| 172 | | $-CH_2-CH_2-O-CH_2-CH_2-OH$ | violet |
| 173 | | $-CH_2-CH_2-CH_2-O-CH_3$ | violet |
| 174 | 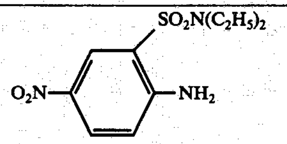 | $-CH_2-CH_2-OH$ | bluish red |
| 175 | | $-CH_2-CH_2-CH_2-OH$ | bluish red |
| 176 | 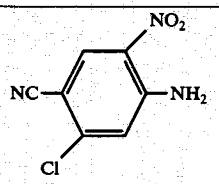 | $-CH_2-CH_2-OH$ | bluish red |
| 177 | | $-CH_2-CH_2-CH-OH$ | bluish red |
| 178 | | $-CH_2-CH_2-O-CH_2-CH_2-OH$ | bluish red |
| 179 | 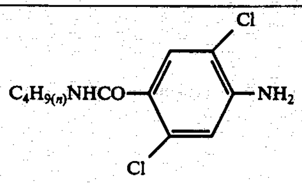 | $-CH_2-CH_2-OH$ | orange |
| 180 | | $-CH_2-CH_2-CH_2-OH$ | orange |
| 181 | | $-CH_2-CH_2-O-CH_2-CH_2-OH$ | orange |
| 182 | 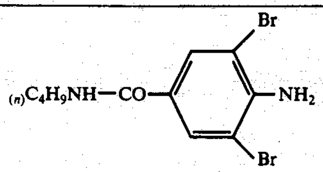 | $-CH_2-CH_2-OH$ | orange |
| 183 | | $-CH_2-CH_2-CH_2-OH$ | orange |
| 184 | | $-CH_2-CH_2-O-CH_2-CH_2-OH$ | orange |

TABLE 3-continued

Coupling component

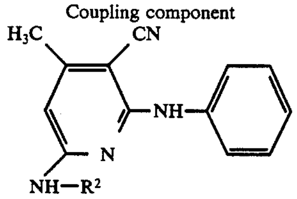

| Example No. | Diazo component | $R^2$ | Shade |
|---|---|---|---|
| 185 | 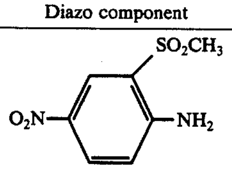 | $-H$ | bluish red |
| 186 | | $-CH_2-CH_2-OH$ | red |
| 187 | | $-CH_2-CH_2-CH_2-OH$ | red |
| 188 | | $-CH_2-\underset{CH_3}{\underset{\vert}{C}}H_2-OH$ | red |
| 189 | | $-(CH_2)_3-O-(CH_2)_4-OH$ | red |
| 190 | 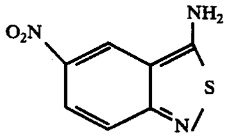 | $-CH_2-CH_2-OH$ | reddish blue |
| 191 | | $-CH_2-CH_2-CH_2-OH$ | navy |
| 192 | | $-CH_2-\underset{CH_3}{\underset{\vert}{C}}H-OH$ | navy |
| 193 | | $-CH_2-CH_2-O-CH_2-CH_2-OH$ | navy |
| 194 | | $-(CH_2)_6-OH$ | navy |
| 195 | | $-(CH_2)_3-O-(CH_2)_4-OH$ | navy |
| 196 | | $-CH_2-CH_2-CH_2-O-\underset{O}{\underset{\Vert}{C}}-CH_3$ | reddish blue |
| 197 | 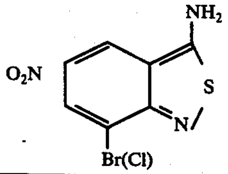 | $-CH_2-CH_2-O-CH_2-CH_2-OH$ | blue |
| 198 | 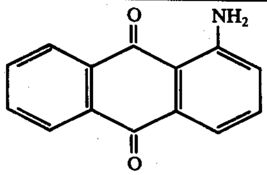 | $-CH_2-CH_2-CH_2-OH$ | reddish brown |
| 199 | | $-CH_2-CH_2-O-CH_2-CH_2-OH$ | reddish brown |
| 200 | 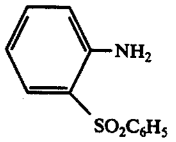 | $-CH_2-CH_2-CH_2-OH$ | yellow |
| 201 | | $-CH_2-CH_2-O-CH_2-CH_2-OH$ | yellow |
| 202 | 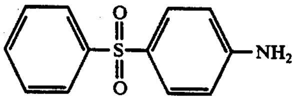 | $-CH_2-CH_2-O-CH_2-CH_2-OH$ | yellow |
| 203 | | $-(CH_2)_3-O-H$ | yellow |
| 204 | 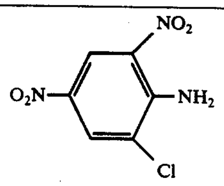 | $-CH_2-CH_2-OH$ | violet |
| 205 | | $-CH_2-CH_2-CH_2-OH$ | violet |

TABLE 3-continued

Coupling component

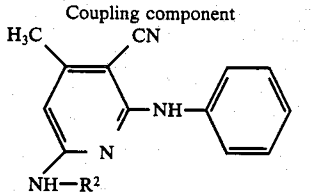

| Example No. | Diazo component | $R^2$ | Shade |
| --- | --- | --- | --- |
| 206 | | $-CH_2-CH(OH)-OH$ | violet |
| 207 | | $-CH_2-CH_2-O-CH_2-CH_2-OH$ | violet |
| 208 | 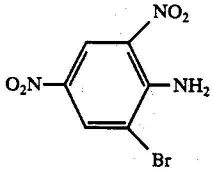 | $-(CH_2)_3-OH$ | violet |
| 209 | | $-CH_2-CH_2-O-CH_2-CH_2-OH$ | violet |
| 210 | 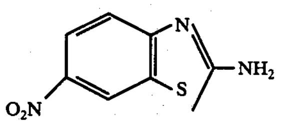 | $-CH_2-CH_2-CH_2-OH$ | yellowish red |
| 211 | | $-CH_2-CH_2-O-CH_2-CH_2-OH$ | yellowish red |
| 212 | 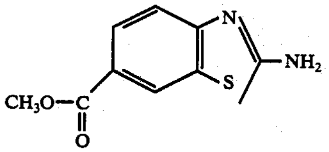 | $-CH_2-CH_2-CH_2-OH$ | yellowish red |
| 213 | | $-CH_2-CH_2-O-CH_2-CH_2-OH$ | yellowish red |
| 214 | 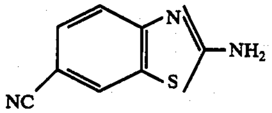 | $-CH_2-CH_2-CH_2-OH$ | yellowish red |
| 215 | | $-CH_2-CH_2-O-CH_2-CH_2-OH$ | yellowish red |
| 216 | 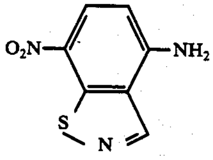 | $-CH_2-CH_2-OH$ | red |
| 217 | | $-CH_2-CH_2-CH_2-OH$ | red |
| 218 | | $-CH_2-CH_2-O-CH_2-CH_2-OH$ | red |
| 219 | | $-(CH_2)_3-O-(CH_2)_4-OH$ | red |
| 220 | 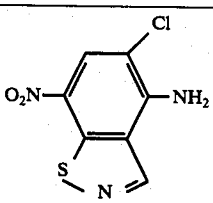 | $-CH_2-CH_2-CH_2-OH$ | violet |
| 221 | | $-CH_2-CH_2-O-CH_2-CH_2-OH$ | violet |
| 222 | | $-(CH_2)_3-O-(CH_2)_4-OH$ | violet |
| 223 | 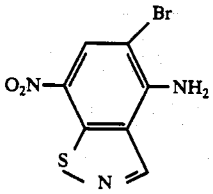 | $-CH_2-CH_2-CH_2-OH$ | violet |
| 224 | | $-CH_2-CH_2-O-CH_2-CH_2-OH$ | violet |

TABLE 3-continued

Coupling component

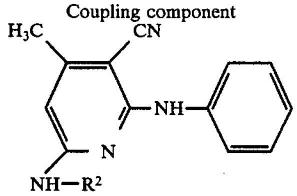

| Example No. | Diazo component | $R^2$ | Shade |
|---|---|---|---|
| 225 | 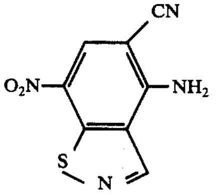 | $-CH_2-CH_2-CH_2-OH$ | violet |
| 226 | | $-CH_2-CH_2-O-CH_2-CH_2-OH$ | violet |
| 227 | 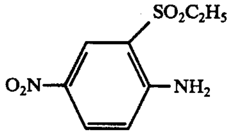 | $-CH_2-CH_2-CH_2-OH$ | red |
| 228 | 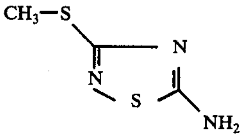 | $-H$ | reddish orange |
| 229 | | $-CH_2-CH_2-OH$ | yellowish red |
| 230 | | $-CH_2-CH_2-CH_2-OH$ | yellowish red |
| 231 | | $-CH_2-CH_2-O-CH_2-CH_2-OH$ | yellowish red |
| 232 | 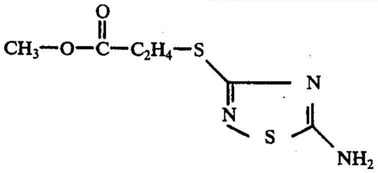 | $-CH_2-CH_2-OH$ | yellowish red |
| 233 | | $-CH_2-CH_2-CH_2-OH$ | yellowish red |
| 234 | | $-CH_2-CH-OH$<br>$\vert$<br>$CH_3$ | yellowish red |
| 235 | | $-CH-CH-O-CH-CH-OH$ | yellowish red |
| 236 | | $-H$ | reddish orange |
| 237 | 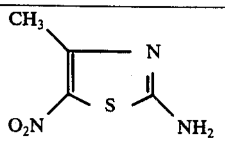 | $-CH_2-CH_2-OH$ | violet |
| 238 | | $-CH_2-CH_2-CH_2-OH$ | violet |
| 239 | | $-CH_2-CH_2-O-CH_2-CH_2-OH$ | violet |
| 240 | 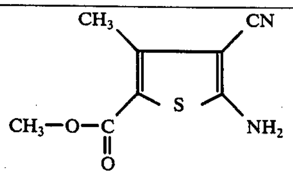 | $-CH_2-CH_2-OH$ | bluish red |
| 241 | | $-CH_2-CH_2-CH_2-OH$ | reddish violet |
| 242 | | $-CH_2-CH_2-O-CH_2-CH_2-OH$ | reddish violet |
| 243 | | $-CH_2-CH-OH$<br>$\vert$<br>$CH_3$ | reddish violet |
| 244 | 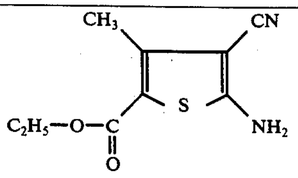 | $-CH_2-CH_2-OH$ | reddish violet |
| 245 | | $-CH_2-CH_2-CH_2-OH$ | reddish violet |
| 246 | | $-CH_2-CH_2-O-CH_2-CH_2-OH$ | reddish violet |

TABLE 3-continued

Coupling component

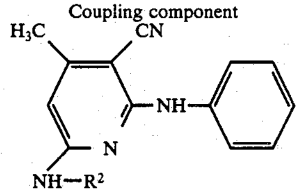

| Example No. | Diazo component | $R^2$ | Shade |
| --- | --- | --- | --- |
| 247 | 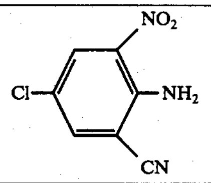 | $-CH_2-CH_2-CH_2-OH$ | red |
| 248 | 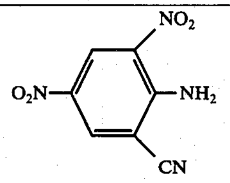 | $-CH_2-CH_2-CH_2-OH$ | violet |
| 249 | | $-CH_2-CH_2-O-CH_2-CH_2-OH$ | violet |
| 250 | 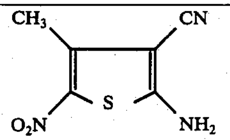 | $-CH_2-CH_2-OH$ | reddish blue |
| 251 | | $-CH_2-CH_2-CH_2-OH$ | reddish blue |
| 252 | | $-CH_2-CH_2-O-CH_2-CH_2-OH$ | reddish blue |
| 253 | 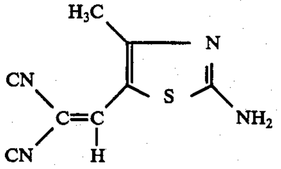 | $-CH_2-CH_2-CH_2-OH$ | blue |

TABLE 4

Coupling component

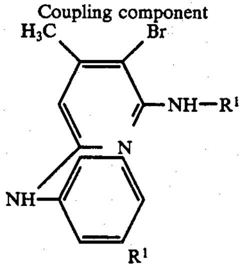

| Example No. | Diazo component | $R^1$ | Shade |
| --- | --- | --- | --- |
| 254 | 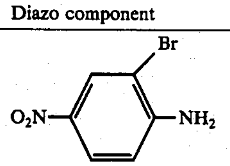 | $-CH_2-CH_2-OH$ | red |
| 255 | | $-CH_2-CH_2-CH_2-OH$ | red |
| 256 | | $-CH_2-CH_2-O-CH_2-CH_2-OH$ | red |
| 257 | 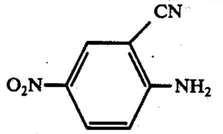 | $-H$ | pink |
| 258 | | $-CH_2-CH_2-OH$ | red |
| 259 | | $-CH_2-CH_2-O-COCH_3$ | pink |
| 260 | | $-CH_2-CH_2-CH_2-OH$ | red |
| 261 | | $-CH_2-CH_2-O-CH_2-CH_2-OH$ | pink |
| 262 | | $-CH_2-CH_2-O-CH_2-CH_2-OCHO$ | pink |
| 263 | | $-(CH_2)_6-OH$ | red |

TABLE 4-continued

Coupling component

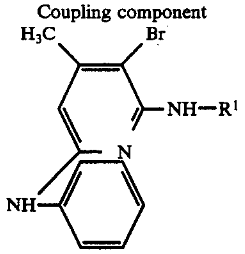

| Example No. | Diazo component | $R^1$ | Shade |
|---|---|---|---|
| 264 | 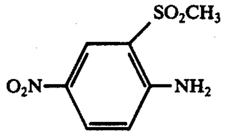 | $-CH_2-CH_2-CH_2-OH$ | red |
| 265 | | $-CH_2-CH_2-O-CH_2-CH_2-OH$ | red |
| 266 | 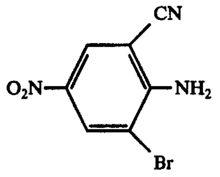 | $-H$ | red |
| 267 | | $-CH_2-CH_2-OH$ | red |
| 268 | | $-CH_2-CH_2-CH_2-OH$ | red |
| 269 | | $-CH_2-CH(CH_3)-OH$ | red |
| 270 | | $-CH_2-CH_2-O-CH_2-CH_2-OH$ | red |
| 271 | 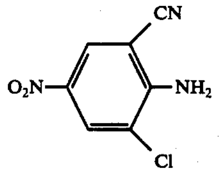 | $-CH_2-CH_2-OH$ | red |
| 272 | | $-CH_2-CH_2-CH_2-OH$ | red |
| 273 | | $-CH_2-CH_2-O-CH_2-CH_2OH$ | red |
| 274 | | $-(CH_2)_3-O-(CH_2)_4-OH$ | red |
| 275 | 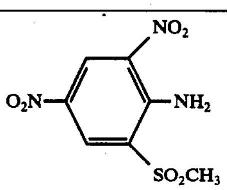 | $-CH_2-CH_2-CH_2-OH$ | violet |
| 276 | 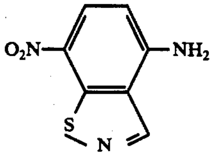 | $-CH_2-CH_2-CH_2-OH$ | red |
| 277 | | $-CH_2-CH_2-O-CH_2-CH_2-OH$ | red |
| 278 | 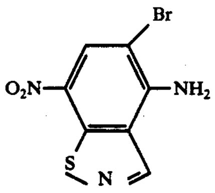 | $-CH_2-CH_2-CH_2-OH$ | violet |
| 279 | | $-CH_2-CH_2-O-CH_2-CH_2-OH$ | violet |
| 280 | 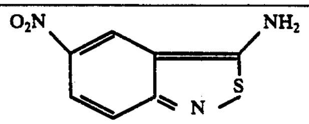 | $-CH_2-CH_2-CH_2-OH$ | navy |
| 281 | | $-CH_2-CH_2-O-CH_2-CH_2-OH$ | navy |

TABLE 4-continued

Coupling component

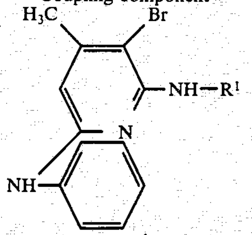

| Example No. | Diazo component | $R^1$ | Shade |
| --- | --- | --- | --- |
| 282 | 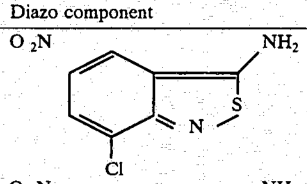 | $-CH_2-CH_2-O-CH_2-CH_2-OH$ | blue |
| 283 | 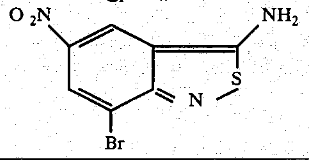 | $-CH_2-CH_2-O-CH_2-CH_2-OH$ | blue |
| 284 | 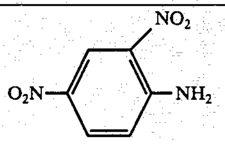 | $-CH_2-CH_2-OH$ | red |
| 285 | | $-CH_2-CH_2-CH_2-OH$ | red |
| 286 | | $-CH_2-CH_2-O-CH_2-CH_2-OH$ | red |
| 287 | 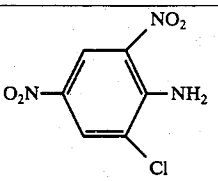 | $-CH_2-CH_2-CH_2-OH$ | violet |
| 288 | | $-CH_2-CH_2-O-CH_2-CH_2-OH$ | violet |
| 289 | 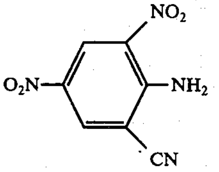 | $-CH_2-CH_2-CH_2-OH$ | violet |
| 290 | | $-CH_2-CH_2-O-CH_2-CH_2-OH$ | violet |
| 291 | 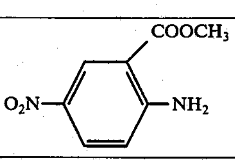 | $-CH_2-CH_2-CH_2-OH$ | red |
| 292 | | $-CH_2-CH_2-O-CH_2-CH_2-OH$ | red |

TABLE 5

Coupling component:

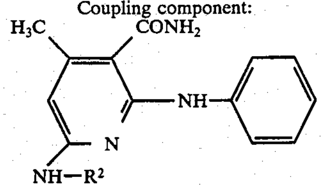

| Example No. | Diazo component | $R^2$ | Shade |
| --- | --- | --- | --- |
| 293 | 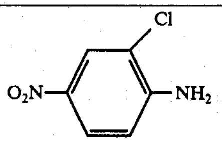 | $-CH_2-CH_2-O-COCH_3$ | red |
| 294 | | $-CH_2-CH_2-CH_2-O-COCH_3$ | red |

TABLE 5-continued

Coupling component:

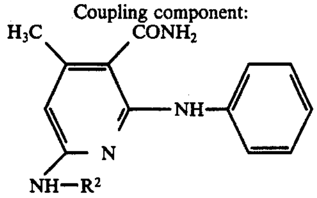

| Example No. | Diazo component | $R^2$ | Shade |
|---|---|---|---|
| 295 | | $-CH_2-CH_2-CH_2-OH$ | red |
| 296 | | $-CH_2-CH_2-O-CH_3$ | red |
| 297 | 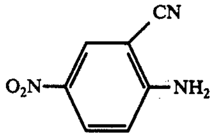 | $-CH_2-CH_2-OCOCH_3$ | bluish red |
| 298 | | $-CH_2-CH_2-CH_2-OCOCH_3$ | bluish red |
| 299 | | $-CH_2-CH_2-CH_2-OH$ | bluish red |
| 300 | | $-CH_2-CH_2-O-CH_2-CH_2-OCOCH_3$ | bluish red |
| 301 | | $-CH_2-CH_2-O-CH_2-CH_2-OH$ | bluish red |
| 302 | | $-CH_2-CH_2-O-CH_3$ | bluish red |
| 303 | 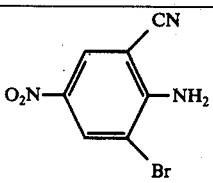 | $-CH_2-CH_2-CH_2-OCOCH_3$ | violet |
| 304 | | $-CH_2-CH_2-CH_2-OH$ | violet |
| 305 | | $-CH_2-CH_2-O-CH_2-CH_2-OCOCH_3$ | violet |
| 306 | | $-CH_2-CH_2-O-CH_2-CH_2-OH$ | violet |
| 307 | | $-CH_2-CH_3$ | violet |
| 308 | | $-CH_2-CH_2-CH_2-O-CH_3$ | violet |
| 309 | 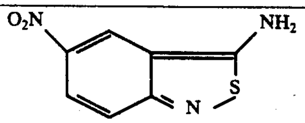 | $-CH_2-CH_2-O-COCH_2-COCH_3$ | greenish blue |
| 310 | | $-CH_2-CH_2-OCOCH_3$ | greenish blue |
| 311 | | $-CH_2-CH_2-CH_2-O-COCH_3$ | greenish blue |
| 312 | | $-CH_2-CH_2-CH_2-OH$ | greenish blue |
| 313 | | $-CH_2-CH_2-O-CH_3$ | greenish blue |
| 314 | | $-CH_2-CH_2-CH_2-O-C_2H_5$ | greenish blue |
| 315 | | $-CH_2-CH_2-O-CH_2-CH_2-O-CHO$ | greenish blue |
| 316 | | $-CH_2-CH_2-O-CH_2-CH_2-OH$ | greenish blue |
| 317 | | $-CH_2-CH_2-O-CH_2-CH_2-O-COCH_3$ | greenish blue |
| 318 | 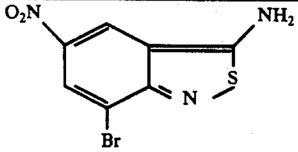 | $-CH_2-CH_2-O-CH_2-CH_2-O-COCH_3$ | greenish blue |

TABLE 6

Coupling component:

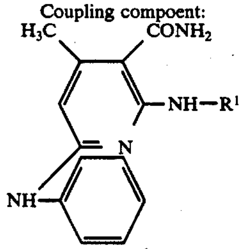

| Example No. | Diazo component | $R^1$ | Shade |
|---|---|---|---|
| 319 | 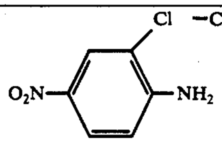 | $-CH_2-CH_2-CH_2-OCOCH_3$ | red |
| 320 | | $-CH_2-CH_2-CH_2-OH$ | red |

TABLE 6-continued

Coupling component:

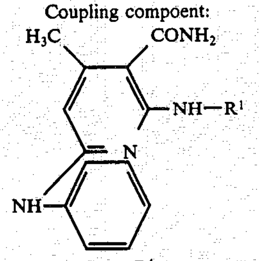

| Example No. | Diazo component | $R^1$ | Shade |
|---|---|---|---|
| 321 | 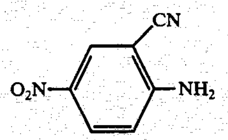 | $-CH_2-CH_2-CH_2-OCOCH_3$ | bluish red |
| 322 | | $-CH_2-CH_2-CH_2-OH$ | bluish red |
| 323 | | $-CH_2-CH_2-O-CH_2-CH_2-OCOCH_3$ | bluish red |
| 324 | | $-CH_2-CH_2-O-CH_2-CH_2-OCHO$ | bluish red |
| 325 | 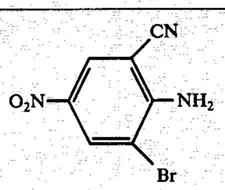 | $-CH_2-CH_2-CH_2-O-COCH_3$ | violet |
| 326 | | $-CH_2-CH_2-O-CH_2-CH_2-OCHO$ | violet |
| 327 | | $-CH_2-CH_2-O-CH_2-CH_2-O-COCH_3$ | violet |
| 328 | 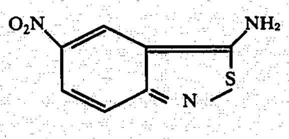 | $-CH_2-CH_2-CH_2-O-COCH_3$ | greenish blue |
| 329 | | $-CH_2-CH_2-CH_2-OCOCH_2-COCH_3$ | greenish blue |
| 330 | | $-CH_2-CH_2-CH_2-OH$ | greenish blue |
| 331 | | $-CH_2-CH_2-O-CH_2-CH_2-OH$ | greenish blue |
| 332 | | $-CH_2-CH_2-O-CH_2-CH_2-OCHO$ | greenish blue |
| 333 | | $-CH_2-CH_2-O-CH_2-CH_2-OCOCH_3$ | greenish blue |
| 334 | 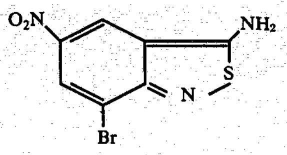 | $-CH_2-CH_2-O-CH_2-CH_2-OCHO$ | greenish blue |
| 335 | | $-CH_2-CH_2-O-CH_2-CH_2-O-COCH_3$ | greenish blue |
| 336 | | $-CH_2-CH_2-O-CH_2-CH_2-OH$ | greenish blue |
| 337 | | $-(CH_2)_3-O-(CH_2)_4-OH$ | greenish blue |
| 338 | 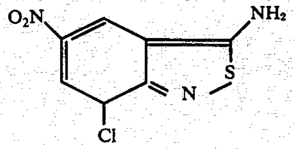 | $-CH_2-CH_2-O-CH_2-CH_2-OCOCH_3$ | greenish blue |
| 339 | | $-CH_2-CH_2-O-CH_3$ | greenish blue |

The following dyes may be prepared analogously:

| Example No. | | |
|---|---|---|
| 340 | 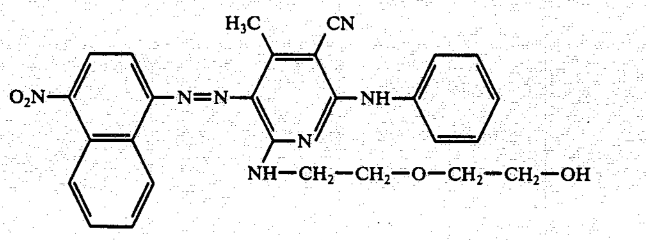 | red |

-continued

| Example No. | | |
|---|---|---|
| 341 | 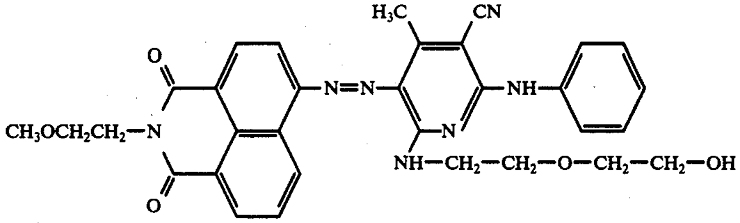 | bluish red |
| 342 | 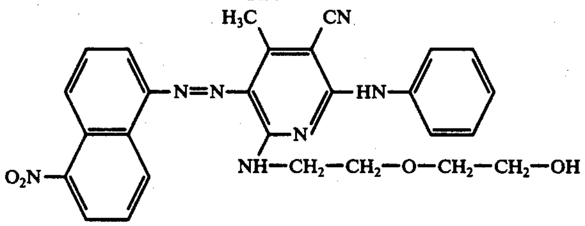 | orange |
| 343 | 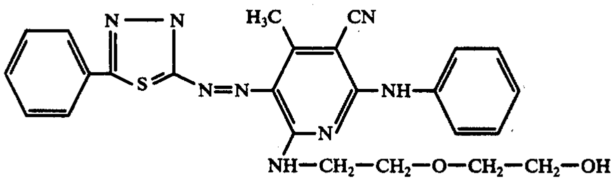 | yellowish red |

EXAMPLE 344

11 parts of the dye of the formula:

(Example 118)

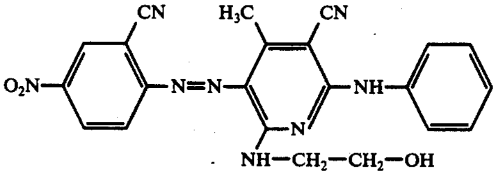

is heated under reflux with 100 parts by volume of formic acid for four hours. After cooling about 100 parts of water is added with stirring and the precipitate of the formula:

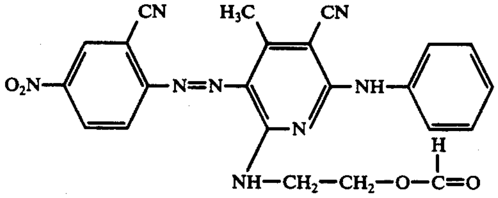

which is thrown down is filtered, washed with water and dried. About 11 parts of a brown powder is obtained which dissolves in dimethylformamide with a red color and dyes polyethylene terephthalate cloth pink to red shades of outstanding fastness properties.

EXAMPLE 345

A mixture of 187 parts of 2,6-dichloro-3-cyano-4-methylpyridine, 200 parts of isopropanol and 300 parts of 2-phenylpropylamine is stirred for eight hours at about 45° to 55° C. The mixture is then allowed to cool and is poured with stirring into about 1500 parts of water, 200 parts of concentrated hydrochloric acid and 200 parts of ice. The whole is stirred for another hour and the deposited precipitate of the probable formula:

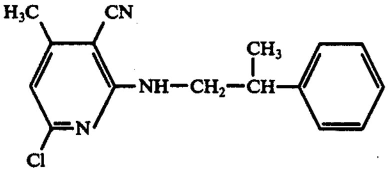

is suction filtered, washed with water until neutral and dried. About 240 parts of a colorless powder is obtained which melts at 100° to 105° C.

15 parts of this powder is stirred with 40 parts of β-hydroxyethylamine for six hours at 145° to 160° C. The mixture is then allowed to cool and is acidified with hydrochloric acid to a pH of from about 0 to 1. If necessary some glacial acetic acid or dimethylformamide is added. A solution of the coupling component of the probable formula:

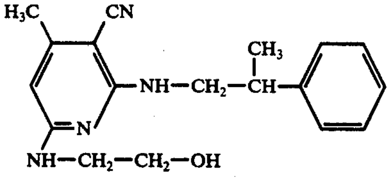

is obtained.

The solution or suspension of this coupling component is cooled to 0° to 3° C by adding ice and a diazonium salt solution is added which has been obtained as follows:

6.9 parts of p-nitroaniline has about 30 parts of concentrated hydrochloric acid (30%) and 80 parts of water added to it and the mixture is then cooled to 0° C and 15 parts by volume of 23% sodium nitrite solution is added in portions. The whole is stirred for another two hours, any excess of nitrous acid present is removed in the usual way, and the whole is filtered.

The filtrate is added to the coupling mixture and then while stirring such an amount of sodium acetate is gradually added that the pH of the coupling mixture is from about 2 to 3. If the mixture is difficult to stir ice-water may be added. When the coupling is ended the mixture is heated to 70° to 80° C, filtered, washed with water and dried. About 20 parts of a brown powder of the probable formula:

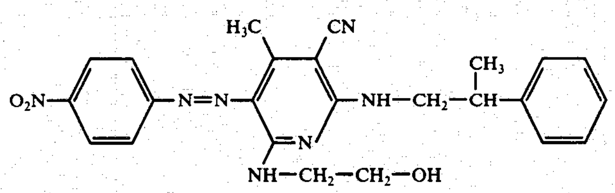

is obtained which dissolves in dimethylformamide with an orange color and dyes polyethylene terephthalate cloth full, clear orange shades of outstanding fastness properties.

The following dyes characterized by the diazo and coupling components may be obtained analogously to the methods described:

TABLE 1

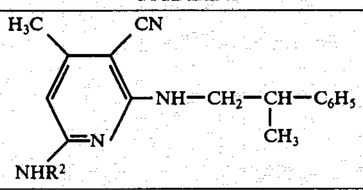

| Example No. | Diazo component | $R^2$ | Shade |
|---|---|---|---|
| 346 | 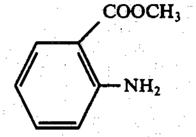 | H | yellow |
| 347 | | $-CH_2-CH_2-OH$ | yellow |
| 348 | | $-CH_2-CH_2-OH$ | yellow |
| 349 | | $-CH_2-\underset{CH_3}{CH}-OH$ | yellow |
| 350 | | $-CH_2-CH_2-O-CH_2-CH_2-OH$ | yellow |
| 351 | | $-CH_2-CH_2-O-CH_3$ | yellow |
| 352 | 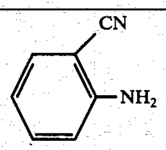 | H | yellow |
| 353 | | $-CH_2-CH_2-OH$ | yellow |
| 354 | | $-CH_2-CH_2-CH_2-OH$ | yellow |
| 355 | | $-CH_2-\underset{CH_3}{CH}-OH$ | yellow |
| 356 | | $-CH_2-CH_2-O-CH_2-CH_2-OH$ | yellow |
| 357 | 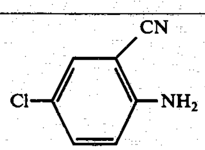 | $-H$ | yellow |
| 358 | | $-CH_2-CH_2-OH$ | yellow |
| 359 | | $-CH_2-CH_2-CH_2-OH$ | yellow |
| 360 | | $-CH_2-\underset{CH_3}{CH_2}-OH$ | yellow |
| 361 | | $-CH_2-CH_2-O-CH_2-CH_2-OH$ | yellow |
| 362 | 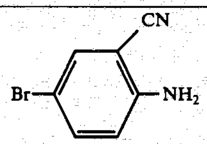 | yellow | |
| 363 | | $-CH_2-CH_2-OH$ | yellow |
| 364 | | $-CH_2-CH_2-CH_2-OH$ | yellow |
| 365 | | $-CH_2-\underset{CH_3}{CH}-OH$ | yellow |
| 366 | | $-CH_2-CH_2-O-CH_2-CH_2-OH$ | yellow |

TABLE 1-continued

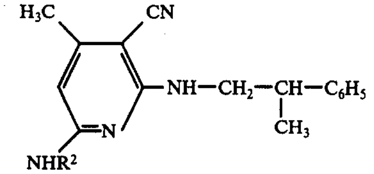

| Example No. | Diazo component | $R^2$ | Shade |
|---|---|---|---|
| 367 | 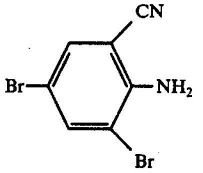 | H | orange |
| 368 | | $-CH_2-CH_2-OH$ | orange |
| 369 | | $-CH_2-CH_2-CH_2-OH$ | orange |
| 370 | | 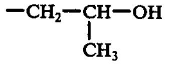 | orange |
| 371 | | $-CH_2-CH_2-O-CH_2-CH_2-OH$ | orange |
| 372 | 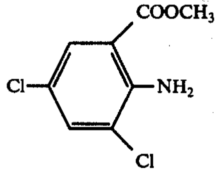 | H | orange |
| 373 | | $-CH_2-CH_2-OH$ | orange |
| 374 | | $-CH_2-CH_2-CH_2-OH$ | orange |
| 375 | | $-CH_2-CH_2-O-CH_2-CH_2-OH$ | orange |
| 376 | 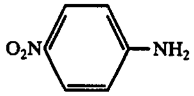 | H | orange |
| 377 | | $-CH_2-CH_2-OH$ | orange |
| 378 | | $-CH_2-CH_2-CH_2-OCOCH_3$ | orange |
| 379 | | 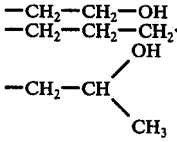 | orange |
| 380 | | $-CH_2-CH_2-O-CH_2-CH_2-OH$ | orange |
| 381 | | $-CH_2-CH_2-O-CH_3$ | orange |
| 382 | | $-CH_2-CH_2-CH_2-O-CH_3$ | orange |
| 383 | | $-CH_2-CH_2-OCHO$ | orange |
| 384 | | $-(CH_2)_6-OH$ | orange |
| 385 | 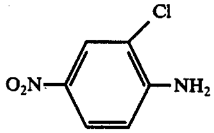 | $-H$ | yellowish red |
| 386 | | $-CH_2-CH_2-OH$ | yellowish red |
| 387 | | $-CH_2-CH_2-CH_2-OH$ | yellowish red |
| 388 | | $-CH_2-CH_2-O-CH_2-CH_2-OH$ | yellowish red |
| 389 | | 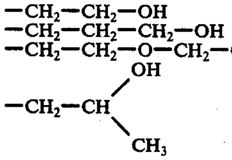 | yellowish red |
| 390 | | $-CH_2-CH_2-CH_2-O-CH_3$ | yellowish red |
| 391 | | $-CH_2-CH_2-CH_2-OCOCH_3$ | yellowish red |
| 392 | 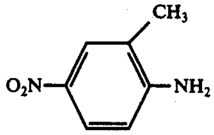 | $-CH_2-CH_2-OH$ | yellowish red |
| 393 | | $-CH_2-CH_2-CH_2-OH$ | yellowish red |
| 394 | | $-CH_2-CH_2-O-CH_2-CH_2-OH$ | yellowish red |
| 395 | 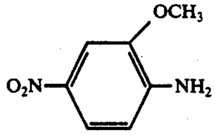 | $-CH_2-CH_2-OH$ | yellowish red |
| 396 | | $-CH_2-CH_2-OH$ | yellowish red |

TABLE 1-continued

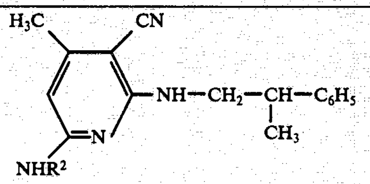

| Example No. | Diazo component | $R^2$ | Shade |
|---|---|---|---|
| 397 | | $-CH_2-CH_2-O-CH_2-CH_2-OH$ | yellowish red |
| 398 | 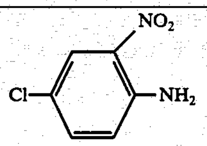 | $-CH_2-CH_2-OH$ | orange |
| 399 | | $-CH_2-CH_2-CH_2-OH$ | orange |
| 400 | 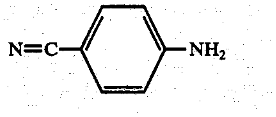 | $-CH_2-CH_2-OH$ | yellow |
| 401 | | $-CH_2-CH_2-CH_2-OH$ | yellow |
| 402 | | $-CH_2-CH_2-O-CH_2-CH_2-OH$ | yellow |
| 403 | 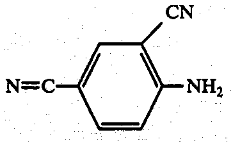 | $-CH_2-CH_2-OH$ | orange |
| 404 | | $-CH_2-CH_2-CH_2-OH$ | orange |
| 405 | | $-CH_2-CH_2-O-CH_2-CH_2-OH$ | orange |
| 406 | 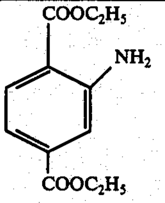 | $-CH_2-CH_2-OH$ | yellow |
| 407 | | $-CH_2-CH_2-CH_2-OH$ | yellow |
| 408 | | $-CH_2-CH_2-O-CH_2-CH_2-OH$ | yellow |
| 409 | 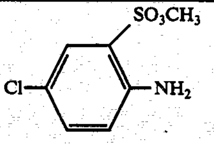 | H | yellow |
| 410 | | $-CH_2-CH_2-OH$ | yellow |
| 411 | | $-CH_2-CH_2-OH$ | yellow |
| 412 | | $-CH_2-CH_2-CH_2-O-CH_3$ | yellow |
| 413 | 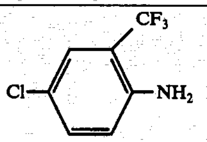 | $-CH_2-CH_2-OH$ | yellow |
| 414 | | $-CH_2-CH_2-CH_2-OH$ | yellow |
| 415 | | $-CH_2-CH_2-O-CH_2-CH_2-OH$ | yellow |
| 416 | 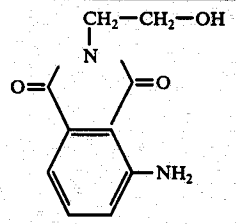 | $-H$ | yellow |
| 417 | | $-CH_2-CH_2-OH$ | yellow |
| 418 | | $-CH_2-CH_2-CH_2-OH$ | yellow |
| 419 | | $-CH_2-CH_2-O-CH_2-CH_2-OH$ | yellow |
| 420 | | $-CH_2-CH_2-O-CH_3$ | yellow |
| 421 | 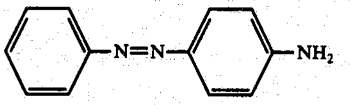 | $-CH_2-CH_2-CH_2-OH$ | yellowish red |

TABLE 1-continued
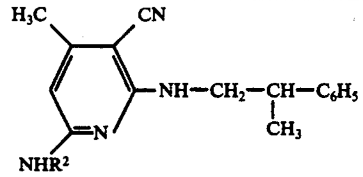
| Example No. | Diazo component | $R^2$ | Shade |
| --- | --- | --- | --- |
| 422 | | $-CH_2-CH_2-OH$ | yellowish red |
| 423 | 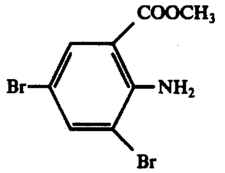 | $-CH_2-CH_2-CH_2-OH$ | orange |
| 424 | | $-CH_2-CH_2-O-CH_2-CH_2-OH$ | orange |
| 425 | 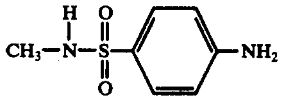 | $-CH_2-CH_2-OH$ | yellow |
| 426 | | $-CH_2-CH_2-CH_2-OH$ | yellow |
| 427 | | $-CH_2-CH_2-O-CH_2-CH_2-OH$ | yellow |
| 428 | 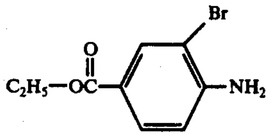 | $-CH_2-CH_2-OH$ | yellow |
| 429 | | $-CH_2-CH_2-CH_2-OH$ | yellow |
| 430 | | 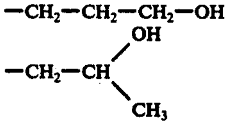 | yellow |
| 431 | | $-CH_2-CH_2-O-CH_2-CH_2-OH$ | yellow |
| 432 | 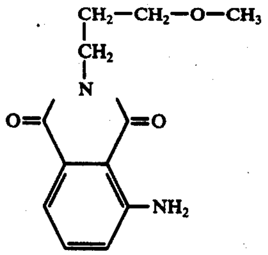 | $-CH_2-CH_2-OH$ | yellow |
| 433 | | $-CH_2-CH_2-CH_2-OH$ | yellow |
| 434 | | | |
| 435 | 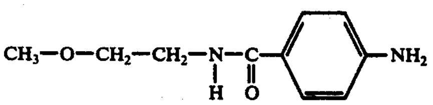 | $-CH_2-CH_2-OH$ | yellow |
| 436 | | $-CH_2-CH_2-CH_2-OH$ | yellow |
| 437 | 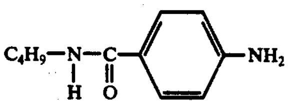 | $-CH_2-CH_2-OH$ | yellow |
| 438 | | $-CH_2-CH_2-CH_2-OH$ | yellow |

TABLE 2

Coupling component:

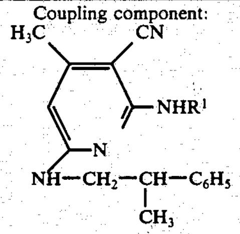

| Example | Diazo component | $R_1$ | Shade |
|---|---|---|---|
| 439 | 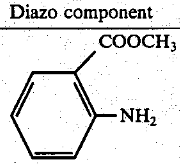 | $-CH_2-CH_2-OH$ | yellow |
| 440 | | $-CH_2-CH_2-CH_2-OH$ | yellow |
| 441 | | $-H$ | yellow |
| 442 | 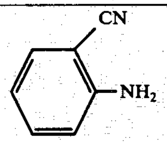 | $-CH_2-CH_2-OH$ | yellow |
| 443 | | $-CH_2-CH_2-CH_2-OH$ | yellow |
| 444 | | $-CH_2-CH_2-CH_2-O-(CH_2)_2OH$ | yellow |
| 445 | 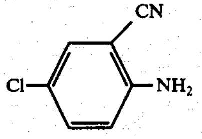 | $-CH_2-CH_2-OH$ | yellow |
| 446 | | $-CH_2-CH_2-CH_2-OH$ | yellow |
| 447 | | $-CH_2-CH_2-O-CH_2-CH_2-OH$ | yellow |
| 448 | 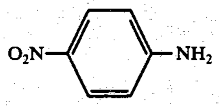 | $-CH_2-CH_2-OH$ | orange |
| 449 | | $-CH_2-CH_2-CH_2-OH$ | orange |
| 450 | | $-CH_2-CH_2-O-(CH_2)_2-OH$ | orange |
| 451 | 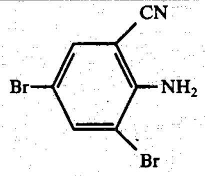 | $-CH_2-CH_2-CH_2-OH$ | orange |
| 452 | | $-CH_2-CH_2-O-CH_2-CH_2-OH$ | orange |
| 453 | 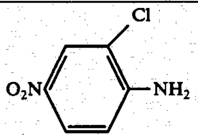 | $-CH_2-CH_2-OH$ | yellowish red |
| 454 | | $-CH_2-CH_2-CH_2-OH$ | yellowish red |
| 455 | 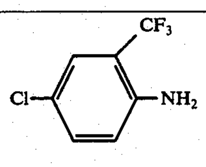 | $-CH_2-CH_2-CH_2-OH$ | yellow |
| 456 | | $-CH_2-CH_2-O-(CH_2)_2OH$ | yellow |
| 457 | 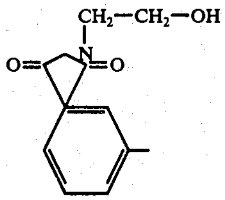 | $-CH_2-CH_2-OH$ | yellow |
| 458 | | $-CH_2-CH_2-CH_2-OH$ | yellow |
| 459 | | $-CH_2-CH_2-CH_2-CH_3$ | yellow |

EXAMPLE 460

19.5 parts of 3-amino-5-nitro-2,1-benzoisothiazole is added in portions while stirring at 15° to 25° C to about 75 to 85 parts of 96% sulfuric acid and the mixture is cooled to 0° to 4° C. 32.5 parts of 23% nitrosylsulfuric acid is then dripped in at this temperature. Diazotization is over after stirring for about three to four hours at 0° to 5° C. The diazonium salt mixture is then added to a solution or suspension, cooled to 0° C, of 34 parts of the coupling component of the formula:

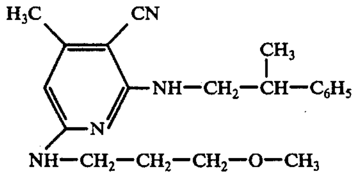

in 50 parts of 30% hydrochloric acid, 500 parts of water and 150 parts of glacial acetic acid. Ice and sodium acetate are added gradually during the coupling so that the temperature of the coupling mixture does not exceed 5° C and the pH finally is about 2. The precipitated dye of the formula:

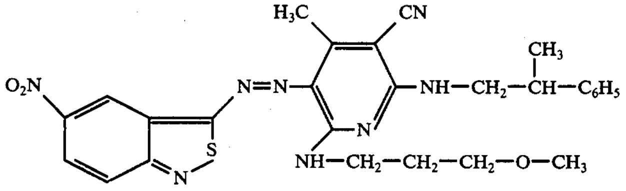

is filtered off, washed with hot water and dried. About 53 parts of a black powder is obtained which dissolves in dimethylformamide with a reddish blue color.

EXAMPLE 461

50 parts of the powder obtained in Example 460 is stirred with about 200 parts of 85 to 95% sulfuric acid for five hours at from 80° to 100° C. The mixture is then poured onto 1500 parts of ice-water, and the precipitated dye of the formula:

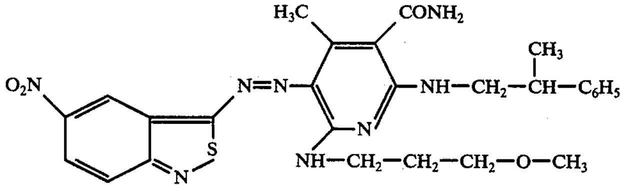

is filtered off, washed with water and dried. About 40 parts of a dark powder is obtained which dissolves in dimethylformamide with a blue color and dyes polyethylene terephthalate cloth blue shades.

Dyes characterized in the following Table by the diazo and coupling components may be obtained by methods analogous to those described above:

TABLE 3

Coupling component:

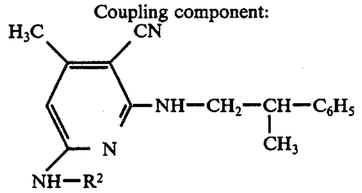

| Example | Diazo component | $R^2$ | Shade |
|---|---|---|---|
| 462 | 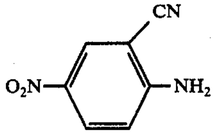 | $-CH_2-CH_2-OH$ | yellowish red |
| 463 | | $-CH_2-CH_2-CH_2-OH$ | yellowish red |
| 464 | | $-CH_2-CH(CH_3)-OH$ | yellowish red |
| 465 | | $-CH_2-CH_2-O-CH_2-CH_2-OH$ | yellowish red |
| 466 | | $-CH_2-CH_2-CH_2-OCHO$ | yellowish red |
| 467 | | H | yellowish red |
| 468 | | $-(CH_2)_6-OH$ | yellowish red |
| 469 | | $-CH_2-CH_2-O-COCH_3$ | yellowish red red |

TABLE 3-continued

Coupling component:

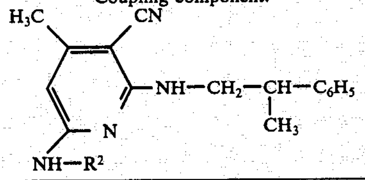

| Example | Diazo component | $R^2$ | Shade |
|---|---|---|---|
| 470 | 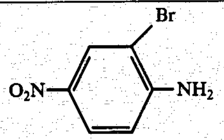 | $-CH_2-CH_2-OH$ | yellowish red |
| 471 | | $-CH_2-CH_2-CH_2-OH$ | yellowish red |
| 472 | | $-CH_2-\underset{CH_3}{\underset{\mid}{CH}}-OH$ | yellowish red |
| 473 | | $-CH_2-CH_2-O-CH_2-CH_2-OH$ | yellowish red |
| 474 | | H | yellowish red |
| 475 | 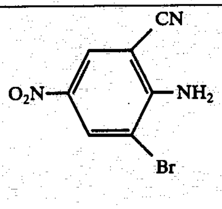 | $-H$ | bluish red |
| 476 | | $-CH_2-CH_2-OH$ | bluish red |
| 477 | | $-CH_2-CH_2-CH_2-OH$ | bluish red |
| 478 | | $-CH_2-\underset{CH_3}{\underset{\mid}{CH}}-OH$ | bluish red |
| 479 | | $-CH_2-CH_2-O-CH_2-CH_2-OH$ | bluish red |
| 480 | | $-CH_2-CH_2-O-CH_3$ | bluish red |
| 481 | | $-CH_2-CH_2-CH_2-O-CH_3$ | bluish red |
| 482 | | $-CH_2-CH_2-O-COCH_3$ | bluish red |
| 483 | 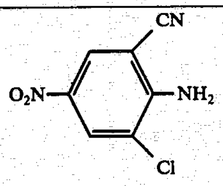 | $-H$ | red |
| 484 | | $-CH_2-CH_2-OH$ | red |
| 485 | | $-CH_2-CH_2-CH_2-OH$ | red |
| 486 | | $-CH_2-\underset{CH_3}{\underset{\mid}{CH}}-OH$ | red |
| 487 | | $-CH_2-CH_2-O-CH_2-CH_2-OH$ | red |
| 488 | | $-CH_2-CH_2-O-CH_3$ | red |
| 489 | | $-C_2H_5$ | red |
| 490 | 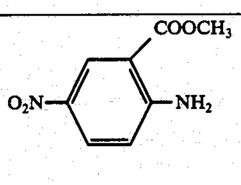 | $-CH_2-CH_2-OH$ | red |
| 491 | | $-CH_2-CH_2-CH_2-OH$ | red |
| 492 | | $-CH_2-CH_2-O-CH_2-CH_2-OH$ | red |
| 493 | 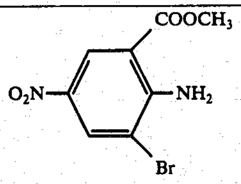 | $-CH_2-CH_2-OH$ | red |
| 494 | | $-CH_2-CH_2-CH_2-OH$ | red |
| 495 | | $-CH_2-CH_2-O-CH_2-CH_2-OH$ | red |

TABLE 3-continued

Coupling component:

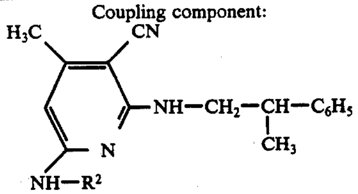

| Example | Diazo component | $R^2$ | Shade |
| --- | --- | --- | --- |
| 496 | 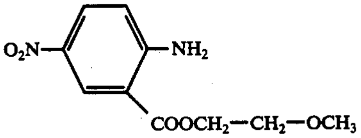 | $-CH_2-CH_2-OH$ | red |
| 497 | | $-CH_2-CH_2-CH_2-OH$ | red |
| 498 | 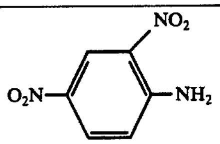 | $-H$ | red |
| 499 | | $-CH_2-CH_2-OH$ | red |
| 500 | | $-CH_2-CH_2-CH_2-OH$ | red |
| 501 | | $-CH_2-CH_2-O-CH_2-CH_2-OH$ | red |
| 502 | | $-CH_2-CH_2-O-CH_3$ | red |
| 503 | 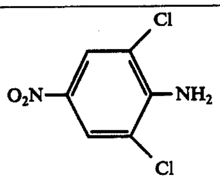 | $-CH_2-CH_2-OH$ | yellowish red |
| 504 | | $-CH_2-CH_2-CH_2-OH$ | yellowish red |
| 505 | | $-CH_2-CH_2-O-CH_2-CH_2-OH$ | yellowish red |
| 506 | | $-CH_2-CH_2-O-COCH_3$ | yellowish red |
| 507 | 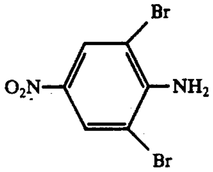 | $-CH_2-CH_2-OH$ | yellowish red |
| 508 | | $-CH_2-CH_2-CH_2-OH$ | yellowish red |
| 509 | | $-CH_2-CH(CH_3)-OH$ | yellowish red |
| 510 | | $-CH_2-CH_2-O-CH_2-CH_2-OH$ | yellowish red |
| 511 | 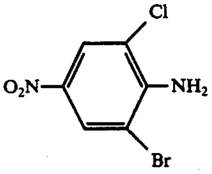 | $-CH_2-CH_2-OH$ | yellowish red |
| 512 | | $-CH_2-CH_2-CH_2-OH$ | yellowish red |
| 513 | | $-CH_2-CH_2-CH_2-O-CH_3$ | yellowish red |
| 514 | 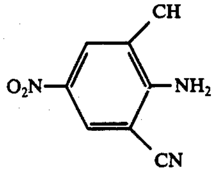 | $-CH_2-CH_2-O-H$ | red |
| 515 | | $-CH_2-CH_2-CH_2-OH$ | bluish red |
| 516 | | $-CH_2-CH_2-O-CH_2-CH_2-OH$ | bluish red |
| 517 | | $-CH_2-CH_2-CH_2-O-CH_2$ | bluish |

TABLE 3-continued

Coupling component:

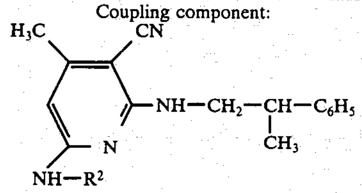

| Example | Diazo component | $R^2$ | Shade |
|---|---|---|---|
| | | | red |
| 518 | 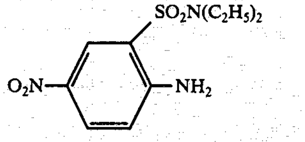 | $-CH_2-CH_2-OH$ | red |
| 519 | | $-CH_2-CH_2-CH_2-OH$ | red |
| 520 | 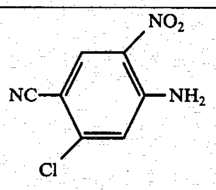 | $-CH_2-CH_2-OH$ | red |
| 521 | | $-CH_2-CH_2-CH_2-OH$ | red |
| 522 | | $-CH_2-CH_2-O-CH_2-CH_2-OH$ | red |
| 523 | 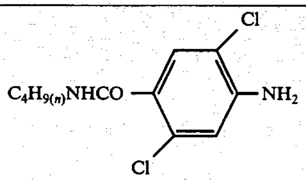 | $-CH_2-CH_2-OH$ | yellow |
| 524 | | $-CH_2-CH_2-CH_2-OH$ | yellow |
| 525 | | $-CH_2-CH_2-O-CH_2-CH_2-OH$ | yellow |
| 526 | 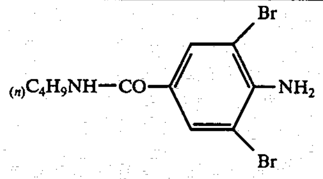 | $-CH_2-CH_2-OH$ | yellow |
| 527 | | $-CH_2-CH_2-CH_2-OH$ | yellow |
| 528 | | $-CH_2-CH_2-O-CH_2-CH_2-OH$ | yellow |
| 529 | 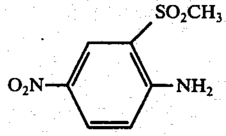 | $-H$ | red |
| 530 | | $-CH_2-CH_2-OH$ | red |
| 531 | | $-CH_2-CH_2-CH_2-OH$ | red |
| 532 | | $-CH_2-CH(CH_3)-OH$ | red |
| 533 | | $-(CH_2)_3-O-(CH_2)_4-OH$ | red |
| 534 | 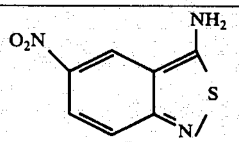 | $-CH_2-CH_2-OH$ | reddish blue |
| 535 | | $-CH_2-CH_2-CH_2-OH$ | reddish blue |
| 536 | | $-CH_2-CH(CH_3)-OH$ | reddish blue |
| 537 | | $-CH_2-CH_2-O-CH_2-CH_2-OH$ | reddish blue |
| | 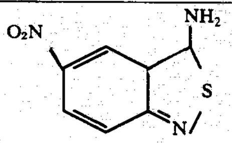 | $-(CH_2)_6-OH$ | reddish blue |
| 539 | | $-(CH_2)_3-O-(CH_2)_4-OH$ | reddish |

TABLE 3-continued

Coupling component:

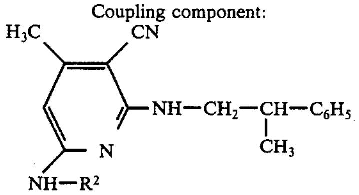

| Example | Diazo component | $R^2$ | Shade |
|---|---|---|---|
| 540 | | $-CH_2-CH_2-CH_2-O-\underset{\underset{O}{\|}}{C}-CH_3$ | blue reddish blue |
| 541 | 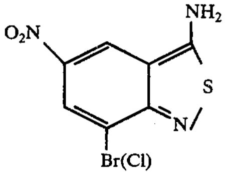 | $-CH_2-CH_2-O-CH_2-CH_2-OH$ | blue |
| 542 | 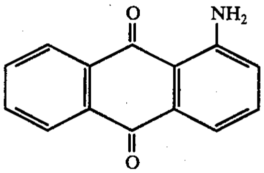 | $-CH_2-CH_2-CH_2-OH$ | yellowish brown |
| 543 | | $-CH_2-CH_2-O-CH_2-CH_2-OH$ | yellowish brown |
| 544 | 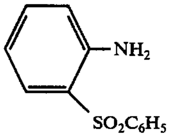 | $-CH_2-CH_2-CH_2-OH$ | yellow |
| 545 | | $-CH_2-CH_2-O-CH_2-CH_2-OH$ | yellow |
| 546 | 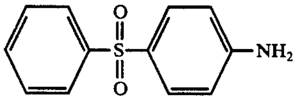 | $-CH_2-CH_2-O-CH_2-CH_2-OH$ | yellow |
| 547 | | $-(CH_2)_3-O-H$ | yellow |
| 548 | 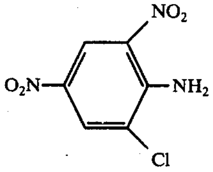 | $-CH_2-CH_2-OH$ | bluish red |
| 549 | | $-CH_2-CH_2-CH_2-OH$ | bluish red |
| 550 | | H | bluish red |
| 551 | | $-CH_2-CH_2-O-CH_2-CH_2-OH$ | bluish red |
| 552 | 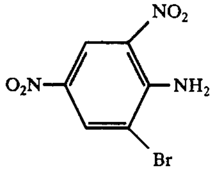 | $-(CH_2)_3-OH$ | bluish red |
| 553 | | $-CH_2-CH_2-O-CH_2-CH_2-OH$ | bluish red |
| 554 | | H | bluish red |
| 555 | 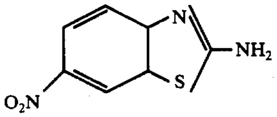 | $-CH_2-CH_2-OH$ | yellowish red |

TABLE 3-continued

Coupling component:

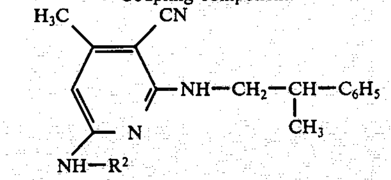

| Example | Diazo component | $R^2$ | Shade |
|---|---|---|---|
| 556 | 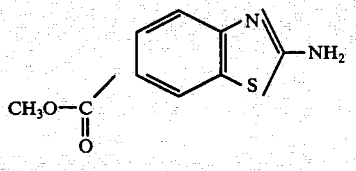 | $-CH_2-CH_2-CH_2-OH$ | yellowish red |
| 557 | | $-CH_2-CH_2-OH$ | yellowish red |
| 558 | 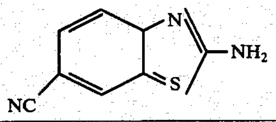 | $-CH_2-CH_2-OH$ | yellowish red |
| 559 | 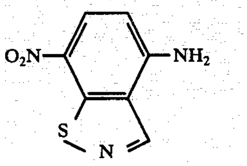 | H | bluish red |
| 560 | | $-CH_2-CH_2-OH$ | bluish red |
| 561 | | $-CH_2-CH_2-CH_2-OH$ | bluish red |
| 562 | | $-CH_2-CH_2-O-CH_2-CH_2-OH$ | bluish red |
| 563 | | $-(CH_2)_3-O-(CH_2)_4-OH$ | bluish red |
| 564 | 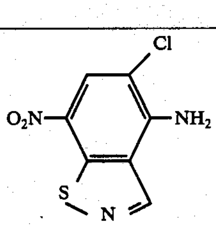 | $-CH_2-CH_2-CH_2-OH$ | violet |
| 565 | | $-CH_2-CH_2-O-CH_2-CH_2-OH$ | violet |
| 566 | | $-H$ | bluish red |
| 567 | 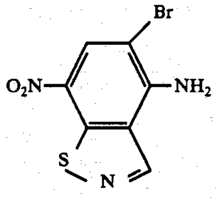 | $-CH_2-CH_2-CH_2-OH$ | violet |
| 568 | | $-CH_2-CH_2-O-CH_2-CH_2-OH$ | violet |
| 569 | 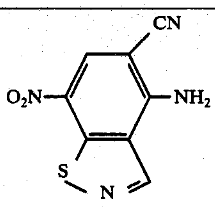 | $-CH_2-CH_2-CH_2-OH$ | violet |
| 570 | | $-CH_2-CH_2-O-CH_2-CH_2-OH$ | violet |
| 571 | 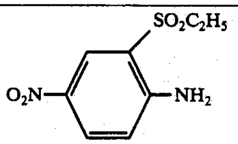 | $-CH_2-CH_2-CH_2-OH$ | red |

TABLE 3-continued

Coupling component:

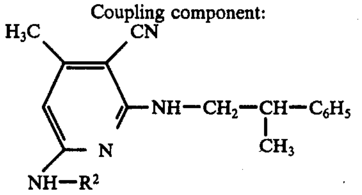

| Example | Diazo component | $R^2$ | Shade |
|---|---|---|---|
| 572 | 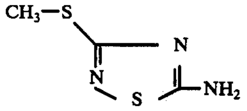 | $-H$ | orange |
| 573 | | $-CH_2-CH_2-OH$ | orange |
| 574 | | $-CH_2-CH_2-CH_2-OH$ | orange |
| 575 | | $-CH_2-CH_2-O-CH_2-CH_2-OH$ | orange |
| 576 | 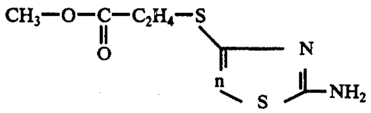 | $-CH_2-CH_2-OH$ | orange |
| 577 | | $-CH_2-CH_2-CH_2-OH$ | orange |
| 578 | | $-CH_2-CH(CH_3)-OH$ | orange |
| 579 | | $-CH_2-CH_2-O-CH_2-CH_2-OH$ | orange |
| 580 | | $-H$ | orange |
| 581 | 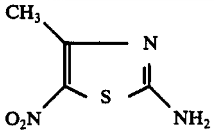 | $-CH_2-CH_2-OH$ | violet |
| 582 | | $-CH_2-CH_2-CH_2-OH$ | violet |
| 583 | | $-CH_2-CH_2-O-CH_2-CH_2-OH$ | violet |
| 584 | 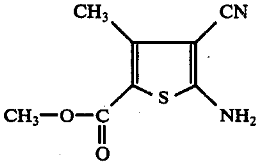 | $-CH_2-CH_2-OH$ | bluish red |
| 585 | | $-CH_2-CH_2-CH_2-OH$ | bluish red |
| 586 | | $-CH_2-CH_2-O-CH_2-CH_2-OH$ | bluish red |
| 587 | | $-CH_2-CH(CH_3)-OH$ | bluish red |
| 588 | 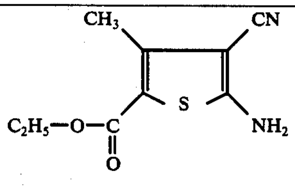 | $-CH_2-CH_2-OH$ | bluish red |
| 589 | | $-CH_2-CH_2-CH_2-OH$ | bluish red |
| 590 | | $-CH_2-CH_2-O-CH_2-CH_2-OH$ | bluish red |
| 591 | 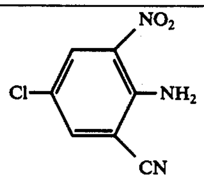 | red | |
| 592 | 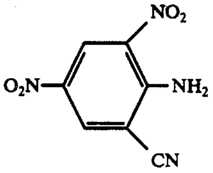 | $-CH_2-CH_2-OH$ | bluish red |
| 593 | | $-CH_2-CH_2-CH_2-OH$ | bluish |

TABLE 3-continued

Coupling component:

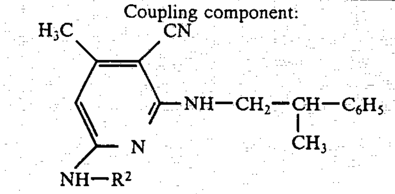

| Example | Diazo component | $R^2$ | Shade |
|---|---|---|---|
| 594 | | H | red bluish red |
| 595 | 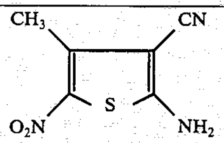 | $-CH_2-CH_2-OH$ | violet |
| 596 | | $-CH_2-CH_2-CH_2-OH$ | violet |
| 597 | 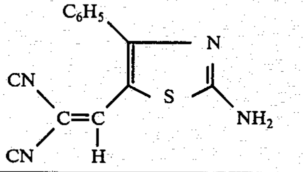 | $-CH_2-CH_2-CH_2-OH$ | reddish blue |

TABLE 4

Coupling component:

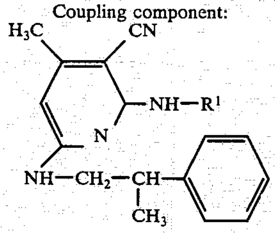

| Example | Diazo component | $R^1$ | Shade |
|---|---|---|---|
| 598 | 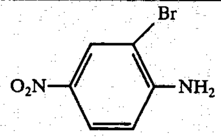 | $-CH_2-CH_2-OH$ | yellowish red |
| 599 | | $-CH_2-CH_2-CH_2-OH$ | " |
| 600 | | $-CH_2-CH_2-O-CH_2-CH_2-OH$ | " |
| 601 | 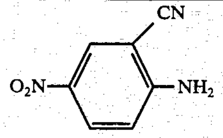 | $-H$ | yellowish red |
| 602 | | $-CH_2-CH_2-OH$ | " |
| 603 | | $-CH_2-CH_2-O-COCH_3$ | " |
| 604 | | $-CH_2-CH_2-CH_2-OH$ | " |
| 605 | | $-CH_2-CH_2-O-CH_2-CH_2-OH$ | " |
| 606 | | $-CH_2-CH_2-O-CH_2-CH_2OCHO$ | " |
| 607 | | $-(CH_2)_6OH$ | " |
| 608 | 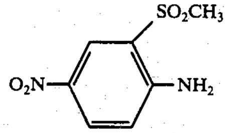 | $-CH_2-CH_2-CH_2-OH$ | red |
| 609 | | $-CH_2-CH_2-OH$ | " |
| 610 | 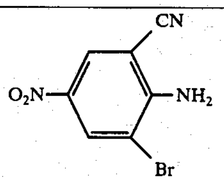 | $-H$ | red |
| 611 | | $-CH_2-CH_2-OH$ | " |
| 612 | | $-CH_2-CH_2-CH_2-OH$ | " |

TABLE 4-continued
Coupling component:
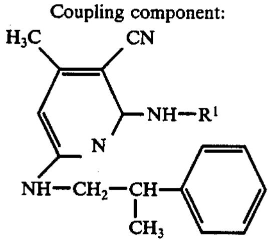
| Example | Diazo component | $R^1$ | Shade |
| --- | --- | --- | --- |
| 613 | | $-CH_2-CH(CH_3)-OH$ | " |
| 614 | | $-CH_2-CH_2-O-CH_2-CH_2-OH$ | " |
| 615 | 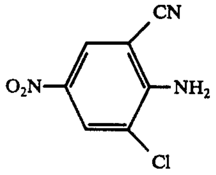 | $-CH_2-CH_2-OH$ | red |
| 616 | | $-CH_2-CH_2-CH_2-OH$ | " |
| 617 | | $-CH_2-CH_2-O-CH_2-CH_2-OH$ | " |
| 618 | | $-(CH_2)_3-O-(CH_2)_4-OH$ | " |
| 619 | 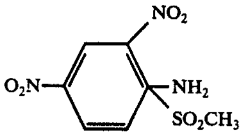 | $-CH_2-CH_2-CH_2-OH$ | violet |
| 620 | 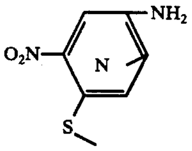 | $-CH_2-CH_2-CH_2-OH$ | red |
| 621 | | $-CH_2-CH_2-O-CH_2-CH_2-OH$ | " |
| 622 | 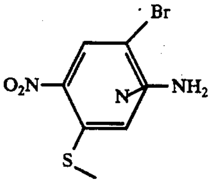 | $-CH_2-CH_2-CH_2-OH$ | violet |
| 623 | | $-CH_2-CH_2-O-CH_2-CH_2-OH$ | " |
| 624 | 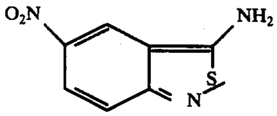 | $-CH_2-CH_2-CH_2-OH$ | reddish blue |
| 625 | | $-CH_2-CH_2-O-CH_2-CH_2-OH$ | " |
| 626 | 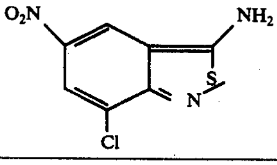 | $-CH_2-CH_2-O-CH_2-CH_2-OH$ | blue |
| 627 | 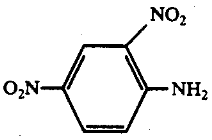 | H | red |
| 628 | | $-CH_2-CH_2-OH$ | red |
| 629 | | $-CH_2-CH_2-CH_2-OH$ | " |
| 630 | | $-CH_2-CH_2-O-CH_2-CH_2-OH$ | " |

TABLE 4-continued

Coupling component:

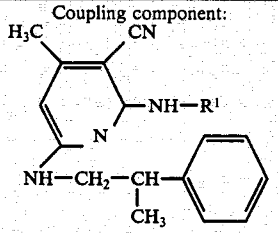

| Example | Diazo component | $R^1$ | Shade |
| --- | --- | --- | --- |
| 631 | 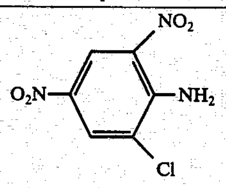 | $-CH_2-CH_2-CH_2-OH$ | bluish red |
| 632 | | $-CH_2-CH_2-O-CH_2-CH_2-OH$ | ″ |
| 633 | 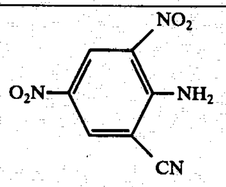 | $-CH_2-CH_2-CH_2-OH$ | bluish red |
| 634 | | $-CH_2-CH_2-O-(CH_2)_2OH$ | ″ |
| 635 | 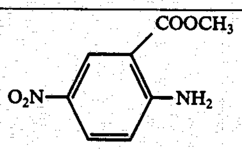 | $-CH_2-CH_2-CH_2-OH$ | red |
| 636 | | $-CH_2-CH_2-O-CH_2-CH_2-OH$ | ″ |

TABLE 5

Coupling component

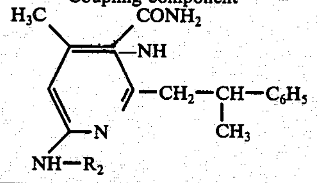

| Example | Diazo component | $R^2$ | Shade |
| --- | --- | --- | --- |
| 637 | 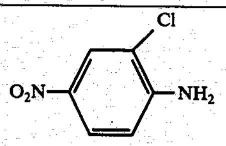 | $-CH_2-CH_2-O-COCH_3$ | red |
| 638 | | $-CH_2-CH_2-CH_2-O-COCH_3$ | ″ |
| 639 | | $-CH_2-CH_2-CH_2-OH$ | ″ |
| 640 | $-CH_2-CH_2-O-CH_3$ | ″ | |
| 641 | 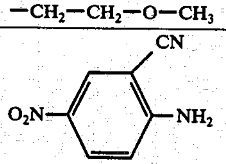 | $-CH_2-CH_2-OCOCH_3$ | bluish red |
| 642 | | $-CH_2-CH_2-CH_2-OCOCH_3$ | ″ |
| 643 | | $-CH_2-CH_2-CH_2-OH$ | ″ |
| 644 | | $-CH_2-CH_2-O-CH_2-CH_2-OCOCH_3$ | ″ |
| 645 | | $-CH_2-CH_2-O-CH_2-CH_2-OH$ | ″ |
| 646 | | $-CH_2-CH_2-O-CH_3$ | ″ |
| 647 | 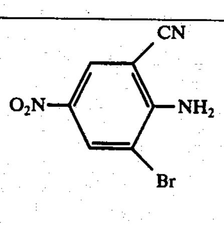 | $-CH_2-CH_2-CH_2-OCOCH_3$ | red violet |
| 648 | | $-CH_2-CH_2-CH_2-OH$ | ″ |
| 649 | | $-CH_2-CH_2-O-CH_2-CH_2-OCOCH_3$ | ″ |

TABLE 5-continued

Coupling component

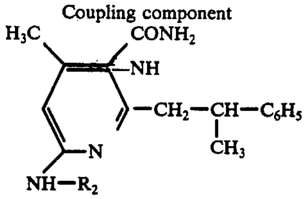

| Example | Diazo component | $R^2$ | Shade |
|---|---|---|---|
| 650 | | $-CH_2-CH_2-O-CH_2-CH_2-OH$ | " |
| 651 | | $-CH_2-CH_3$ | " |
| 652 | | $-CH_2-CH_2-CH_2-O-CH_3$ | " |
| 653 | 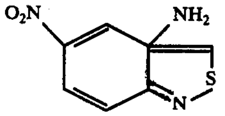 | $-CH_2-CH_2-O-COCH_2-COCH_3$ | blue |
| 654 | | $-CH_2-CH_2-OCOCH_3$ | |
| 655 | | $-CH_2-CH_2-CH_2-O-COCH_3$ | " |
| 656 | | $-CH_2-CH_2-CH_2-OH$ | " |
| 657 | | $-CH_2-CH_2-O-CH_3$ | " |
| 658 | | $-CH_2-CH_2-CH_2-O-C_2H_5$ | " |
| 659 | | $-CH_2-CH_2-O-CH_2-CH_2-OCHO$ | " |
| 660 | | $-CH_2-CH_2-O-CH_2-CH_2-OH$ | " |
| 661 | | $-CH_2-CH_O-CH_2-CH_2-O-COCH_3$ | " |
| 662 | 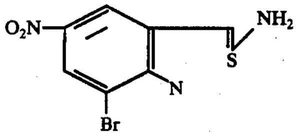 | $-CH_2-CH_2-O-CH_2-CH_2-O-COCH_3$ | greenish blue |

TABLE 6

Coupling component:

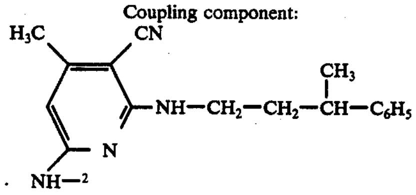

| Example | Diazo component | $R^2$ | Shade |
|---|---|---|---|
| 663 | 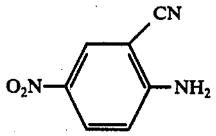 | H | yellowish red |
| 664 | | $-CH_2-CH_2-OH$ | red |
| 665 | | $-CH_2-CH_2-CH_2-OH$ | red |
| 666 | | OH<br>$-CH_2-CH$<br>$CH_3$ | yellowish red |
| 667 | | $-CH_2-CH_2-O-CH_2-CH_2-OH$ | yellowish red |
| 668 | 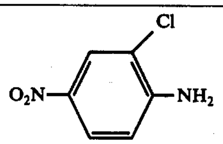 | H | yellowish red |
| 669 | | $-CH_2-CH_2-OH$ | yellowish red |
| 670 | | $-CH_2-CH_2-CH_2-OH$ | yellowish red |
| 671 | | $-CH_2-CH_2-O-CH_2-CH_2-OH$ | yellowish red |
| 672 | 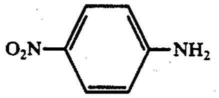 | H | orange |
| 673 | | $-CH_2-CH_2-OH$ | orange |
| 674 | | $-CH_2-CH_2-CH_2-OH$ | orange |
| 675 | | $-CH_2-CH_2-O-CH_2-CH_2-OH$ | orange |

TABLE 6-continued

Coupling component:

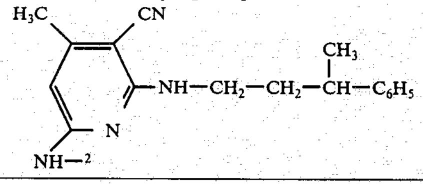

| Example | Diazo component | $R^2$ | Shade |
|---|---|---|---|
| 676 | 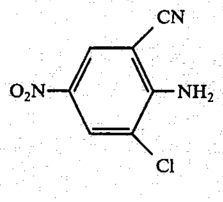 | H | bluish red |
| 677 | | $-CH_2-CH_2-OH$ | red |
| 678 | | $-CH_2-CH_2-CH_2-OH$ | red |
| 679 | 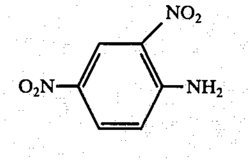 | H | red |
| 680 | | $-CH_2-CH_2-OH$ | red |
| 681 | | $-CH_2-CH_2-CH_2-OH$ | red |
| 682 | 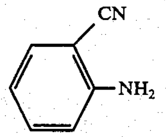 | H | yellow |
| 683 | | $-CH_2-CH_2-OH$ | yellow |

The further diazo components of Examples 345 to 662 give with the coupling components of the formula above Table 6 on page 46 dyes which have only negligible differences from the corresponding dyes with the 2-phenylpropylamine radical.

EXAMPLE 684

A mixture of 187 parts of 2,6-dichloro-3-cyano-4-methylpyridine, 150 parts of triethylamine, 200 parts of isopropanol and 160 parts of 2-amino-6-methylheptanol-(6) is stirred for eight hours at about 55° to 80° C. The mixture is then allowed to cool and is poured with stirring into about 1500 parts of water, 200 parts of concentrated hydrochloric acid and 200 parts of ice. The whole is further stirred for another hour, the oil of the probable formula:

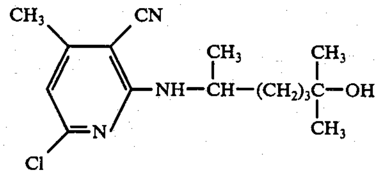

which separates is decanted and washed with water. The oil contains a minor amount of 2-chloro-3-cyano-4-methyl-6-aminoheptanolpyridine isomer.

15 parts of the oil is stirred with 40 parts of β-hydroxy-ethylamine for 6 hours at 145°-160° C, allowed to cool, mixed with 100 parts of water and acidified with hydrochloric acid to a pH of about 0 to 1. After any necessary addition of some glacial acetic acid or dimethylformamide, a solution of the coupling component of the probable formula:

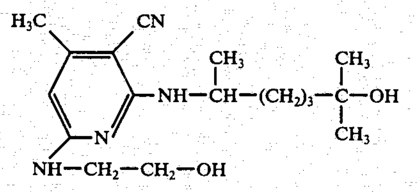

is obtained which contains a minor amount of the 2,6-dialkylamino isomer.

The solution of this coupling is cooled to 0 to 3° C by adding ice and a diazonium salt solution is added which has been obtained as follows: 6.9 parts of p-nitroaniline has added to it about 30 parts of concentrated hydrochloric acid (30%) and 80 parts of water, then the mixture is cooled to 0° C and 15 parts by volume of 23% sodium nitrate solution is added in portions. Stirring is continued for another two hours, any excess of nitrous acid present is removed as usual and filtration carried out.

The filtrate is added to the coupling mixture; then such an amount of sodium acetate or caustic soda solution is gradually added while stirring that the pH of the coupling mixture is from about 2 to 3. If the mixture is difficult to stir, ice-water may be added. When coupling is over the mixture is heated to 70° to 80° C, filtered, and the residue washed with water and dried. About 20 parts of a brown powder is obtained which probably has the formula:

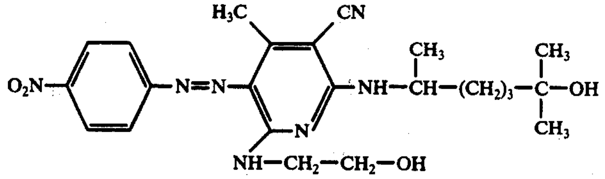

(the dye contains a minor proportion of the 2,6-dialkylaminopyridine isomer). It dissolves in dimethylformamide with an orange color and dyes polyethylene terephthalate cloth full, clear orange shades having outstanding fastness properties.

The following dyes characterized by the diazo and coupling components are obtained analogously to the methods described.

TABLE 1

Coupling component:

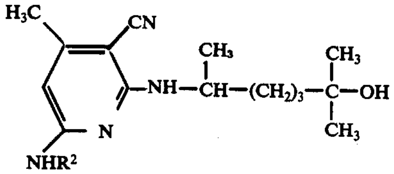

| Example | Dizo component | $R^2$ | Shade |
|---|---|---|---|
| 685 | 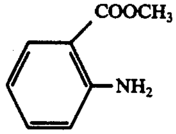 | H | yellow |
| 686 | | $-CH_2-CH_2-OH$ | yellow |
| 687 | | $-CH_2-CH_2-CH_2-OH$ | yellow |
| 688 | | $-CH_2-CH(CH_3)-OH$ | yellow |
| 689 | 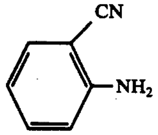 | H | yellow |
| 690 | | $-CH_2-CH_2OH$ | yellow |
| 691 | $-CH_2-CH_2-CH_2-OH$ | yellow | |
| 692 | | 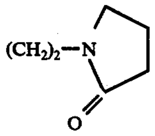 | yellow |
| 693 | | 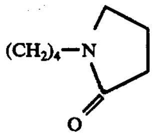 | yellow |
| 694 | 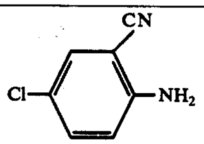 | $-H$ | yellow |
| 695 | | $-CH_2-CH_2-OH$ | yellow |
| 696 | | $-CH_2-CH_2-CH_2-OH$ | yellow |
| 697 | | 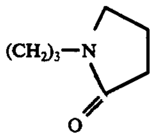 | yellow |
| 698 | | 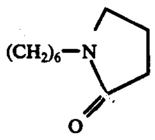 | |

TABLE 1-continued

Coupling component:

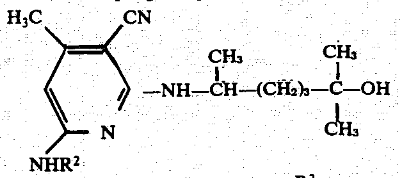

| Example | Dizo component | $R^2$ | Shade |
|---|---|---|---|
| 699 | 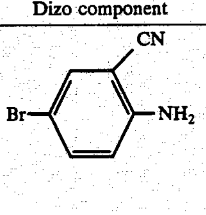 | —H | yellow |
| 700 | | $-CH_2-CH_2-OH$ | yellow |
| 701 | | $-CH_2-CH_2-CH_2-OH$ | yellow |
| 702 | | $-CH_2-CH_2-CH-CH_3$<br>$CH_3$ | yellow |
| 703 | | 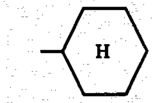 | yellow |
| 704 | 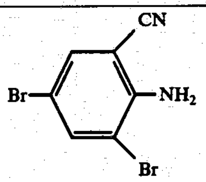 | H | orange |
| 705 | | $-CH_2-CH_2-OH$ | orange |
| 706 | | $-CH_2-CH_2-OH$ | orange |
| 707 | | $-CH_2-CH-OH$<br>$CH_3$ | orange |
| 708 | 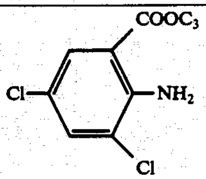 | H | oange |
| 709 | | $-CH_2-CH-OH$ | oragne |
| 710 | | $-CH_2-CH_2-OH$ | orange |
| 711 | 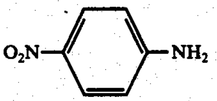 | H | orange |
| 712 | | 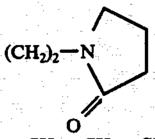 | orange |
| 713 | | $-CH_2-CH_2-CH_2-OCOCH_3$ | orange |
| 714 | | 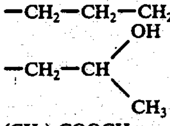 | orange |
| 715 | | $(CH_2)_5COOCH_3$ | orange |
| 716 | | $-CH_2-CH_2-O-CH_3$ | orange |
| 717 | | $-CH_2-CH_2-CH_2-O-CH_3$ | orange |
| 718 | | $-CH_2-CH_2OCHO$ | orange |
| 719 | | $-(CH_2)_6-OH$ | orange |
| 720 | 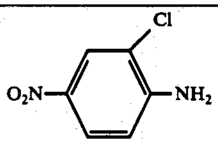 | —H | yellowish red |
| 721 | | $-CH_2-CH_2-OH$ | yellowish red |
| 722 | | $-CH_2-CH_2-CH_2-OH$ | yellowish red |

TABLE 1-continued

Coupling component:

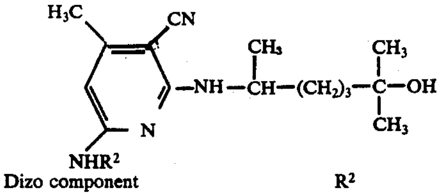

| Example | Dizo component | $R^2$ | Shade |
|---|---|---|---|
| 723 | | 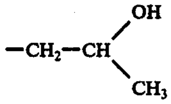 | yellowish red |
| 724 | | $-CH_2-CH_2-CH_2-O-CH_3$ | yellowish red |
| 725 | 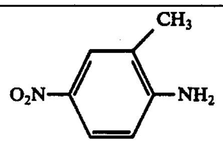 | $-CH_2-CH_2-OH$ | yellowish red |
| 726 | | $-CH_2-CH_2-CH_2-OH$ | yellowish red |
| 727 | 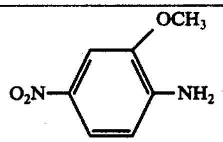 | $-CH_2-CH_2-OH$ | yellowish red |
| 728 | | $-CH_2-CH_2-CH_2-OH$ | yellowish red |
| 729 | 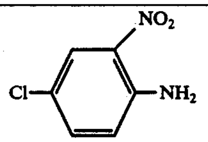 | $-CH_2-CH_2-OH$ | orange |
| 730 | | $-CH_2-CH_2-CH_2-OH$ | orange |
| 731 | 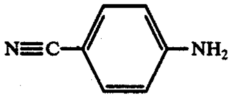 | $-CH_2-CH_2-OH$ | yellow |
| 732 | | $-CH_2-CH_2-CH_2-OH$ | yellow |
| 733 | 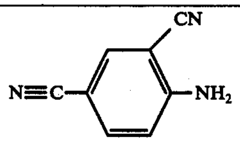 | $-CH_2-CH_2-OH$ | orange |
| 734 | | $-CH_2-CH_2-CH_2-OH$ | orange |
| 735 | 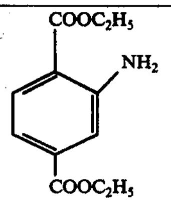 | $-CH_2-CH_2-OH$ | yellow |
| 736 | | $-CH_2-CH_2-CH_2-OH$ | yellow |
| 737 | 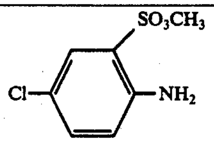 | H | yellow |
| 738 | | $-CH_2-CH_2-OH$ | yellow |
| 739 | | $-CH_2-CH_2-CH_2-OH$ | yellow |
| 740 | | $-CH_2-CH_2-CH_2-O-CH_3$ | |
| 741 | 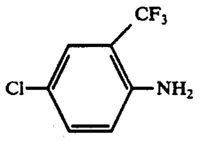 | $-CH_2-CHk_2-OH$ | yellow |
| 742 | | $-CH_2-CH_2-CH_2-OH$ | yellow |

TABLE 1-continued

Coupling component:

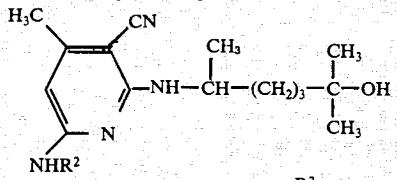

| Example | Dizo component | $R^2$ | Shade |
| --- | --- | --- | --- |
| 743 | 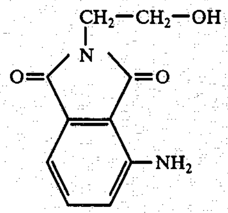 | —H | yellow |
| 744 | | $-CH_2-CH_2-OH$ | yellow |
| 745 | | $-CH_2-CH_2-OH$ | yellow |
| 746 | | $(CH_2)_5COCH$ | yellow (polyamide) |
| 747 | | $-CH_2-CH_2-O-CH_3$ | yellow |
| 748 | 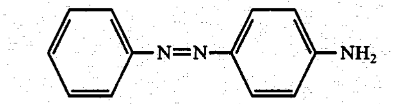 | $-CH_2-CH_2-CH_2-OH$ | yellowish red |
| 749 | | $-CH_2-CH_2-OH$ | yellowish red |
| 750 | 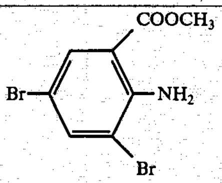 | $-CH_2-CH_2-CH_2-OH$ | orange |
| 751 | 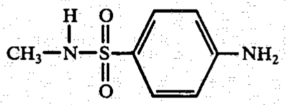 | | |
| 752 | | $-CH_2-CH_2-CH_2-OH$ | yellow |
| 753 | 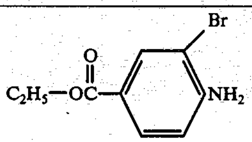 | $-CH_2-CH_2-OH$ | yellow |
| 754 | | $-CH_2-CH_2-CH_2-OH$ | yellow |
| 755 | | 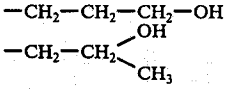 | yellow |
| 756 | 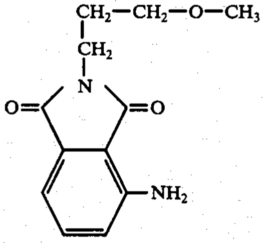 | $-CH_2-CH_2-OH$ | yellow |
| 757 | 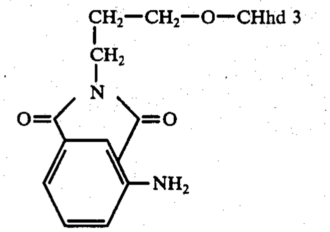 | $-CH_2-CH_2-OH$ | yellow |
| 758 | | $-CH_2-CH_2-CH_2-OH$ | yellow |
| | | $(CH_2)_5COOH$ | yellow (polyamide) |

TABLE 1-continued

Coupling component:

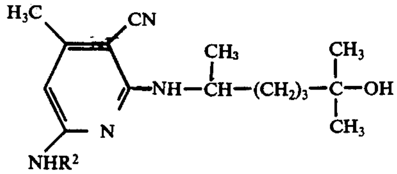

| Example | Dizo component | $R^2$ | Shade |
|---|---|---|---|
| 759 | 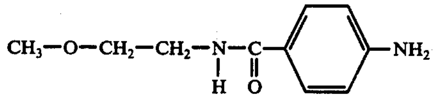 | $-CH_2-CH_2-OH$ | yellow |
| 760 | | $-CH_2-CH_2-CH_2-OH$ | yellow |
| 761 | 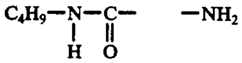 | $-CH_2-CH_2-OH$ | yellow |
| 762 | | $-CH_2-CH_2-CH_2-OH$ | yellow |

TABLE 2

Coupling component:

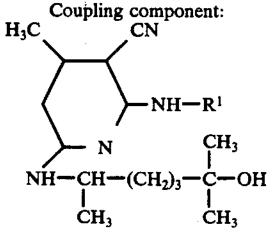

| Example | Diazo component | $R^1$ | Shade |
|---|---|---|---|
| 763 | 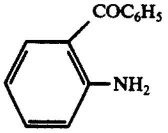 | $-CH_2-CH_2-OH$ | yellow |
| 764 | | $-CH_2-CH_2-CH_2-OH$ | yellow |
| 765 | 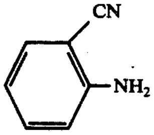 | $-H$ | yellow |
| 766 | | $-CH_2-CH_2-OH$ | yellow |
| 767 | | $-CH_2-CH_2-CH_2-OH$ | yellow |
| 768 | 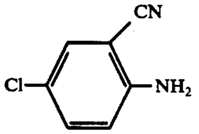 | $-CH_2-CH_2-OH$ | yellow |
| 769 | 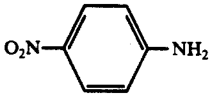 | $-CH_2-CH_2-OH$ | orange |
| 770 | | $-CH_2-CH_2-CH_2-OH$ | orange |
| 771 | 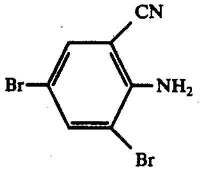 | $-CH_2-CH_2-CH_2-OH$ | orange |
| 772 | 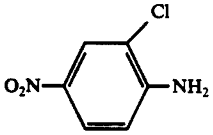 | $-CH_2-CH_2-OH$ | yellowish red |
| 773 | | $-CH_2-CH_2-CH_2-OH$ | yellowish red |

TABLE 2-continued

Coupling component:

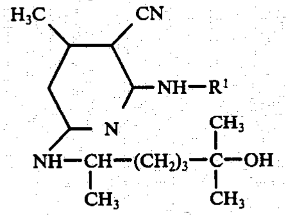

| Example | Diazo component | $R^1$ | Shade |
|---|---|---|---|
| 774 | 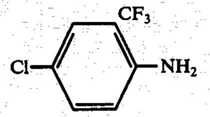 | $-CH_2-CH_2-CH_2-OH$ | yellow |
| 775 | 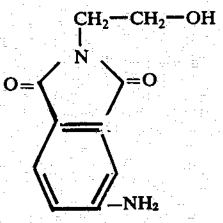 | $-CH_2-CH_2-OH$ | yellow |
| 776 | | $-CH_2-CH_2-CH_2-OH$ | yellow |
| 777 | | $-CH_2-CH_2-CH_2-CH_3$ | yellow |

EXAMPLE 778

19.5 parts of 3-amino-5-nitro-2,1-benzoisothiazole is added in portions while stirring at 15° to 25° C to about 75 to 85 parts of 96% sulfuric acid and the mixture is then cooled to 0° to 4° C. Then 32.5 parts of 23% nitrosylsulfuric acid is dripped in at this temperature. Diazotization is ended after stirring for from about three to four hours at 0° to 5° C. The diazonium salt mixture is then added to a solution or suspension, cooled to 0° C, of 34.9 parts of the coupling component of the formula:

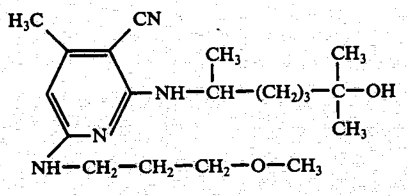

in 50 parts of 30% hydrochloric acid, 500 parts of water and 150 parts of glacial acetic acid. During coupling, ice and sodium acetate are added at intervals so that the temperature of the coupling mixture does not rise above 5° C and the pH is finally about 2. The precipitated dye of the formula:

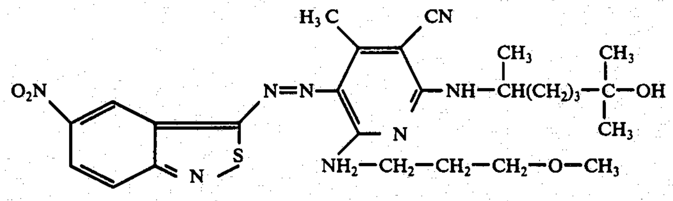

is filtered off, washed with hot water and dried. About 53.6 parts of a black powder is obtained which dissolves in dimethylformamide with a reddish blue color.

EXAMPLE 779

21.6 parts of 2-amino-5-nitrobenzenemethylsulfone-(1) is stirred at from 10° to 15° C in 100 parts of 96% sulfuric acid. Then 32.5 parts of 23% nitrosylsulfuric acid is added at 0° to 5° C and the mixture is stirred for four hours at 5° to 10° C. The diazonium salt solution obtained is allowed to flow within about twenty minutes into 35.5 parts of a suspension, cooled to 0° C, of the coupling component of the formula:

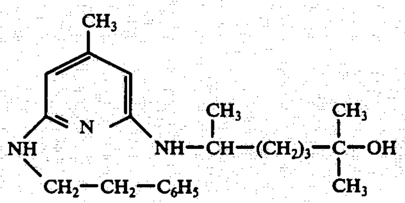

in a mixture of 100 parts of glacial acetic acid, 1 part of sulamic acid, 30 parts by volume of concentrated hydrochloric acid and 500 parts of water. During coupling the mixture is kept at pH 0 to 2 by adding sodium acetate, and water and ice are added for better stirring.

After coupling has ended (having proceeded at above pH 2) the dye mixture of the formulae:

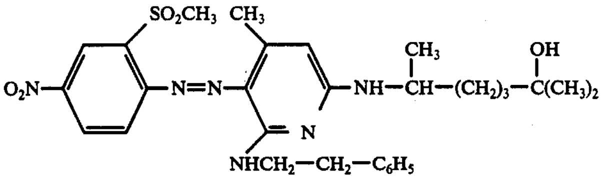

and

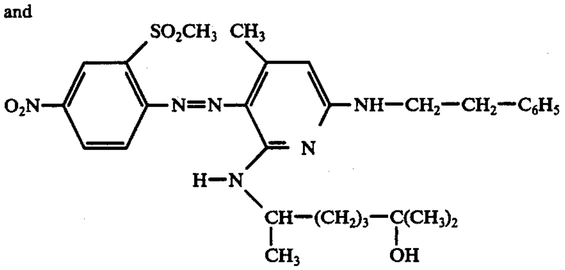

is suction filtered, washed with water and dried. A dark powder is obtained which dissolves in dimethylformamide with a reddish violet color and dyes polyethylene terephthalate cloth reddish violet shades.

TABLE 3

| Coupling component: | | | |
|---|---|---|---|
| 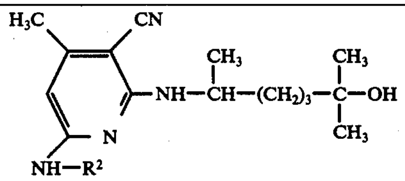 | | | |
| Example | Diazo component | $R^2$ | Shade |
| 780 | 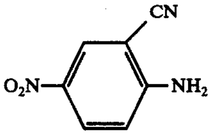 | $-CH_2-CH_2-OH$ | yellowish red |
| 781 | | $-CH_2-CH_2-CH_2-OH$ | yellowish red |
| 782 | | $-CH_2-CH(CH_3)-OH$ | yellowish red |
| 783 | | $-CH_2-CH_2-CH_2-OCHO$ | yellowish red |
| 784 | H | yellowish red | |
| 785 | | $-(CH_2)_6-OH$ | yellowish red |
| 786 | | $-CH_2-CH_2-O-COCH_3$ | yellowish red |
| 787 | 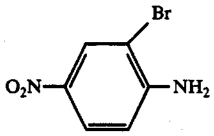 | $-CH_2-CH_2-OH$ | yellowish red |
| 788 | | $-CH_2-$CH hd 2$-CH_2-OH$ | yellowish red |
| 789 | | $-CH_2-CH(CH_3)-OH$ | yellowish red |
| 790 | | H | yellowish red |
| 791 | 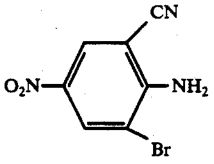 | $-H$ | red |
| 792 | | $-CH_2-CH_2-OH$ | red |
| 793 | | $-CH_2-$CH hd 2$-CH_2-OH$ | red |
| 794 | | $-CH_2-CH(CH_3)-OH$ | red |
| 795 | | $-CH_2-CH_2-O-CH_3$ | red |
| 796 | | $-CH_2-CH_2-CH_2-O-CH_3$ | red |
| 797 | | $-CH_2-CH_2-O-COCH_3$ | red |

TABLE 3-continued

Coupling component:

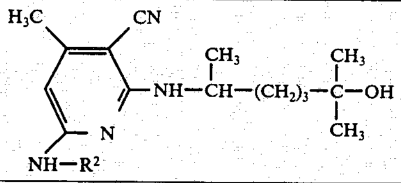

| Example | Diazo component | $R^2$ | Shade |
|---|---|---|---|
| 798 | 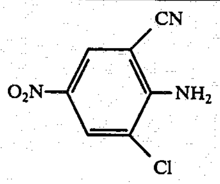 | $-H$ | red |
| 799 | | $-CH_2-CH_2-OH$ | red |
| 800 | | $-CH_2-CH_2-CH_2-OH$ | red |
| 801 | | $-CH_2-CH(CH_3)-OH$ | red |
| 802 | 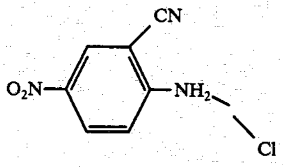 | $-CH_2-CH_2-O-CH_3$ | red |
| 803 | | $-C_2H_5$ | red |
| 804 | 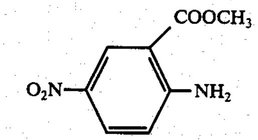 | $-CH_2-CH_2-OH$ | red |
| 805 | | $-CH_2-CH_2-CH_2-OH$ | red |
| 806 | 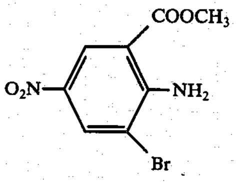 | $-CH_2-CH_2-OH$ | red |
| 807 | | $-CH_2-CH_2-CH_2-OH$ | red |
| 808 | 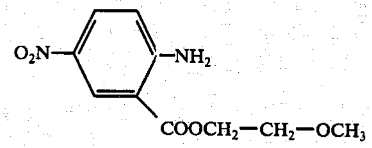 | $-CH_2-CH_2-OH$ | red |
| 809 | | $-CH_2-CH_2-CH_2-OH$ | red |
| 810 | 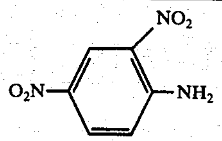 | $-H$ | red |
| 811 | | $-CH_2-CH_2-OH$ | red |
| 812 | | $-CH_2-CH_2-CH_2-OH$ | red |
| 813 | | $-CH_2-CH_2-O-CH_3$ | red |
| 814 | 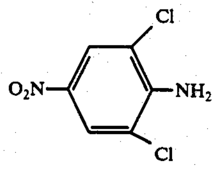 | $-CH_2-CH_2-OH$ | yellowish red |
| 815 | | $-CH_2-CH_2-CH_2-OH$ | yellowish red |
| 816 | | $-CH_2-CH_2-O-COCH_3$ | yellowish red |

TABLE 3-continued

Coupling component:

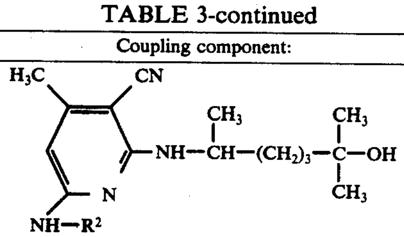

| Example | Diazo component | $R^2$ | Shade |
|---|---|---|---|
| 817 | 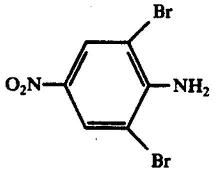 | $-CH_2-CH_2-CH_2-OH$ | yellowish red |
| 818 | | $-CH_2-CH_2-CH_2-OH$ | yellowish red |
| 819 | | 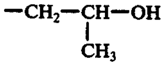 | yellowish red |
| 820 | 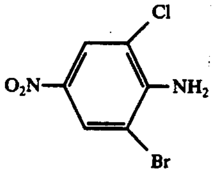 | $-CH_2-CH_2-OH$ | yellowish red |
| 821 | | $-CH_2-CH_2-CH_2-OH$ | yellowish red |
| 822 | | $-CH_2-CH_2-CH_2-O-CH_3$ | yellowish red |
| 823 | 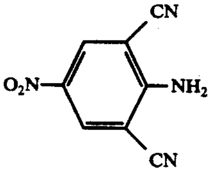 | $-CH_2-CH_2-O-H$ | bluish red |
| 864 | | $-CH_2-CH_2-CH_2-OH$ | orange |
| 865 | 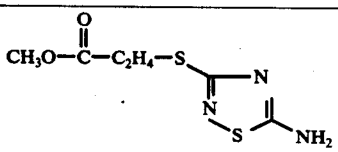 | $-CH_2-CH_2-OH$ | orange |
| 866 | | $-CH_2-CH_2-CH_2-OH$ | orange |
| 867 | | 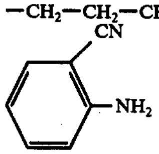 | orange |
| 868 | | $-H$ | orange |
| 869 | 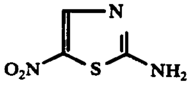 | $-CH_2-CH_2-OH$ | violet |
| 870 | | $-CH_2-CH_2-CH_2-OCH_3$ | violet |
| 871 | 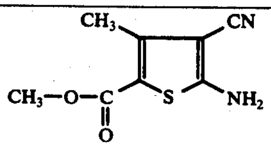 | $-CH_2-CH_2-OH$ | bluish red |
| 872 | | $-CH_2-CH_2-CH_2-OH$ | bluis red |
| 873 | | 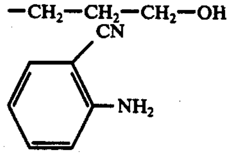 | bluish red |
| 874 | 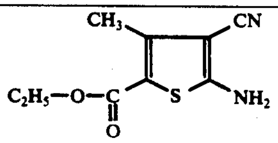 | $-CH_2-CH_2-OH$ | bluish red |

TABLE 3-continued

Coupling component:

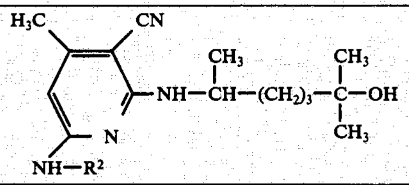

| Example | Diazo component | $R^2$ | Shade |
|---|---|---|---|
| 875 | | $-CH_2-CH_2-CH_2-OH$ | bluish red |
| 876 | 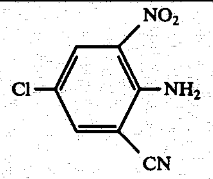 | $-CH_2-CH_2-CH_2-OH$ | yellowish red |
| 877 | 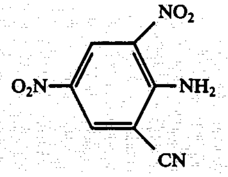 | $-CH_2-CH_2-OH$ | bluish red |
| 878 | | $-CH_2-CH_2-CH_2-OH$ | bluish red |
| 879 | | H | bluish red |
| 880 | 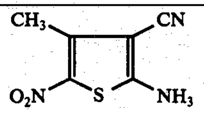 | $-CH_2-CH_2-OH$ | violet |
| 881 | | $-CH_2-CH_2-CH_2-OH$ | violet |
| 882 | 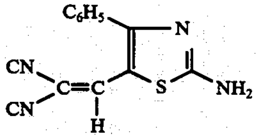 | $-CH_2-CH_2-CH_2-OH$ | blue |

TABLE 4

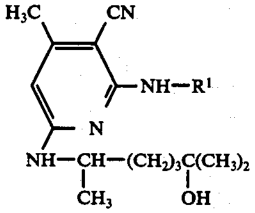

Coupling component:

| Example | Diazo component | $R^1$ | Shade |
|---|---|---|---|
| 883 | 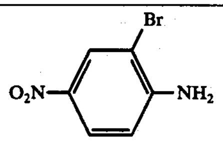 | $-CH_2-CH_2-OH$ | yellowish red |
| 884 | | $-CH_2-CH_2-CH_2-OH$ | " |
| 885 | 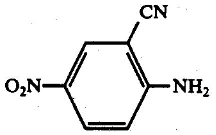 | $-H$ | yellowish red |
| 886 | | $-CH_2-CH_2-OH$ | " |
| 887 | | $-CH_2-CH_2-O-COCH_3$ | " |
| 888 | | $-CH_2-CH_2-CH_2-OH$ | " |
| 889 | | $-CH_2-CH_2-O-CH_2-CH_2-OCHO$ | " |
| 890 | | $-(CH_2)_6OH$ | " |

Best Available Copy
TABLE 4-continued
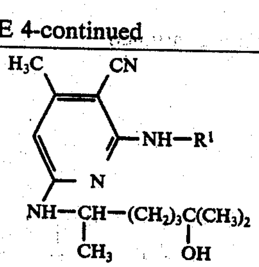
Coupling component:
| Example | Diazo component | $R^1$ | Shade |
|---|---|---|---|
| 891 | 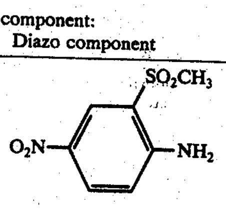 | $-CH_2-CH_2-CH_2-OH$ | red |
| 892 | | $-CH_2-CH_2-OH$ | " |
| 893 | 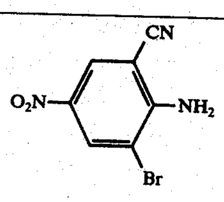 | $-H$ | red |
| 894 | | $-CH_2-CH_2-OH$ | " |
| 895 | | $-CH_2-CH_2-CH_2-OH$ | " |
| 896 | 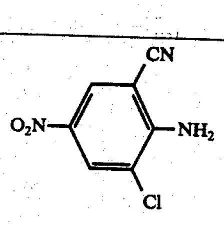 | $-H$ | red |
| 897 | | $-CH_2-CH_2-OH$ | " |
| 898 | | $-CH_2-CH_2-CH_2-OH$ | " |
| 899 | 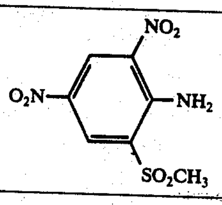 | $-CH_2-CH_2-CH_2-OH$ | violet |
| 900 | 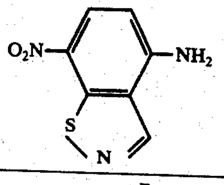 | $-CH_2-CH_2-CH_2-OH$ | red |
| 901 | 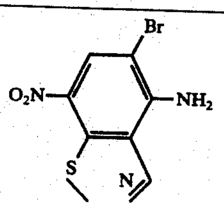 | $-CH_2-CH_2-CH_2-OH$ | violet |
| 902 | 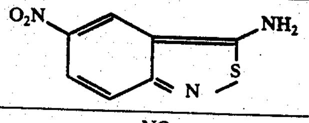 | $-CH_2-CH_2-CH_2-OH$ | reddish blue |
| 903 | 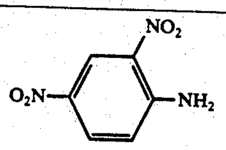 | H | red |
| 904 | | $-CH_2-CH_2-OH$ | " |
| 905 | | $-CH_2-CH_2-CH_2-OH$ | " |

Best Available Copy

TABLE 4-continued

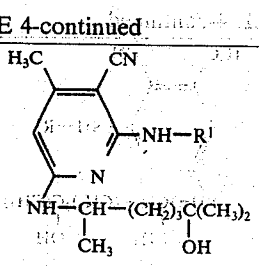

| Coupling component: Example | Diazo component | $R^1$ | Shade |
|---|---|---|---|
| 906 | 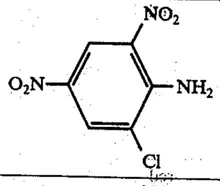 | $-CH_2-CH_2-CH_2-OH$ | bluish red |
| 907 | 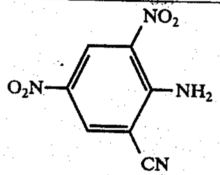 | $-CH_2-CH_2-CH_2-OH$ | bluish red |
| 908 | 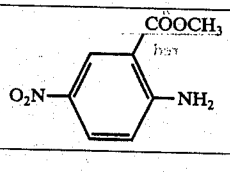 | $-CH_2-CH_2-CH_2-OH$ | red |

TABLE 5

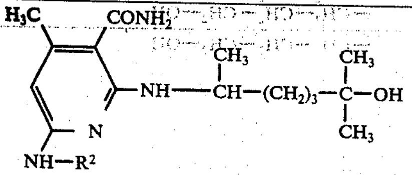

| Coupling component: Example | Diazo component | $R^2$ | Shade |
|---|---|---|---|
| 909 | 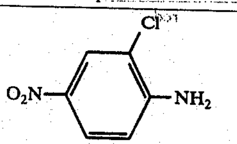 | $-CH_2-CH_2-OH$ | red |
| 910 | | $CH_2-CH_2-CH_2-O-CH_3$ | " |
| 911 | | $-CH_2-CH_2-CH_2-OH$ | " |
| 912 | | $-CH_2-CH_2-O-CH_3$ | " |
| 913 | 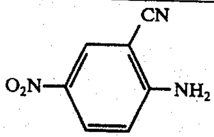 | $-CH_2-CH_2-OH$ | bluish red |
| 914 | | $-CH_2-CH_2-CH_2-OH$ | " |
| 915 | | $-CH_2-CH_2-C_6H_5$ | " |
| 916 | | $-CH_2-CH_2-CH_2-O-CH_3$ | " |
| 917 | | $-C_2H_5$ | " |
| 918 | 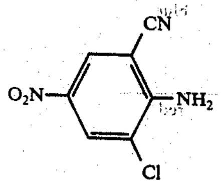 | $-CH_2-CH_2-OH$ | red violet |
| 919 | | $-(CH_2)_3-OH$ | " |
| 920 | | $-C_2H_4-OCH_3$ | " |
| 921 | | $-C_2H_5$ | " |

TABLE 5-continued

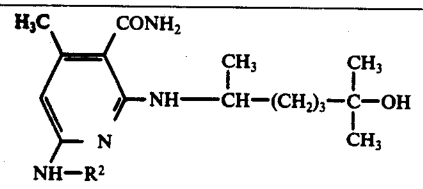

Coupling component:

| Example | Diazo component | $R^2$ | Shade |
|---|---|---|---|
| 922 | 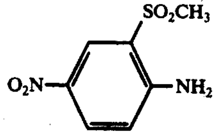 | $-CH_2-CH_2-OH$ | red violet |
| 923 | | $-(CH_2)_3-OH$ | " |
| 924 | | $-C_2H_5$ | " |
| 925 | 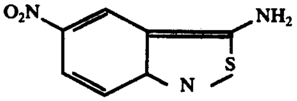 | $-(CH_2)_3-OH$ | blue |
| 926 | | $-C_3H_6-OCH_3$ | " |
| 927 | 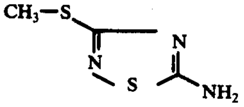 | $-(CH_2)_3-OH$ | yellowish red |
| 928 | | $-CH_2-CH_2-CH_2-OCH_3$ | " |
| 929 | | $-C_3H_7(n)$ | " |
| 930 | 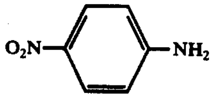 | $-CH_2-CH_2-OH$ | yellowish red |
| 931 | | $-(CH_2)_3-OH$ | " |
| 932 | | $-C_6H_5$ | red |
| 933 | 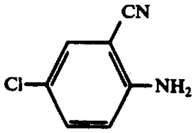 | $-CH_2-CH_2-OH$ | orange |
| 934 | | $-CH_2-CH_2-CH_2-OH$ | " |

TABLE 6

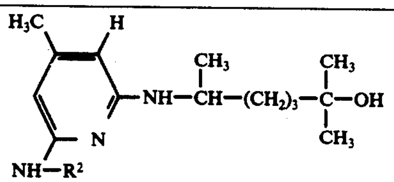

Coupling component:

| Example | Diazo component | $R^2$ | Shade |
|---|---|---|---|
| 935 | 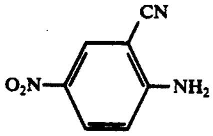 | $-CH_2-CH_2-C_6H_5$ | yellowish red |
| 936 | | $-CH_2-CH_2-OH$ | red |
| 937 | | $-CH_2-CH_2-CH_2-OH$ | " |
| 938 | | $-CH_2-CH(OH)-CH_3$ | yellowish red |
| 939 | 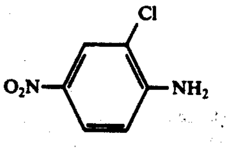 | $-CH_2-CH_2-C_6H_5$ | yellowish red |
| 940 | | $-CH_2-CH_2-OH$ | " |
| 941 | | $-CH_2-CH_2-CH_2-OH$ | " |

TABLE 6-continued

Coupling component:

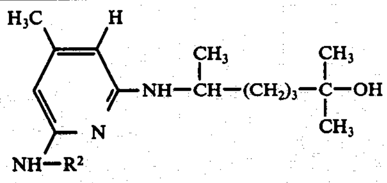

| Example | Diazo component | $R^2$ | Shade |
|---|---|---|---|
| 942 | 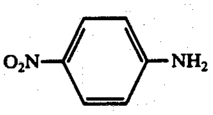 | $-CH_2-CH_2-C_6H_5$ | orange |
| 943 | | $-CH_2-CH_2-OH$ | " |
| 944 | | $-CH_2-CH_2-CH_2-OH$ | " |
| 945 | 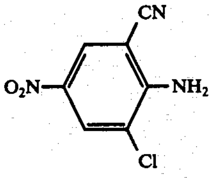 | $-C_4H_9(n)$ | bluish red |
| 946 | | $-CH_2-CH_2-OH$ | red |
| 947 | | $-CH_2-CH_2-CH_2-OH$ | " |
| 948 | 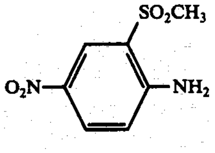 | $-C_4H_9(n)$ | red |
| 949 | | $-CH_2-CH_2-OH$ | " |
| 950 | | $-CH_2-CH_2-CH_2-OH$ | " |
| 951 | 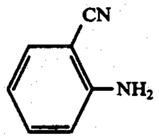 | $-CH_2-CH_2-C_6H_5$ | yellow |
| 952 | | $-CH_2-CH_2-OH$ | " |

EXAMPLE 953

20 parts of the dye of the formula:

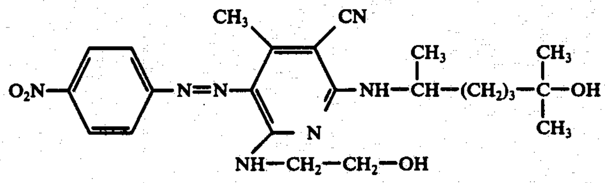

is stirred with 100 parts of formic acid for ten hours at 80° to 100° C. About 50 parts of formic acid is then distilled off at subatmospheric pressure and the residue is cooled and diluted with 500 parts by volume of water. The precipitated dye of the formula:

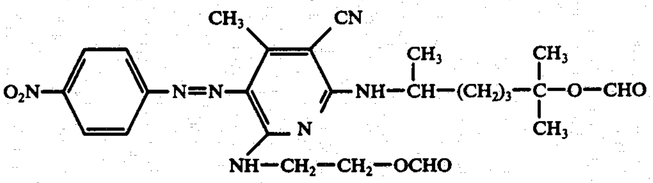

is filtered off, washed with water and dried. It dissolves in dimethylformamide with an orange color and dyes polyethylene terephthalate cloth full orange shades of excellent light fastness.

The following dyes are also valuable:

| | | |
|---|---|---|
| 954 | 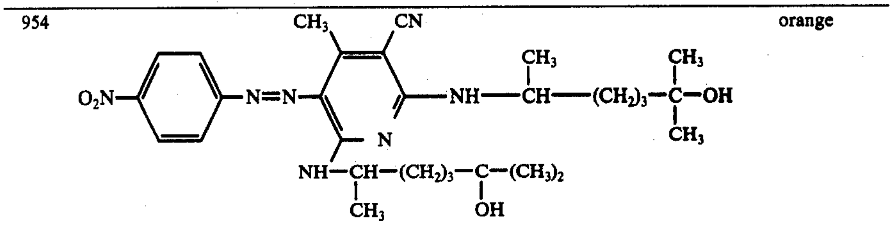 | orange |
| 955 | 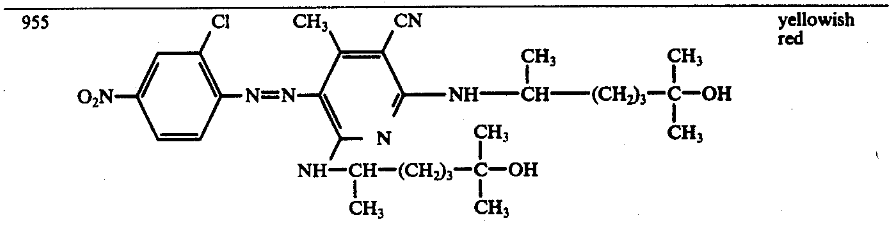 | yellowish red |
| 956 | 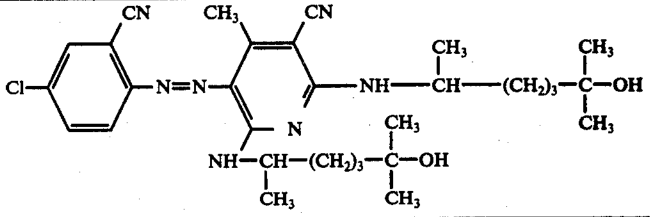 | yellow |
| 957 | 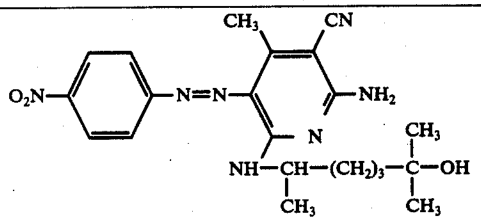 | orange |
| 958 | 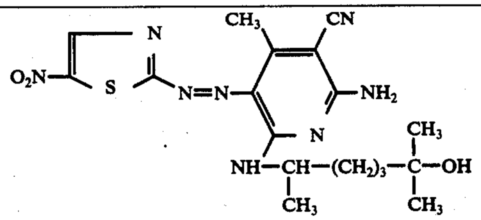 | reddish violet |
| 959 | 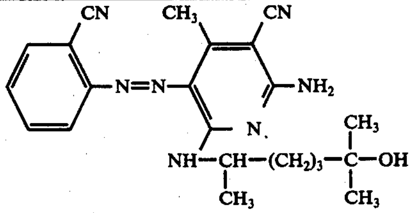 | yellow |
| 960 | 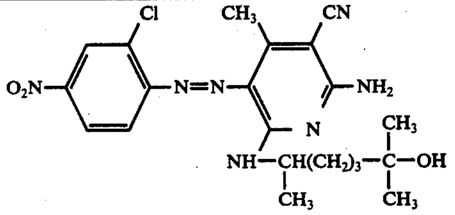 | yellowish red |
| 961 | 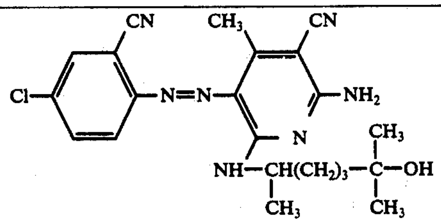 | yellow |

EXAMPLE 962

A mixture of 56 parts of 2,6-dichloro-3-cyano-4-methylpyridine, 160 parts by volume of N-methylpyrrolidone and 50 parts by volume of triethylamine has 50 parts of the amine of the formula:

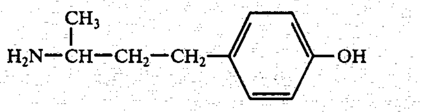

added to it. The mixture is stirred for about ten hours at 55° to 60° C, then about 1000 parts of water is added and the mixture is acidified with concentrated hydrochloric acid. A red brown oil separates and is isolated after decantation of the aqueous phase and washing with water. About 60 parts of 2-hydroxyethylamine is then added and the mixture is stirred for from three to four hours at 105° to 130° C. After cooling the whole is diluted with about 300 parts of glacial acetic acid and acidified with 50 parts by volume of concentrated hydrochloric acid. Ice is added to the mixture until it has been cooled to 0° C and then there is added a diazonium salt solution which has been prepared as follows: 49 parts of 2-amino-5-nitrobenzonitrile is added at 0° at 4° C in portions while stirring well to a mixture of 240 parts of concentrated sulfuric acid and 98 parts of 23% nitrosylsulfuric acid. The mixture is stirred for from four to five hours at 0° to 4° C and is then added in portions to the coupling mixture described above. The mixture is kept stirrable and the temperature is kept at not more than 0° C by the simultaneous addition of ice and ice-water. Aqueous sodium acetate solution is then added over twenty minutes until the pH of the coupling mixture is from 1.5 to 1.0. After coupling is over the mixture is heated to 60° to 80° C, and the precipitated dye is suction filtered, washed with water and dried. About 152 parts of a reddish brown powder is obtained which dissolves in dimethylformamide with a red color and dyes polyethylene terephthalate cloth red shades of excellent fastness to light, wet treatment and dry-heat pleating and setting.

The dye has the formula:

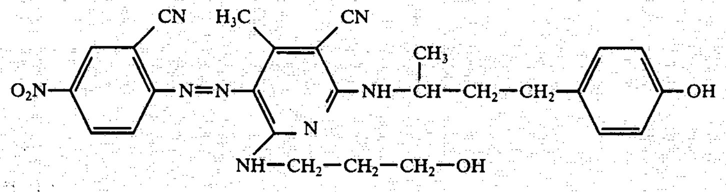

and contains a minor amount of the 2,6-dialkylaminopyridine isomer of the formula:

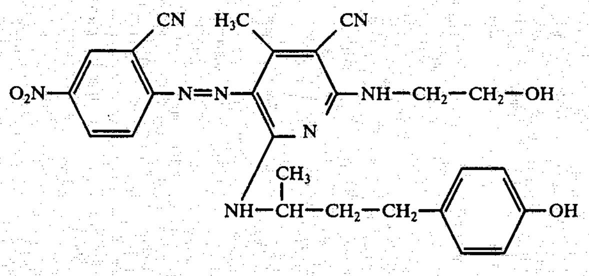

Dyes characterized in the following Tables by specifying the diazo and coupling components are obtained analogously:

TABLE 1

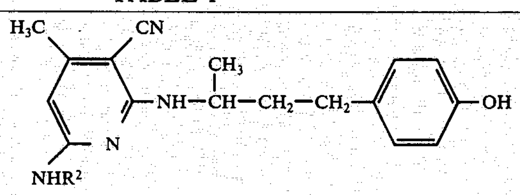

| Coupling component: Example | Diazo component | $R^2$ | Shade |
|---|---|---|---|
| 963 | 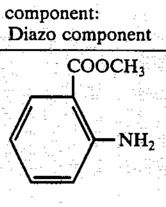 | H | yellow |
| 964 | | $-CH_2-CH_2-OH$ | " |
| 965 | | $-CH_2-CH_2-OH$ | " |
| 966 | | $-CH_2-CH-OH$<br>$CH_3$ | " |
| 967 | | $-CH_2-CH_2-O-CH_2-CH_2-OH$ | " |
| 968 | | $-CH_2-CH_2-O-CH_3$ | " |
| 969 | 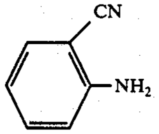 | H | yellow |
| 970 | | $-CH_2-CH_2-OH$ | " |
| 971 | | $-CH_2-CH_2-CH_2-OH$ | " |

TABLE 1-continued

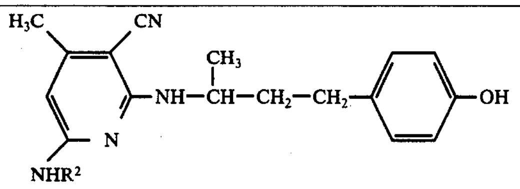

| Coupling component: Example | Diazo component | $R^2$ | Shade |
|---|---|---|---|
| 972 | | $-CH_2-CH(CH_3)-OH$ | " |
| 973 | | $-CH_2-CH_2-O-CH_2-OH$ | " |
| 974 | 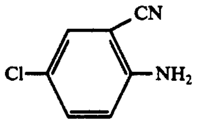 | $-H$ | " |
| 975 | | $-CH_2-CH_2-CH$ | " |
| 976 | | $-CH_2-CH_2-CH_2-OH$ | " |
| 977 | | $-CH_2-CH_2(CH_3)-OH$ | " |
| 978 | | $-CH_2-CH_2-O-CH_2-CH_2-OH$ | " |
| 979 | 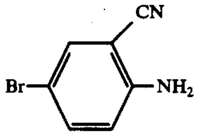 | $-H$ | " |
| 980 | | $-CH_2-CH_2-OH$ | " |
| 981 | | $-CH_2-CH_2-CH_2-OH$ | " |
| 982 | | $-CH_2-CH(CH_3)-OH$ | " |
| 982 a) | | $-CH_2-CH_2-O-CH_2-CH_2-OH$ | " |
| 983 | 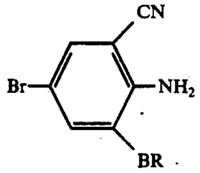 | H | orange |
| 984 | | $-CH_2-CH_2-OH$ | |
| 985 | | $-CH_2-CH_2-CH_2-OH$ | |
| 986 | | $-CH_2-CH(CH_3)-OH$ | |
| 987 | | $-CH_2-CH_2-O-CH_2-CH_2-OH$ | |
| 988 | 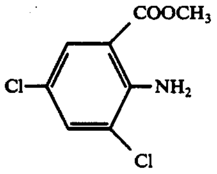 | H | orange |
| 989 | | $-CH_2-CH_2-OH$ | |
| 990 | | $-CH_2-CH_2-CH_2-OH$ | |
| 991 | | $-CH_2-CH_2-O-CH_2-CH_2-OH$ | |
| 992 | 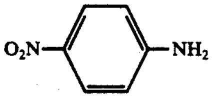 | H | orange |
| 993 | | $-CH_2-CH_2-OH$ | |
| 994 | | $-CH_2-CH_2-CH_2-OCOCH_3$ | |
| 995 | | $-CH_2-CH(OH)(CH_3)$ | |

TABLE 1-continued

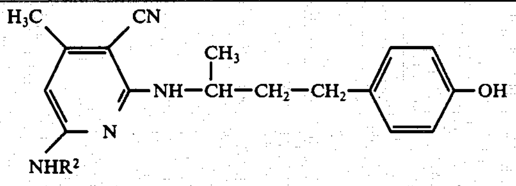

Coupling component:

| Example | Diazo component | $R^2$ | Shade |
|---|---|---|---|
| 996 | 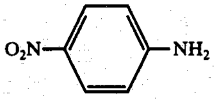 | $-CH_2-CH_2-O-CH_2-CH_2-OH$ | orange |
| 997 | | $-CH_2-CH_2-O-CH_3$ | |
| 998 | | $-CH_2-CH_2-CH_2-O-CH_3$ | |
| 999 | | $-CH_2-CH_2OCHO$ | |
| 1000 | | $-(CH_2)_6-OH$ | |
| 1001 | 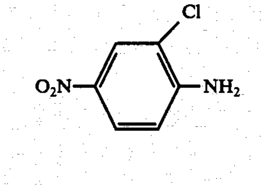 | $-H$ | yellowish red |
| 1002 | | $-CH_2-CH_2-OH$ | |
| 1003 | | $-CH_2-CH_2-CH_2-OH$ | |
| 1004 | | $-CH_2-CH_2-O-CH_2-CH_2-OH$ | |
| 1005 | | 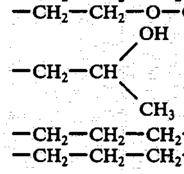 | |
| 1006 | | $-CH_2-CH_2-CH_2-O-CH_3$ | |
| 1007 | | $-CH_2-CH_2-CH_2-OCOCH_3$ | |
| 1008 | 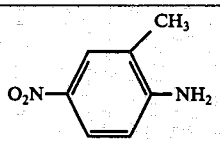 | $-CH_2-CH_2-OH$ | yellowish red |
| 1009 | | $-CH_2-CH_2-CH_2-OH$ | |
| 1010 | | $-CH_2-CH_2-O-CH_2-CH_2-OH$ | |
| 1011 | 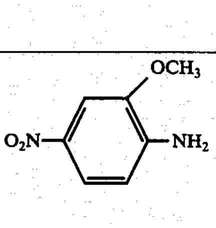 | $-CH_2-CH_2-OH$ | yellowish red |
| 1012 | | $-CH_2-CH_2-CH_2-OH$ | |
| 1013 | | $-CH_2-CH_2-O-CH_2-CH_2-OH$ | |
| 1014 | 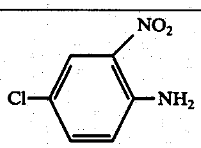 | $-CH_2-CH_2-OH$ | orange |
| 1015 | | $-CH_2-CH_2-CH_2-OH$ | |
| 1016 | 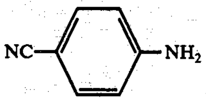 | $-CH_2-CH_2-OH$ | yellow |
| 1017 | | $-CH_2-CH_2-CH_2-OH$ | |
| 1018 | | $-CH_2-CH_2-O-CH_2-CH_2-OH$ | |
| 1019 | 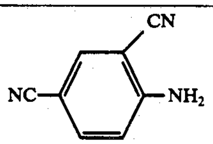 | $-CH_2-CH_2-OH$ | orange |
| 1020 | | $-CH_2-CH_2-CH_2-OH$ | |
| 1021 | | $-CH_2-CH_2-O-CH_2-CH_2-OH$ | |

TABLE 1-continued

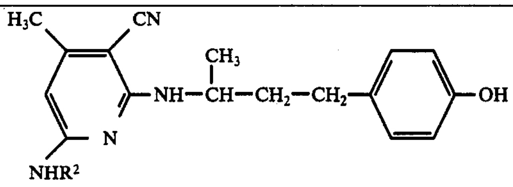

Coupling component:

| Example | Diazo component | $R^2$ | Shade |
|---|---|---|---|
| 1022 | 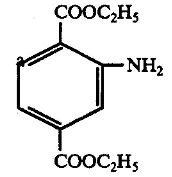 | $-CH_2-CH_2-OH$ | yellow |
| 1023 | | $-CH_2-CH_2-CH_2-OH$ | |
| 1024 | | $-CH_2-CH_2-O-CH_2-CH_2-OH$ | |
| 1025 | 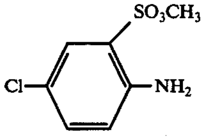 | H | yellow |
| 1026 | | $-CH_2-CH_2-OH$ | |
| 1027 | | $-CH_2-CH_2-CH_2-OH$ | |
| 1028 | | $-CH_2-CH_2-CH_2-O-CH_3$ | |
| 1029 | 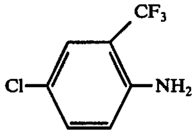 | $-CH_2-CH_2-OH$ | yellow |
| 1030 | | $-CH_2-CH_2-CH_2-OH$ | |
| 1031 | | $-CH_2-CH_2-O-CH_2-CH_2-OH$ | |
| 1032 | 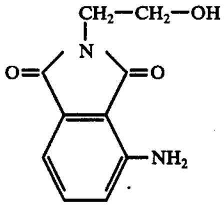 | $-H$ | yellow |
| 1033 | | $-CH_2-CH_2-OH$ | |
| 1034 | | $-CH_2-CH_2-CH_2-OH$ | |
| 1035 | | $-CH_2-CH_2-O-CH_2-OH$ | |
| 1036 | | $-CH_2-CH_2-O-CH_3$ | |
| 1037 | 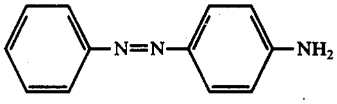 | $-CH_2-CH_2-CH_2-OH$ | yellowish red |
| 1038 | | $-CH_2-CH_2-OH$ | |
| 1039 | 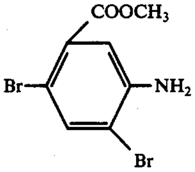 | $-CH_2-CH_2-CH_2-OH$ | orange |
| 1040 | | $-CH_2-CH_2-O-CH_2-CH_2-OH$ | |
| 1041 | 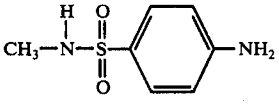 | $-CH_2-CH_2-OH$ | yellow |
| 1042 | | $-CH_2-CH_2-CH_2-OH$ | |
| 1043 | | $-CH_2-CH_2-O-CH_2-CH_2-OH$ | |
| 1044 | 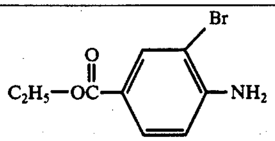 | $-CH_2-CH_2-OH$ | yellow |

TABLE 1-continued
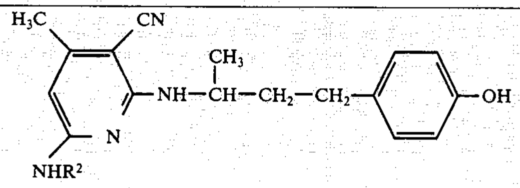
Coupling component:
| Example | Diazo component | $R^2$ | Shade |
|---|---|---|---|
| 1045 | | $-CH_2-CH_2-CH_2-OH$ | |
| 1046 | | 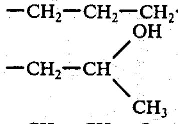 | |
| 1047 | | $-CH_2-CH_2-O-CH_2-CH_2-OH$ | |
| 1048 | 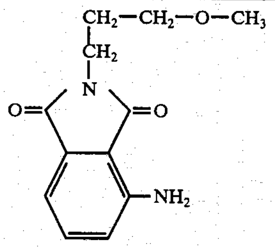 | $-CH_2-CH_2-OH$ | yellow |
| 1049 | | $-CH_2-CH_2-CH_2-OH$ | |
| 1050 | | $-CH_2-CH_2-O-CH_2-CH_2-OH$ | |
| 1051 | 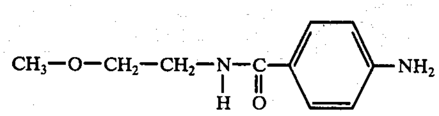 | $-CH_2-CH_2-OH$ | yellow |
| 1052 | | $-CH_2-CH_2-CH_2-OH$ | |
| 1053 | 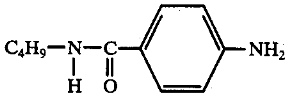 | $-CH_2-CH_2-OH$ | yellow |
| 1054 | | $-CH_2-CH_2-CH_2-OH$ | |
TABLE 2
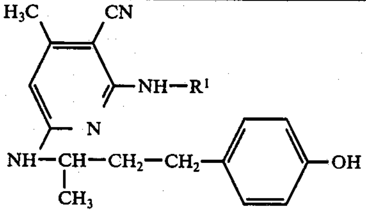
Coupling component
| Example | Diazo component | $R^1$ | Shade |
|---|---|---|---|
| 1055 | 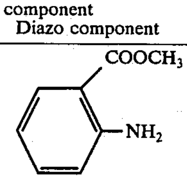 | $-CH_2-CH_2-OH$ | yellow |
| 1056 | | $-CH_2-CH_2-CH_2-OH$ | |
| 1057 | 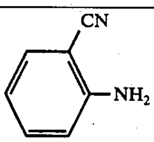 | $-H$ | yellow |
| 1058 | | $-CH_2-CH_2-OH$ | |
| 1059 | | $-CH_2-CH_2-CH_2-OH$ | |
| 1060 | | $-CH_2-CH_2-CH_2-O-(CH_2)_2OH$ | |
| 1061 | 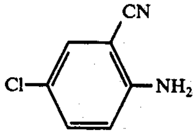 | $-CH_2-CH_2-OH$ | yellow |

TABLE 2-continued

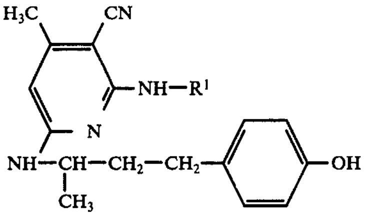

| Coupling component Example | Diazo component | $R^1$ | Shade |
|---|---|---|---|
| 1062 | | $-CH_2-CH_2-CH_2-OH$ | |
| 1063 | | $-CH_2-CH_2-O-CH_2-CH_2-OH$ | |
| 1064 | 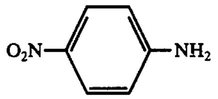 | $-CH_2-CH_2-OH$ | orange |
| 1065 | | $-CH_2-CH_2-CH_2-OH$ | |
| 1066 | | $-CH_2-CH_2-O-(CH_2)_2OH$ | |
| 1067 | 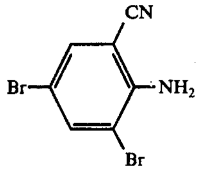 | $-CH_2-CH_2-CH_2-OH$ | orange |
| 1068 | | $-CH_2-CH_2-O-CH_2-CH_2-OH$ | |
| 1069 | 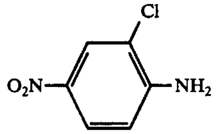 | $-CH_2-CH_2-OH$ | scarlet |
| 1070 | | $-CH_2-CH_2-CH_2-OH$ | |
| 1071 | 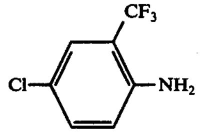 | $-CH_2-CH_2-CH_2-OH$ | yellow |
| 1072 | | $-CH_2-CH_2-O-(CH_2)_2OH$ | |
| 1073 | 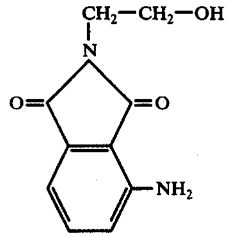 | $-CH_2-CH_2-OH$ | yellow |
| 1074 | | $-CH_2-CH_2-CH_2-OH$ | |
| 1075 | | $-CH_2-CH_2-CH_2-CH_3$ | |

EXAMPLE 1076

19.5 parts of 3-amino-5-nitro-2,1-benzoisothazole is added while stirring at 15° to 25° C in portions to about 75 to 85 parts of 96% sulfuric acid and the mixture is cooled to 0° to 4° C. 32.5 parts of 23% nitrosylsulfuric acid is then dripped in at this temperature. Diazotization is over after from about three to four hours' stirring at 0° to 5° C. The diazonium salt mixture is added to a solution or suspension of 34 parts of the coupling component of the formula:

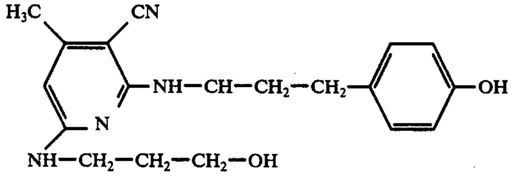

in 50 parts of 30% hydrochloric acid, 500 parts of water and 150 parts of glacial acetic acid. During coupling ice and sodium acetate are added at intervals so that the temperature of the coupling mixture does not rise above 5° C and the pH is finally about 2. The precipitated dye of the formula:

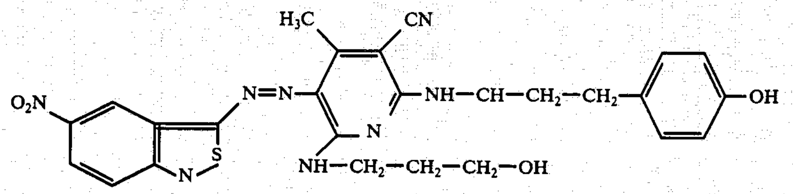

is filtered off, washed with hot water and dried. About 33 parts of a black powder is obtained which dissolves in dimethylformamide with a reddish blue color and dyes polyethylene terephthalate cloth reddish blue shades having very good fastness properties.

EXAMPLE 1077

11 parts of 2-amino-5-nitrobenzoic acid methoxyethyl ester has 180 parts by volume of glacial acetic acid, 15 parts by volume of concentrated hydrochloric acid and 10 parts of ice added to it. The whole is cooled to 0° to 5° C and then 13.5 parts by volume of 23% sodium nitrite solution is added. After stirring for from about two to three hours any excess of nitrous acid present is destroyed in the usual way, the diazonium salt solution is diluted with 1000 party by volume of ice-water and then a solution of 11.9 parts of the coupling component of the formula:

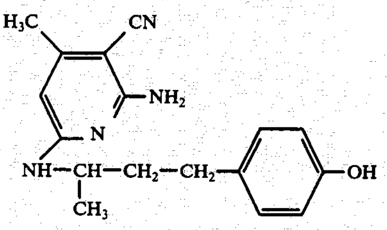

in 100 parts of glacial acetic acid and 10 parts of concentrated hydrochloric acid is added. The whole is stirred for half an hour and then 50% caustic soda solution is adde until the pH of the coupling mixture is 2. After coupling is over the precipitated dye of the formula:

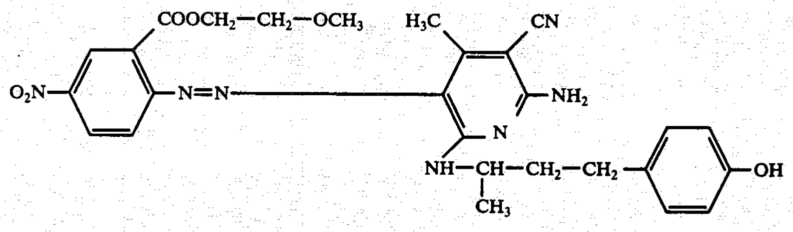

is filtered off, washed with water and dried.

A red powder is obtained which dissolves in dimethylformamide with a red color and dyes polyethylene terephthalate full yellowish red shades having very good fastness properties.

TABLE 3

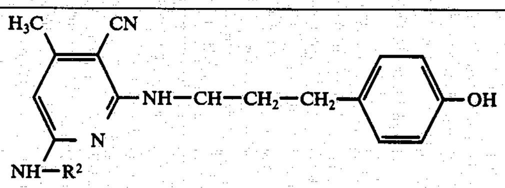

| Coupling component: Example | Diazo component | $R^2$ | Shade |
|---|---|---|---|
| 1078 | 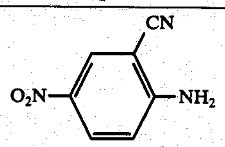 | $-CH_2-CH_3$ | |
| 1079 | | $-CH_2-CH_2-CH_2-OH$ | |
| 1080 | | $-CH_2-CH(CH_3)-OH$ | |
| 1081 | | $-CH_2-CH_2-O-CH_2-CH_2-OH$ | |
| 1082 | | $-CH_2-CH_2-CH_2-OCH_3$ | |
| 1083 | | H | |
| 1084 | | $-(CH_2)_6-OH$ | |
| 1085 | | $-CH_2-CH_2-O-COCH_3$ | |
| 1086 | 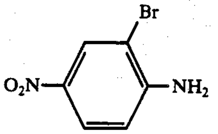 | $-CH_2-CH_2-OH$ | |
| 1087 | | $-CH_2-CH_2-CH_2-OH$ | |

TABLE 3-continued

Coupling component:

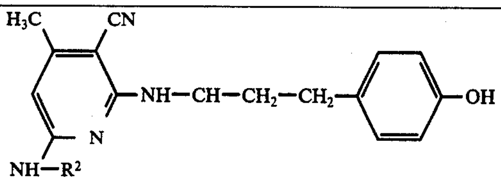

| Example | Diazo component | $R^2$ | Shade |
|---|---|---|---|
| 1088 | | $-CH_2-CH(CH_3)-OH$ | |
| 1089 | | $-CH_2-CH_2-O-CH_2-CH_2-OH$ | |
| 1090 | | H | |
| 1091 | 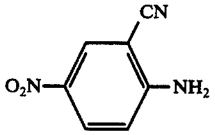 | $-H$ | |
| 1092 | | $-CH_2-CH_2-OH$ | |
| 1093 | | $-CH_2-CH_2-CH_2-OH$ | |
| 1094 | | $-CH_2-CH(CH_3)-OH$ | |
| 1095 | | $-CH_2-CH_2-O-CH_2-CH_2-OH$ | |
| 1096 | | $-CH_2-CH_2-O-CH_3$ | |
| 1097 | | $-CH_2-CH_2-CH_2-O-CH_3$ | |
| 1098 | | $-CH_2-CH_2-O-COCH_3$ | |
| 1099 | 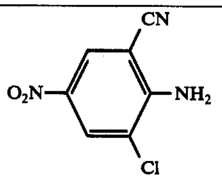 | H | red |
| 1100 | | $-CH_2-CH_2-OH$ | |
| 1101 | | $-CH_2-CH_2-CH_2-OH$ | |
| 1102 | | $-CH_2-CH(CH_3)-OH$ | |
| 1103 | | $-CH_2-CH_2-O-CH_2-CH_2-OH$ | |
| 1104 | | $-CH_2-CH_2-O-CH_3$ | |
| 1105 | | $-C_2H_5$ | |
| 1106 | 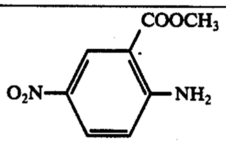 | $-CH_2-CH_2-OH$ | red |
| 1107 | | $-CH_2-CH_2-CH_2-OH$ | |
| 1108 | | $-CH_2-CH_2-O-CH_2-CH_2-OH$ | |
| 1109 | 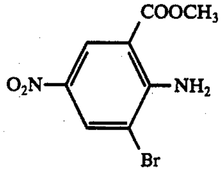 | $-CH_2-CH_2-OH$ | red |
| 1110 | | $-CH_2-CH_2-CH_2-OH$ | |
| 1111 | | $-CH_2-CH_2-O-CH_2-CH_2-OH$ | |
| 1112 | 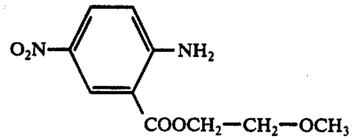 | $-CH_2-CH_2-OH$ | red |
| 1113 | | $-CH_2-CH_2-CH_2-OH$ | |
| 1114 | 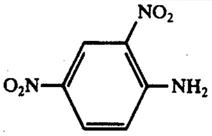 | $-H$ | red |
| 1115 | | $-CH_2-CH_2-OH$ | |
| 1116 | | $-CH_2-CH_2-CH_2-OH$ | |
| 1117 | | $-CH_2-CH_2-O-CH_2-CH_2-OH$ | |
| 1118 | | $-CH_2-CH_2-O-CH_3$ | |

TABLE 3-continued

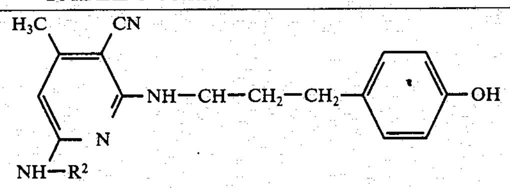

| Coupling component: Example | Diazo component | $R^2$ | Shade |
|---|---|---|---|
| 1119 | 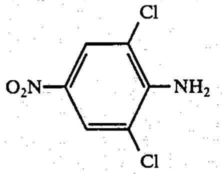 | $-CH_2-CH_2-OH$ | yellowish red |
| 1120 | | $-CH_2-CH_2-CH_2-OH$ | |
| 1121 | | $-CH_2-CH_2-O-CH_2-CH_2-OH$ | |
| 1122 | | $-CH_2-CH_2-O-CH_3$ | |
| 1123 | 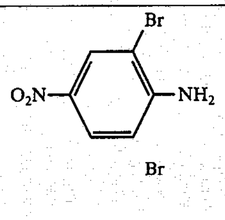 | $-CH_2-CH_2-OH$ | yellowish red |
| 1124 | | $-CH_2-CH_2-CH_2-OH$ | |
| 1125 | | $-CH_2-\underset{CH_3}{\underset{\vert}{CH}}-OH$ | |
| 1126 | | $-CH_2-CH_2-O-CH_2-CH_2-OH$ | |
| 1127 | 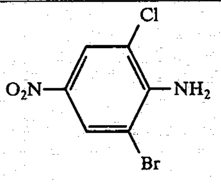 | $-CH_2-CH_2-OH$ | yellowish red |
| 1128 | | $-CH_2-CH_2-CH_2-OH$ | |
| 1129 | | $-CH_2-CH_2-CH_2-O-CH_3$ | |
| 1130 | 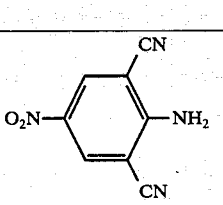 | $-CH_2-CH_2-O-H$ | bluish red |
| 1131 | | $-CH_2-CH_2-CH_2-OH$ | |
| 1132 | | $-CH_2-CH_2-O-CH_2-CH_2-OH$ | |
| 1133 | | $-CH_2-CH_2-CH_2-O-CH_3$ | |
| 1134 | 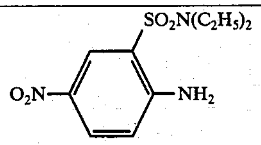 | $-CH_2-CH_2-OH$ | red |
| 1135 | | $-CH_2-CH_2-CH_2-OH$ | |
| 1136 | 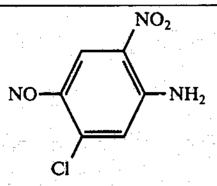 | $-CH_2-CH_2-OH$ | red |
| 1137 | | $-CH_2-CH_2-CH_2-OH$ | |
| 1138 | | $-CH_2-CH_2-O-CH_2-CH_2-OH$ | |
| 1139 | 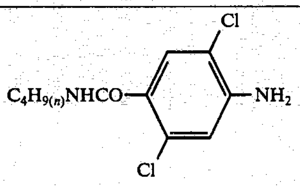 | $-CH_2-CH_2-OH$ | yellow |
| 1140 | | $-CH_2-CH_2-CH_2-OH$ | |

TABLE 3-continued

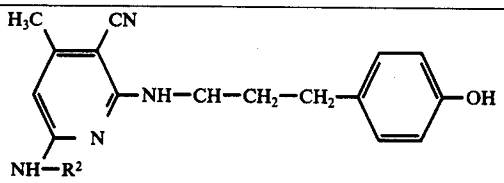

| Coupling component: Example | Diazo component | $R^2$ | Shade |
|---|---|---|---|
| 1141 | | $-CH_2-CH_2-O-CH_2-CH_2-OH$ | |
| 1142 | 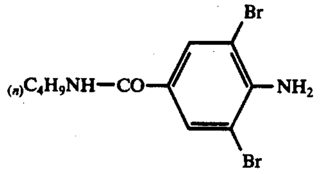 | $-CH_2-CH_2-OH$ | yellow |
| 1143 | | $-CH_2-CH_2-CH_2-OH$ | |
| 1144 | | $-CH_2-CH_2-O-CH_2-CH_2-OH$ | |
| 1145 | 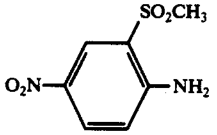 | $-H$ | red |
| 1146 | | $-CH_2-CH_2-OH$ | |
| 1147 | | $-CH_2-CH_2-CH_2-OH$ | |
| 1148 | | $-CH_2-CH(CH_3)-OH$ | |
| 1149 | | $-(CH_2)_3-O-(CH_2)_4-OH$ | |
| 1150 | 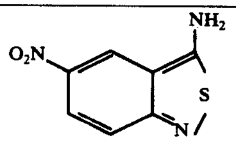 | $-CH_2-CH_2-OH$ | reddish blue |
| 1151 | | $-CH_2-CH_2-CH_2-OH$ | |
| 1152 | | $-CH_2-CH(CH_3)-OH$ | |
| 1153 | | $-CH_2-CH_2-O-CH_2-CH_2-OH$ | |
| 1154 | | $-(CH_2)_6-OH$ | |
| 1155 | | $-(CH_2)_3-O-(CH_2)_4-OH$ | |
| 1156 | | $-CH_2-CH_2-CH_2-O-C(=O)-CH_3$ | |
| 1157 | 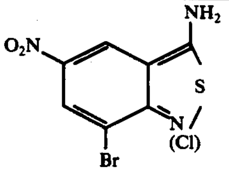 | $-CH_2-CH_2-O-CH_2-CH_2-OH$ | blue |
| 1158 | 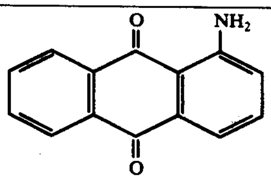 | $-CH_2-CH_2-CH_2-OH$ | yellowish brown |
| 1159 | | $-CH_2-CH_2-O-CH_2-CH_2-OH$ | |
| 1160 | 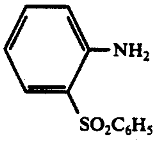 | $-CH_2-CH_2-CH_2-OH$ | yellow |
| 1161 | | $-CH_2-CH_2-O-CH_2-CH_2-OH$ | |
| 1162 | 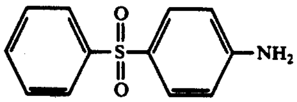 | $-CH_2-CH_2-O-CH_2-CH_2-OH$ | yellow |
| 1163 | | $-(CH_2)_3-O-H$ | |

TABLE 3-continued

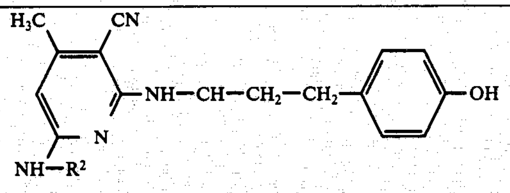

Coupling component:

| Example | Diazo component | $R^2$ | Shade |
|---|---|---|---|
| 1164 | 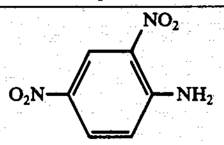 | $-CH_2-CH_2-OH$ | bluish red |
| 1165 | | $-CH_2-CH_2-CH_2-OH$ | |
| 1166 | | H | |
| 1167 | | $-CH_2-CH_2-O-CH_2-CH_2-OH$ | |
| 1168 | 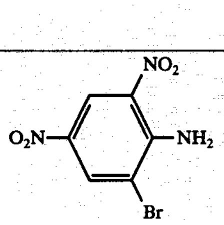 | $-(CH_2)_3{}_3-OH$ | bluish red |
| 1169 | | $-CH_2-CH_2-O-CH_2-CH_2-OH$ | |
| 1170 | | H | |
| 1171 | 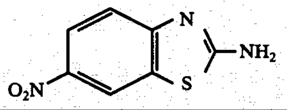 | $-CH_2-CH_2-OH$ | yellowish red |
| 1172 | 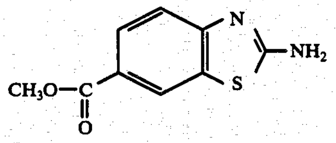 | $-CH_2-CH_2-CH_2-OH$ | scarlet |
| 1173 | | $-CH_2-CH_2-OH$ | |
| 1174 | 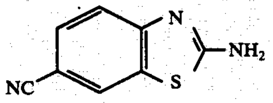 | $-CH_2-CH_2-OH$ | scarlet |
| 1175 | 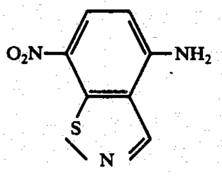 | H | bluish red |
| 1176 | | $-CH_2-CH_2-OH$ | |
| 1177 | | $-CH_2-CH_2-CH_2-OH$ | |
| 1178 | | $-CH_2-CH_2-O-CH_2-CH_2-OH$ | |
| 1179 | | $-(CH_2)_3-O-(CH_2)_4-OH$ | |
| 1180 | 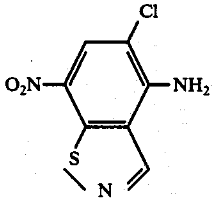 | $-CH_2-CH_2-CH_2-OH$ | violet |
| 1181 | | $-CH_2-CH_2-O-CH_2-CH_2-OH$ | violet |
| 1182 | | $-H$ | bluish red |
| 1183 | 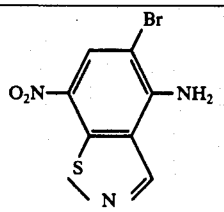 | $-CH_2-CH_2-CH_2-OH$ | violet |
| 1184 | | $-CH_2-CH_2-O-CH_2-CH_2-OH$ | |

TABLE 3-continued

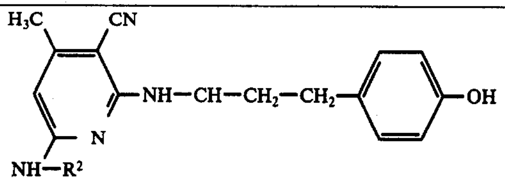

Coupling component:

| Example | Diazo component | $R^2$ | Shade |
|---|---|---|---|
| 1185 | 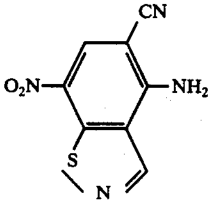 | $-CH_2-CH_2-CH_2-OH$ | |
| 1186 | 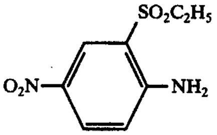 | $-CH_2-CH_2-O-CH_2-CH_2-OH$ | |
| 1187 | | $-CH_2-CH_2-CH_2-OH$ | red |
| 1188 | 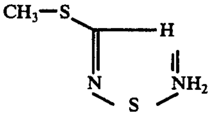 | $-H$ | orange |
| 1189 | | $-CH_2-CH_2-OH$ | |
| 1190 | | $-CH_2-CH_2-CH_2-OH$ | |
| 1191 | | $-CH_2-CH_2-O-CH_2-CH_2-OH$ | |
| 1192 | 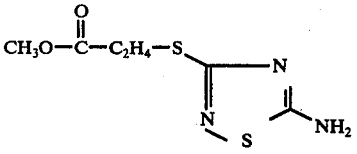 | $-CH_2-CH_3$ | orange |
| 1193 | | $-CH_2-CH_2-CH_2-OH$ | |
| 1194 | | $-CH_2-\underset{CH_3}{\underset{\vert}{CH_2}}$ | |
| 1195 | | $-CH_2-CH_2-O-CH_2-CH_2-OH$ | |
| 1196 | | $-H$ | |
| 1197 | 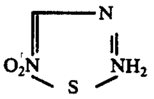 | $-CH_2-CH_2-OH$ | |
| 1198 | | $-CH_2-CH_2-CH_2-OH$ | |
| 1199 | | $-CH_2-CH_2-O-CH_2-CH_2-OH$ | |
| 1200 | 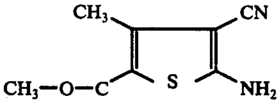 | $-CH_2-CH_2-OH$ | bluishred |
| 1201 | | $-CH_2-CH_2-CH_2-OH$ | |
| 1202 | | $-CH_2-CH_2-O-CH_2-CH_2-OH$ | |
| 1203 | | $-CH_2-\underset{CH_3}{\underset{\vert}{CH}}-OH$ | |
| 1204 | 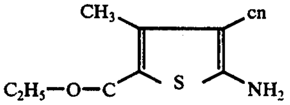 | $-CH_2-CH_2-OH$ | bluish red |
| 1205 | | $-CH_2-CH_2-CH_2-OH$ | |
| 1206 | | $-CH_2-CH_2-O-CH_2-CH_2-OH$ | |
| 1207 | 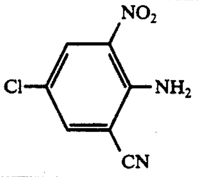 | $-CH_2-CH_2-CH_2-OH$ | yellowish red |

TABLE 3-continued

Coupling component:

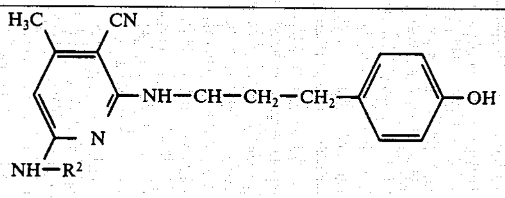

| Example | Diazo component | $R^2$ | Shade |
|---|---|---|---|
| 1208 | 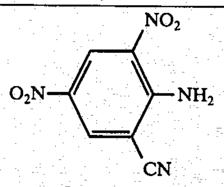 | $-CH_2-CH_2-OH$ | bluish red |
| 1209 | | $-CH_2-CH_2-CH_2-OH$ | |
| 1210 | | H | |
| 1211 | 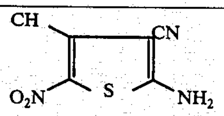 | $-CH_2-CH_2-OH$ | violet |
| 1212 | | $-CH_2-CH_2-CH_2-OH$ | |
| 1213 | 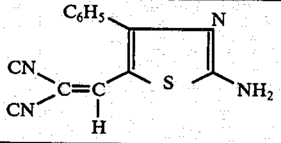 | $-CH_2-CH_2-CH_2-OH$ | reddish blue |

TABLE 4

Coupling component:

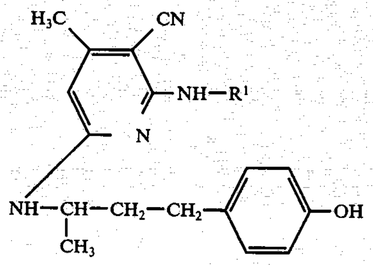

| Example | Diazo component | $R^2$ | Shade |
|---|---|---|---|
| 1214 | 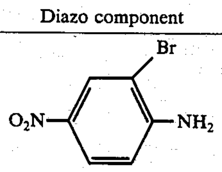 | $-CH_2-CH_2-OH$ | yellowish red |
| 1215 | | $-CH_2-CH_2-CH_2-OH$ | |
| 1216 | | $-CH_2-CH_2-O-CH_2-CH_2-OH$ | |
| 1217 | 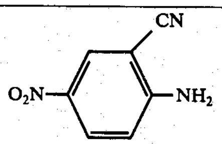 | $-H$ | yellowish red |
| 1218 | | $-CH_2-CH_2-OH$ | |
| 1219 | | $-CH_2-CH_2-O-COCH_3$ | |
| 1220 | | $-CH_2-CH_2-CH_2-OH$ | |
| 1221 | | $-CH_2-CH_2-O-CH_2-CH_2-OH$ | |
| 1222 | | $-CH_2-CH_2-O-CH_2-CH_2-OCHO$ | |
| 1223 | | $-(CH_2)_6OH$ | |
| 1224 | 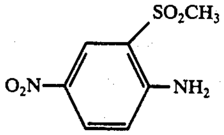 | $-CH_2-CH_2-CH_2-OH$ | red |
| 1225 | | $-CH_2-CH_2-OH$ | |

TABLE 4-continued
Coupling component:
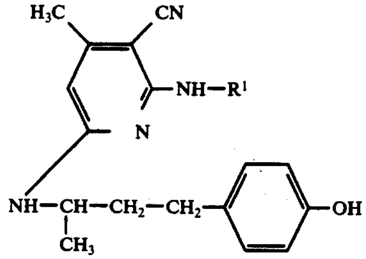
| Example | Diazo component | $R^2$ | Shade |
|---|---|---|---|
| 1226 | 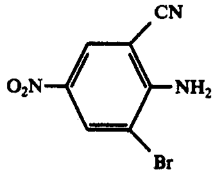 | $-H$ | |
| 1227 | | $-CH_2-CH_2-OH$ | |
| 1228 | | $-CH_2-CH_2-CH_2-OH$ | |
| 1229 | | $-CH_2-CH_2-O-CH_2-CH_2-OH$ | |
| 1230 | 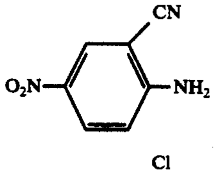 | $-H$ | red |
| 1231 | | $-CH_2-CH_2-OH$ | |
| 1232 | | $-CH_2-CH_2-CH_2-OH$ | |
| 1233 | | $-CH_2-CH_2-O-CH_2-CH_2-OH$ | |
| 1234 | | $-(CH_2)_3-O-(CH_2)_4-OH$ | |
| 1235 | 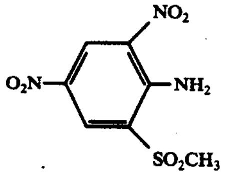 | $-CH_2-CH_2-CH_2-OH$ | violet |
| 1236 | 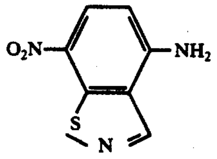 | $-CH_2-CH_2-CH_2-OH$ | |
| 1237 | | $-CH_2-CH_2-O-CH_2-CH_2-OH$ | |
| 1238 | 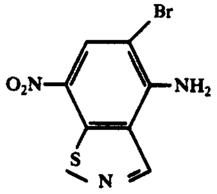 | $-CH_2-CH_2-CH_2-OH$ | violet |
| 1239 | | $-CH_2-CH_2-O-CH_2-CH_2-OH$ | |
| 1240 | 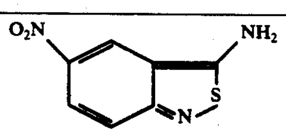 | $-CH_2-CH_2-CH_2-OH$ | reddish blue |
| 1241 | | $-CH_2-CH_2-O-CH_2-CH_2-OH$ | |
| 1242 | 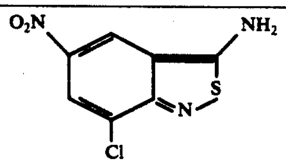 | $-CH_2-CH_2-O-CH_2-CH_2-OH$ | blue |

TABLE 4-continued

Coupling component:

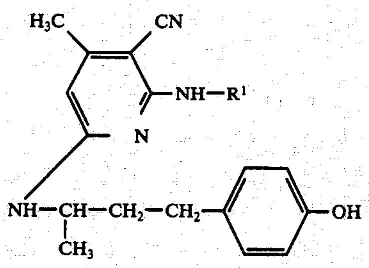

| Example | Diazo component | $R^2$ | Shade |
|---|---|---|---|
| 1243 | 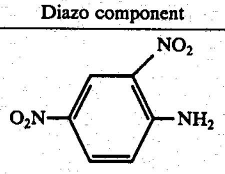 | $-H$ | red |
| 1244 | | $-CH_2-CH_2-OH$ | |
| 1245 | | $-CH_2-CH_2-CH_2-OH$ | |
| 1246 | | $-CH_2-CH_2-O-CH_2-CH_2-OH$ | |
| 1247 | 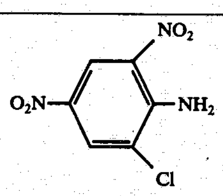 | $-CH_2-CH_2-CH_2-OH$ | bluish red |
| 1248 | | $-CH_2-CH_2-O-CH_2-CH_2-OH$ | |
| 1249 | 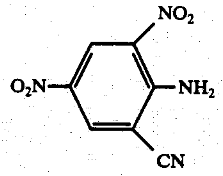 | $-CH_2-CH_2-CH_2-OH$ | bluish red |
| 1250 | | $-CH_2-CH_2-O-(CH_2)_2OH$ | |
| 1251 | 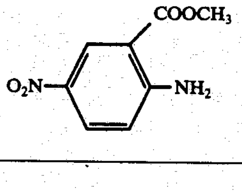 | $-CH_2-CH_2-CH_2-OH$ | red |
| 1252 | | $-CH_2-CH_2-O-CH_2-CH_2-OH$ | |

TABLE 5

Dye:

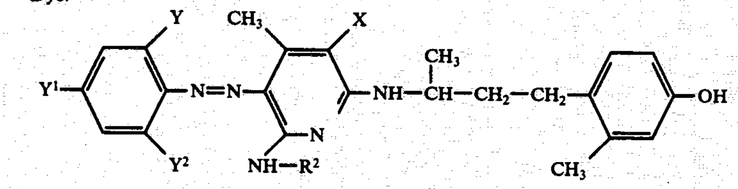

| No. | Y | $Y^1$ | $Y^2$ | E | Shade |
|---|---|---|---|---|---|
| 1345 | $-Cl$ | $-NO_2$ | $-H$ | $-CH_3$ | yellowish red |
| 1346 | $-Cl$ | $-Cl$ | $-CN$ | $-CH_3$ | orange |
| 1347 | $-CN$ | $-Br$ | $-H$ | $-CH_3$ | yellow |
| 1348 | $-CH_3$ | $-NO_2$ | $-H$ | $-CH_3$ | orange |
| 1349 | $-OCH_3$ | $-NO_2$ | $-H$ | $-CH_3$ | yellowish red |
| 1350 | $-SO_2CH_3$ | $-NO_2$ | $-H$ | $-CH_3$ | bluish red |
| 1351 | $-CF_3$ | $-H$ | $-H$ | $-CH_3$ | yellow |
| 1352 | $-CF_3$ | $-Cl$ | $-H$ | $-CH_3$ | yellow |
| 1353 | $-CN$ | $-CN$ | $-H$ | $-CH_3$ | orange |
| 1354 | $-H$ | $-NO_2$ | $-H$ | $-C_2H_5$ | orange |
| 1355 | $-H$ | $-NO_2$ | $-H$ | $-C_3H_7(n)$ | orange |

TABLE 6

Coupling component:

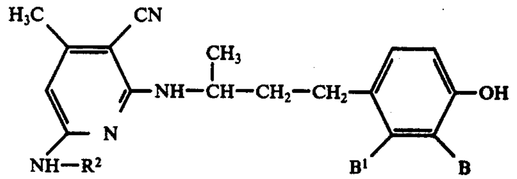

| No. | Diazo component | $R^2$ | B | $B^1$ | Shade |
|---|---|---|---|---|---|
| 1269 | 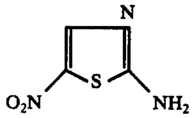 | $-CH_2-CH_2-OH$ | $-CH_3$ | $-H$ | reddish violet |
| 1270 | | $-CH_2-CH_2-OH$ | $-H$ | $-CH_3$ | reddish violet |
| 1271 | | $-CH_2-CH_2-OH$ | $-H$ | $-Cl$ | reddish violet |
| 1272 | 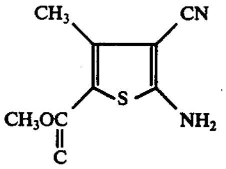 | $-CH_2-CH_2-OH$ | $-CH_3$ | $-H$ | bluish red |
| 1273 | 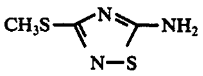 | $-CH_2-CH_2-OH$ | $-CH_3$ | $-H$ | orange |
| 1274 | | $-CH_2-CH_2-OH$ | $-H$ | $-CH_3$ | orange |
| 1275 | 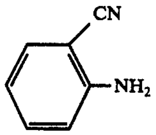 | $-CH_2-CH_2-OH$ | $-H$ | $-CH_3$ | yellow |
| 1276 | | $-CH_2-CH_2-OH$ | $-C(CH_3)_3$ | $-H$ | yellow |
| 1277 | | $-CH_2-CH_2-OH$ | $-H$ | $-OCH_3$ | yellow |
| 1278 | | $-CH_2-CH_2-CH_2-OH$ | $-H$ | $-CH_3$ | yellow |
| 1279 | 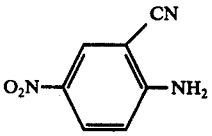 | $-CH_2-CH_2-CH_2-OH$ | $-H$ | $-CH_3$ | red |
| 1280 | | $-CH_2-CH_2-OH$ | $-H$ | $-CH_3$ | red |
| 1281 | 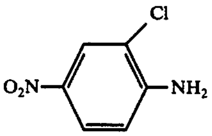 | $-CH_2-CH_2-OH$ | $-H$ | $-CH_3$ | yellowish red |
| 1282 | 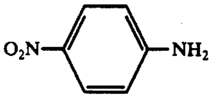 | $-CH_2-CH_2-OH$ | $-H$ | $-CH_3$ | orange |

TABLE 7
Coupling component:
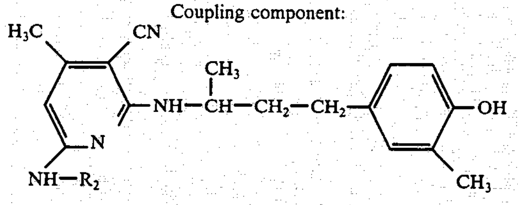
| Example | Diazo component | $R^2$ | Shade |
|---|---|---|---|
| 1283 | 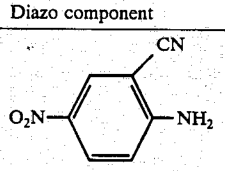 | H | yellowish red |
| 1284 | | $-CH_2-CH_2-OH$ | red |
| 1285 | | $-CH_2-CH_2-CH_2-OH$ | red |
| 1286 | | 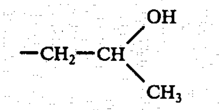 | yellowish red |
| 1287 | | $-CH_2-CH_2-O-CH_2-CH_2-OH$ | |
| 1288 | 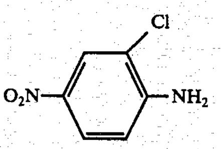 | H | yellowish red |
| 1289 | | $-CH_2-CH_2-OH$ | |
| 1290 | | $-CH_2-CH_2-CH_2-OH$ | |
| 1291 | | $-CH_2-CH_2-O-CH_2-CH_2-OH$ | |
| 1292 | 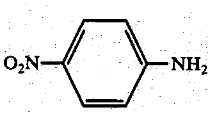 | H | orange |
| 1293 | | $-CH_2-CH_2-OH$ | |
| 1294 | | $-CH_2-CH_2-CH_2-OH$ | |
| 1295 | | $-CH_2-CH_2-O-CH_2-CH_2-OH$ | |
| 1296 | 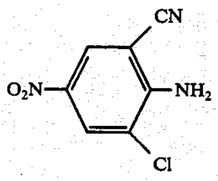 | H | |
| 1297 | | $-CH_2-CH_2-OH$ | |
| 1298 | | $-CH_2-CH_2-CH_2-OH$ | |
| 1299 | 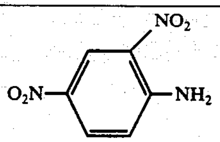 | H | red |
| 1300 | | $-CH_2-CH_2-OH$ | |
| 1301 | | $-CH_2-CH_2-CH_2-OH$ | |
| 1302 | 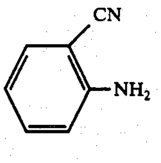 | H | yellow |
| 1303 | | $-CH_2-CH_2-OH$ | |

TABLE 8

Dye:

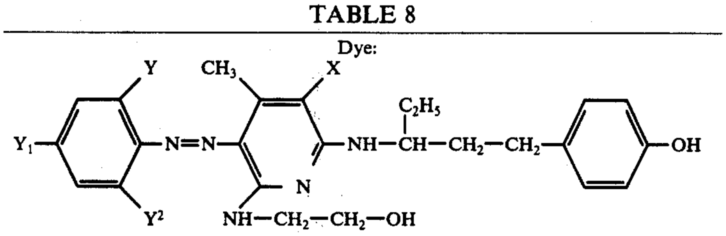

| No. | Y | $Y_1$ | $Y_2$ | X | Shade |
|---|---|---|---|---|---|
| 1304 | —CN | —H | —H | —H | yellow |
| 1305 | —CN | $—NO_2$ | —H | —CN | red |
| 1306 | —CN | $—NO_2$ | —Cl | —CN | red |
| 1307 | —CN | —Cl | —H | —H | orange |
| 1308 | —H | $—NO_2$ | —H | —CN | orange |
| 1309 | —Cl | $—NO_2$ | —H | —H | red |
| 1310 | —Cl | —Cl | —CN | —CN | orange |
| 1311 | —CN | —Br | —H | —CN | yellow |
| 1312 | $—CH_3$ | $—NO_2$ | —H | —CN | orange |
| 1313 | $—OCH_3$ | $—NO_2$ | —H | —CN | yellowish red |
| 1314 | $—SO_2CH_3$ | $—NO_2$ | —H | —CN | bluish red |
| 1315 | —CF | —H | —H | —CN | yellow |
| 1316 | $—CF_3$ | —Cl | —H | —CN | yellow |
| 1317 | —CN | —CN | —H | —CN | orange |
| 1318 | —CN | $—NO_2$ | —Br | —CN | red |
| 1319 | —Cl | $—NO_2$ | —H | —CN | yellowish red |
| 1320 | —Br | $—NO_2$ | —H | —CN | yellowish red |
| 1321 | —H | $—NO_2$ | —H | —H | red |
| 1322 | —H | $—NO_2$ | —H | $—CONH_2$ | yellowish red |

Particular value attaches for example to dyes of the formulae:

| No. | | Shade |
|---|---|---|
| 1323 | 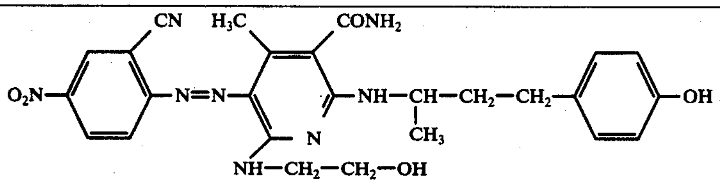 | bluish red |
| 1324 | 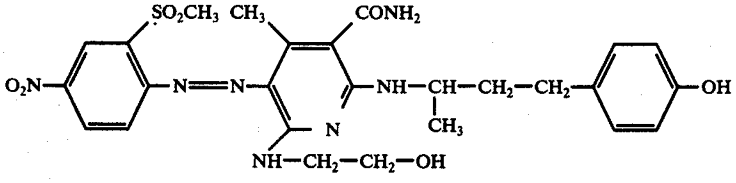 | bluish red |
| 1325 | 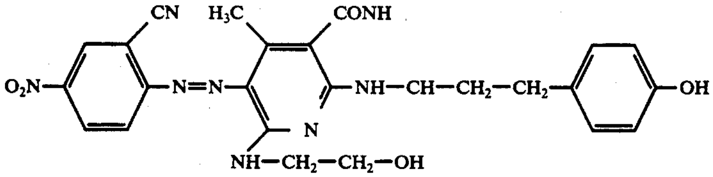 | reddish violet |
| 1326 | 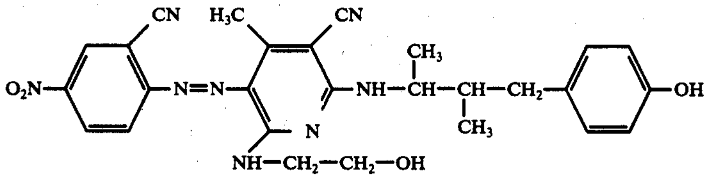 | red |
| 1327 | 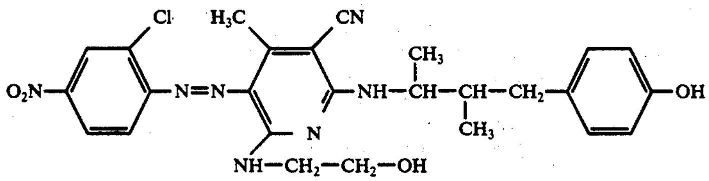 | red |

-continued
| No. | | Shade |
|---|---|---|
| 1328 | 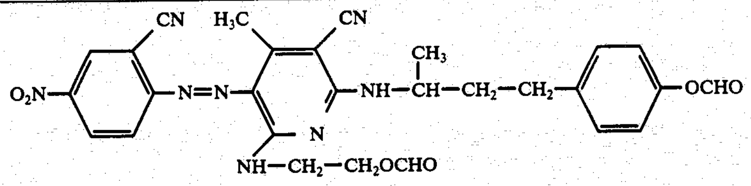 | red |
| 1329 | 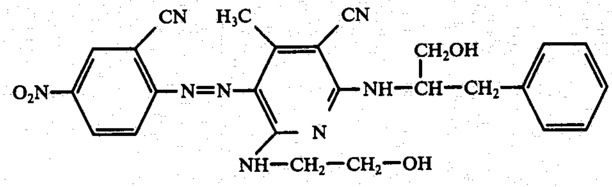 | red |
| 1330 | 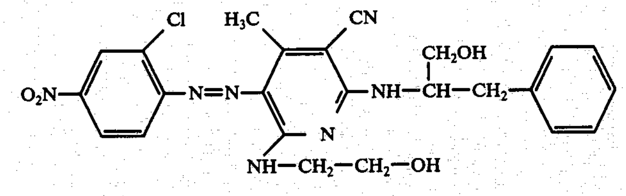 | yellowish red |
| 1331 | 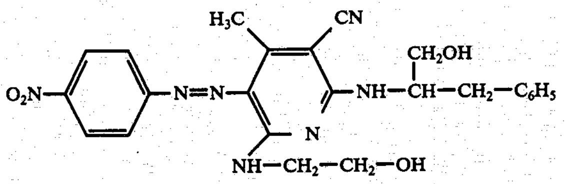 | orange |
| 1332 | 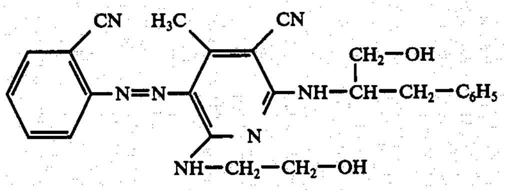 | yellowish red |
| 1333 | 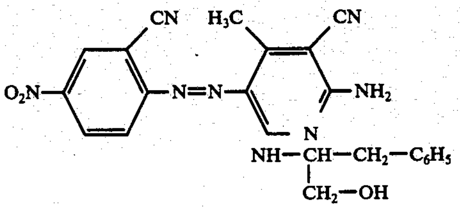 | yellowish red |
TABLE 9
Dye
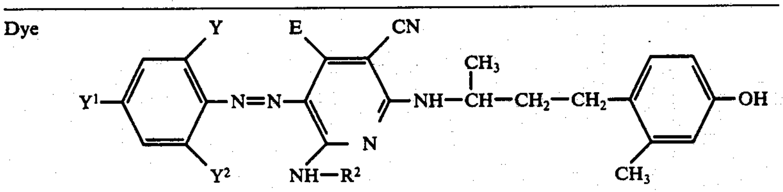
| No. | Y | Y[1] | Y[2] | E | R[2] | Shade |
|---|---|---|---|---|---|---|
| 1354 | $-SO_2CH_3$ | $-NO_2$ | $-H$ | $-CH_3$ | $-CH_2-CH_2-OH$ | red |
| 1355 | $-SO_2CH_3$ | $-NO_2$ | $-H$ | $-C_3H_7(n)$ | $-CH_2-CH_2-OH$ | red |
| 1356 | $-SO_2CH_3$ | $-NO_2$ | $-H$ | $-C_5H_{11}(n)$ | $-CH_2-CH_2-OH$ | red |
| 1357 | $-CN$ | $-NO_2$ | $-H$ | $-CH_3$ | $-CH_2-CH_2-OH$ | red |
| 1358 | $-CN$ | $-Cl$ | $-H$ | $-CH_3$ | $-CH_2-CH_2-OH$ | yellow |
| 1359 | $-CN$ | $-H$ | $-H$ | $-CH_3$ | $-CH_2-CH_2-OH$ | yellow |

TABLE 10

Dye

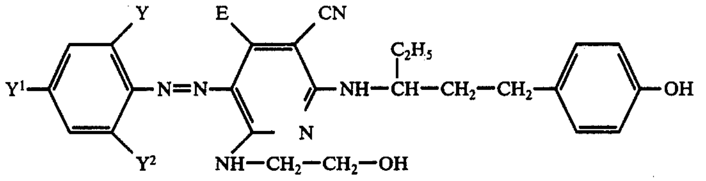

| No. | Y | $Y^1$ | $Y^2$ | E | Shade |
|---|---|---|---|---|---|
| 1340 | $-CN$ | $-H$ | $-H$ | $-CH_3$ | yellow |
| 1341 | $-CN$ | $-NO_2$ | $-H$ | $-CH_3$ | red |
| 1342 | $-CN$ | $-NO_2$ | $-Cl$ | $-CH_3$ | red |
| 1343 | $-CN$ | $-Cl$ | $-H$ | $-CH_3$ | yellow |
| 1344 | $-H$ | $-NO_2$ | $-H$ | $-CH_3$ | orange |

EXAMPLE 1356

9.8 parts of 2-amino-5,nitrobenzonitrile is added to 0° to 4° C in portions while stirring well to a mixture of 48 parts of concentrated sulfuric acid and 19.6 parts of 23% nitrosylsulfuric acid. The diazo solution is stirred for from four to five hours at 0° to 4° C and the diazonium salt mixture is then added in portions to a solution or suspension, cooled to 0° C, of 23.5 parts of the coupling component of the formula:

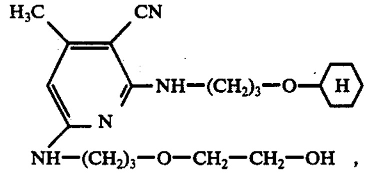

which contains a minor fraction of the coupling component of the formula:

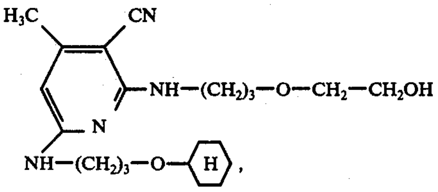

in a mixture of 150 parts by volume of glacial acetic acid, 20 parts by volume of concentrated hydrochloric acid, 1 part of sulfamic acid and 500 parts by volume of water. Sodium acetate and ice are added during coupling so that the pH of the mixture is always from 0 to 2, the temperature is about 0° C and the mixture remains easily stirred. After coupling is over (it proceeds very rapidly at pH 1 to 2) the precipitated dye mixture of the formula:

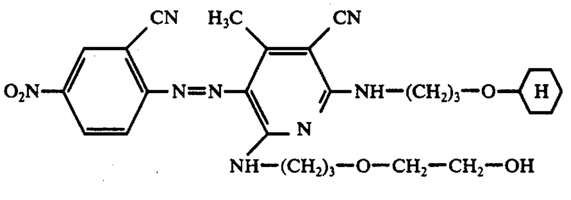

(which contains a minor amount of the 2,6-dialkylaminopyridine isomer) is suction filtered and the residue washed with water and dried. A reddish brown powder is obtained which dissolves in dimethylformamide with a red color and dyes polyethylene terephthalate cloth red shades of excellent light fastness.

EXAMPLE 1357

8.8 parts of the diazo component of the formula:

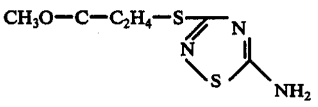

is stirred in 24 parts of concentrated sulfuric acid at 10° to 15° C. The whole is then cooled to 8° to 10° C and at this temperature 70 parts by volume of glacial acetic acid and 12 parts by volume of propionic acid are added while cooling. After further cooling to 0° to 4° C 13 parts of nitrosylsulfuric acid is dripped in and the whole is stirred for three hours at 0° to 4° C. The diazonium salt solution thus obtained is added to 13.1 parts of a solution or suspension, cooled to 0° C, of the coupling component of the formula:

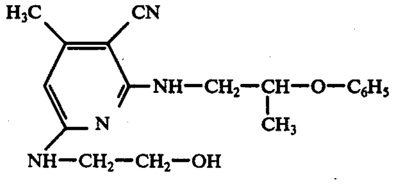

(a minor portion of the coupling component consisting of the 2,6-dialkylaminopyridine isomer) in a mixture of 150 parts by volume of glacial acetic acid, 15 parts by volume of concentrated hydrochloric acid, 500 parts of water and 1 part of sulfamic acid.

Ice and sodium acetate are added during coupling so that the temperature does not rise above 0° C and the pH remains at from 2 to about 0. Ice-water may also be added if the mixture becomes too difficult to stir.

Coupling is rapidly ended at pH 2. The precipitated dye mixture of the formulae:

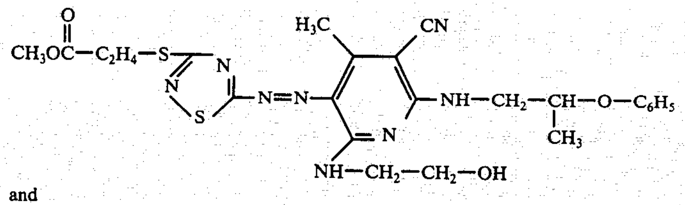

and

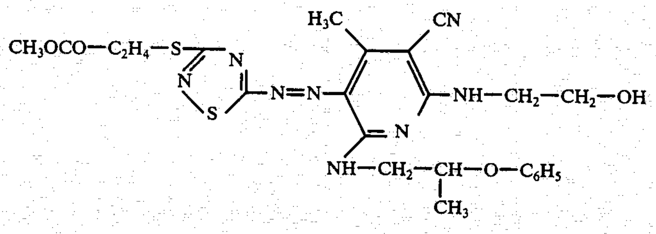

is filtered off, washed with water and dried. A brown powder is obtained which dissolves in dimethylformamide with an orange red color and dyes polyethylene terephthalate cloth orange shades of excellent light fastness.

EXAMPLE 1358

5.5 parts of p-nitroaniline is stirred with 40 parts by volume of water and 15 parts by volume of concentrated hydrochlirc acid. The whole is then diluted with ice and hydrochloric acid to a volume of 200 parts by volume, 13 parts by volume of 23% sodium nitrite solution is added and the whole is stirred for two hours. After the diazonium salt solution has been filtered any excess of nitrous acid present is destroyed as usual and the diazonium salt solution is added to a solution or dispersion, cooled to 5° C, of 10 parts of the coupling component:

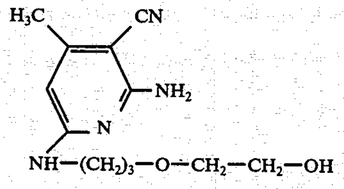

in 250 parts of water and 20 parts of concentrated hydrochloric acid. The pH of the coupling mixture is raised to 2 to 3 by stewing in sodium acetate so that the coupling is rapidly ended. The precipitated dye of the formula:

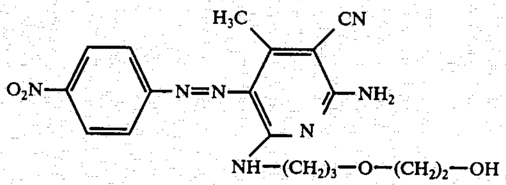

is suction filtered, washed with water and dried. About 15 parts of a yellowish red powder is obtained which dissolves in dimethylformamide with an orange color and dye polyethylene terephthalate cloth full orange shades having very good fastness to light and dry-heat pleating the setting by the carrier and HT methods.

The dyes set out in the following Tables can be prepared by the methods described in Examples 1356 to 1358:

TABLE 1

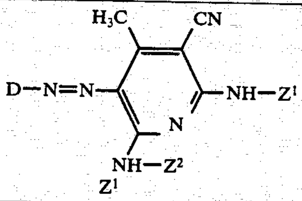

| Example | D-NH | $Z^1$ | $Z_2$ | Shade |
|---|---|---|---|---|
| 1359 | 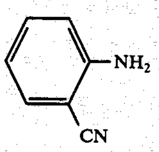 | $-(CH_2)_3-O-(CH_2-CH_2-O)_2-CH_2$ | $-(CH_2)_3O(CH_2)_4OH$ | yellow |
| 1360 | | $-CH_2-\underset{OH}{CH}-C_6H_5$ | $-(CH_2)_3O(CH_2)_6-OH$ | " |
| 1361 | | " | $-(CH_2)_3O(CH_2CH_2O)_2C_2H_5$ | " |
| 1362 | 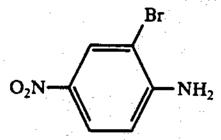 | $-H$ | $-(CH_2)_3O(CH_2)_6-OH$ | yellowish red |

TABLE 1-continued
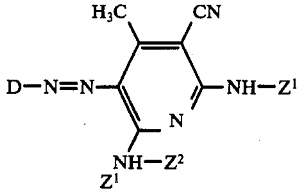
| Example | D-NH | $Z^1$ | $Z_2$ | Shade |
|---|---|---|---|---|
| 1363 | 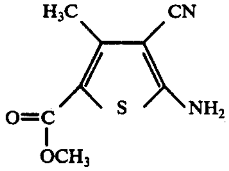 | $-H$ | $-(CH_2)_3-O-(CH_2)_6OH$ | red |
| 1364 | 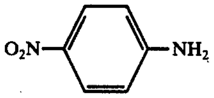 | 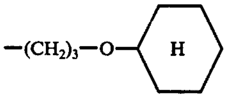 | $-CH_2-CH_2-OH$ | orange |
| 1365 | " | 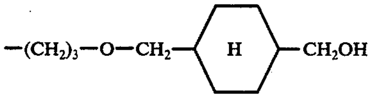 | " | orange |
| 1366 | 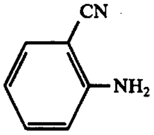 | 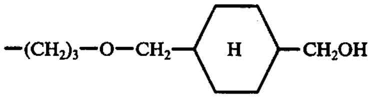 | " | yellow |
| 1367 | 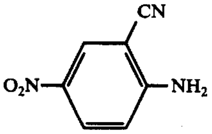 | " | " | red |
TABLE 2
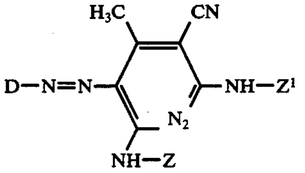
| Ex. | D-$NH_2$ | $Z^1$ | $Z^2$ | Shade |
|---|---|---|---|---|
| 1368 | 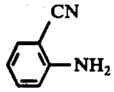 | $-(CH_2)_3-O-C_2H_4-O-C_2H_5$ | " | yellow |
| 1369 | " | $-(CH_2)_3-O-C_2H_4-O-C_6H_5$ | " | " |
| 1370 | " | $-(CH_2)_3-O-CH(CH_3)-CH_2-O-C_6H_5$ | " | " |
| 1371 | " | $-CH_2-CH(CH_3)-O-C_6H_5$ | $-CH_2-CH_2-OH$ | " |
| 1372 | " | $-(CH_2)_3-O-CH_2-CH_2-C_6H_5$ | " | " |
| 1373 | " | $-(CH_2)_3-O-CH_2-C_6H_5$ | " | " |
| 1374 | " | $-H$ | $-(CH_2)_3-O-CH_2-C_6H_5$ | " |
| 1375 | " | $-H$ | $-(CH_2)_3-O-(C_2H_4-O)_3C_6H_5$ | " |
| 1376 | 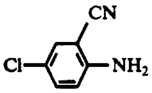 | $-(CH_2)_3-O-CH_2-CH_2OCH_2C_6H_5$ | $-CH_2-CH_2-OH$ | " |

TABLE 2-continued

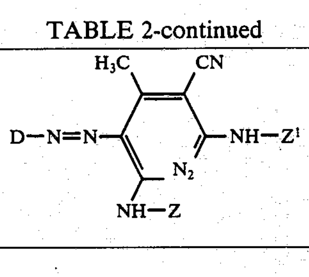

| Ex. | D-NH$_2$ | Z$^1$ | Z$^2$ | Shade |
|---|---|---|---|---|
| 1377 | " | $-H$ | $-(CH_2)_3-O-(C_2H_4O)_3C_6H_5$ | " |
| 1378 | " | $-(CH_2)_3-O-(CH_2-\underset{CH_3}{CH}-O)_2C_4H_9$ | $-CH_2-CH_2-OH$ | " |
| 1379 | " | $-(CH_2)_2-O-C_6H_5$ | " | " |
| 1380 | " | $-(CH_2)_3-O-C_6H_5$ | " | " |
| 1381 | " | $-CH_2-\underset{CH_3}{CH}-O-C_6H_5$ | " | " |
| 1382 | " | $-(CH_2)_3-O-(CH_2)_6-OH$ | " | " |
| 1383 | " | 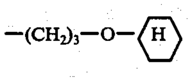 | " | " |
| 1384 | 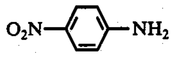 | $-CH_2-\underset{CH_3}{CH}-O-C_6H_5$ | " | orange |
| 1385 | " | $-(CH_2)_3-(O-C_2H_4)_2-OCH_3$ | " | " |
| 1386 | " | $-(CH_2)_3-(OC_2H_4)_3-O-C_2H_5$ | " | " |
| 1387 | " | $-(CH_2)_3-(OC_2H_4)_4-O-C_2H_5$ | " | " |
| 1388 | " | $-(CH_2)_3-(OCHCH_2)_2-O-CH_3$ | " | " |
| 1389 | " | $-H$ | $-(CH_2)_3-(O-C_2H_4)_3OCH_3$ | " |
| 1390 | " | $-H$ | $-(CH_2)_3-(O-\underset{CH_3}{C}HCH_2)_3OCH_3$ | " |
| 1391 | " | $-H$ | $-CH_2-CH-O-C_6H_5$ | " |
| 1392 | " | $-H$ | $-(CH_2)_3-(O-CH_2-CH_2)_2$-$OC_6H_5$ | " |
| 1393 | " | $-H$ | $-(CH_2)_3-(OCH_2\underset{CH_3}{C}H)_2OC_6H_5$ | |
| 1394 | " | $-(CH_2)_3-(O-C_2H_4)_2-OC_6H_5$ | $-CH_2-CH_2-OH$ | " |
| 1395 | " | 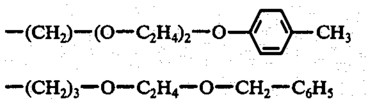 | " | " |
| 1396 | " | $-(CH_2)_3-O-C_2H_4-O-CH_2-C_6H_5$ | " | " |
| 1397 | 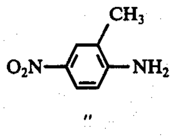 | $-(CH_2)_3-O-C_2H_4-O-CH_2-C_6H_5$ | " | " |
| 1398 | " | $-(CH_2)_3-O-C_2H_4-O-CH(CH_3)_2$ | " | " |
| 1399 | " | $-(CH_2)_3-O-C_2H_4-C_6H_5$ | " | " |
| 1400 | 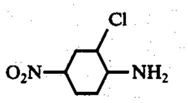 | " | " | yellowish red |
| 1401 | " | " | $-(CH_2)_3-OH$ | " |
| 1402 | " | $-(CH_2)_3-(O-C_2H_4)_2-O-C_6H_5$ | " | " |
| 1403 | " | $-(CH_2)_3-(O-\underset{CH_3}{C}H-CH_2)_2-O-C_6H_5$ | $-CH_2-CH_2-OH$ | " |

TABLE 2-continued

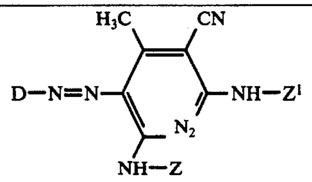

| Ex. | $D-NH_2$ | $Z^1$ | $Z^2$ | Shade |
|---|---|---|---|---|
| 1404 | 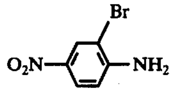 | $-H$ | $-(CH_2)_3-O-CH_2-C_6H_5$ | " |
| 1405 | " | $-H$ | $-(CH_2)_3-O-C_2H_4OC_6H_5$ | " |
| 1406 | " | $-(CH_2)_3-O-CH_2-C_6H_5$ | $-CH_2-CH_2-OH$ | " |
| 1407 | 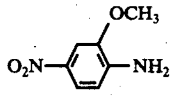 | " | " | " |
| 1408 | " | $-(CH_2)_3-O-CH-CH_2-O-C_6H_5$ | " | " |
| 1409 | 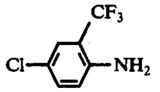 | $-H$ | $-(CH_2)_3-(OCH_2CH_2)_3OC_6H_5$ | yellow |
| 1410 | " | $-(CH_2)_3-O-\underset{CH_3}{\underset{\mid}{CH}}-CH_2-O-C_6H_5$ | $-CH_2-CH_2-OH$ | " |
| 1411 | " | $-(CH_2)_3-O-CH_2-C_6H_5$ | " | " |
| 1412 | 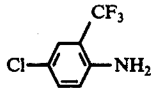 | $-(CH_2)_3-(O-C_2H_4)_3-O-C_6H_5$ | $-CH_2-CH_2-OH$ | " |
| 1413 | " | $-(CH_2)_3-(O-C_2H_4)_4-O-C_2H_5$ | " | " |
| 1414 | " | " | $-(CH_2)_3-OH$ | " |
| 1415 | 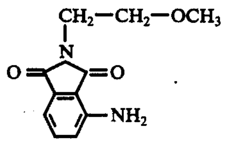 | " | " | " |
| 1416 | " | $-H$ | $-(CH_2)_3-O-CH_2-C_6H_5$ | " |
| 1417 | 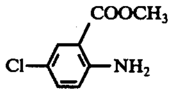 | | " | " |
| 1418 | " | $-(CH_2)_3-O-CH_2-C_6H_5$ | $-CH_2-CH_2-OH$ | " |
| 1419 | 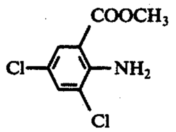 | " | " | orange |
| 1420 | 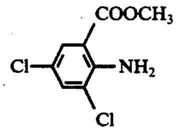 | 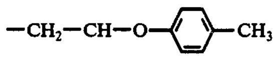 | $-CH_2-CH_2-OH$ | " |
| 1421 | 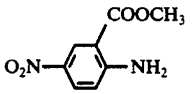 | " | " | red |
| 1422 | " | $-(CH_2)_3-O-(CH_2)_6-OH$ | $-H$ | yellowish red |
| 1423 | " | $-H$ | $-(CH_2)_3-O-(CH_2)_6OH$ | " |
| 1424 | " | $-CH_2-C-O-C_6H_5$ | $-CH_2-CH_2-OH$ | red |

TABLE 2-continued

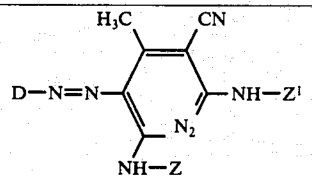

| Ex. | D-$NH_2$ | $Z^1$ | $Z^2$ | Shade |
|---|---|---|---|---|
| 1425 | " | $-CH_2-CH_2-O-C_6H_5$ | " | " |
| 1426 | 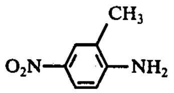 | $-H$ | $-(CH_2)_3-O-(CH_2)_6-OH$ | orange |
| 1427 | " | $-H$ | $-(CH_2)_3-O-(C_2H_4O)_2-C_6H_5$ | " |
| 1428 | " | $-H$ | $-(CH_2)_3-O-CH_2-C_6H_5$ | " |
| 1429 | " | $-(CH_2)_3-O-CH_2-C_6H_5$ | $-H$ | " |
| 1430 | " | $-(CH_2)_3-O-CH_2-C_6H_5$ | " | " |
| 1431 | " | $-(CH_2)_3-OC_2H_4-O-C_2H_5$ | " | " |
| 1432 | " | $-(CH_2)_3-OCH(CH_3)CH_2-O-CH_3$ | " | " |
| 1433 | " | $-(CH_2)_3-(O-CH-CH_2)_2-O-CH_3$ | " | " |
| 1434 | 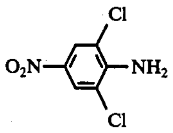 | $-(CH_2)_3-O-(CH_2CH_2O)_2CH_3$ | " | yellowish red |
| 1435 | " | $-(CH_2)_3-O-CH_2-C_6H_5$ | " | " |
| 1436 | 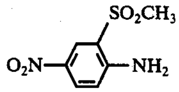 | " | " | red |
| 1437 | " | $-H$ | $-(CH_2)_3-O-CH_2-C_6H_5$ | " |
| 1438 | " | $-(CH_2)_3-O-C_2H_4OC_4H_9$ | $-CH_2-CH_2-OH$ | " |
| 1439 | " | $-(CH_2)_3-O-C_2H_4-O-CH(CH_3)_2$ | " | " |
| 1440 | " | $-(CH_2)_3-O-(CH_2)_2-C_6H_5$ | $-CH_2-CH_2-OH$ | " |
| 1441 | " | $-(CH_2)_3-O-(C_2H_4O)_2-C_6H_5$ | " | " |
| 1442 | 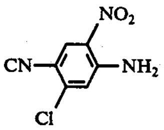 | " | " | " |
| 1443 | " | $-(CH_2)_3-O-CH_2-C_6H_5$ | " | " |
| 1444 | " | " | $-(CH_2)_3-OH$ | " |
| 1445 | " | $-(CH_2)_3-O-(C_2H_4O)_2C_6H_5$ | $-CH_2-CH_2-OH$ | " |
| 1446 | " | $-H$ | $-(CH_2)_3-O-CH_2-C_6H_5$ | " |
| 1447 | 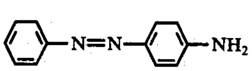 | $-(CH_2)_3-O-(CH_2)_2-OH$ | $-H$ | orange |
| 1448 | " | $-(CH_2)_3-O-CH_2-C_6H_5$ | " | reddish blue |
| 1449 | " | " | $-CH_2-CH_2-OH$ | " |
| 1450 | 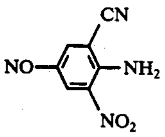 | " | " | violet |

TABLE 3

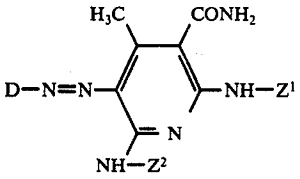

| Ex. | $D-NH_2$ | $Z^1$ | $Z^2$ | Shade |
|---|---|---|---|---|
| 1451 | 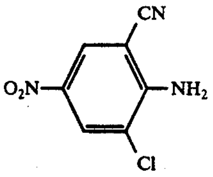 | $-(CH_2)_3-O-CH_2-C_6H_5$ | $-CH_2-CH_2-OH$ | reddish |
| 1452 | 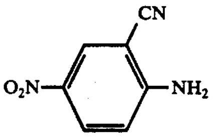 | $-(CH_2)_3-O-CH_2-C_6H_5$ | $-CH_2-CH_2-OH$ | bluish red |
| 1453 | 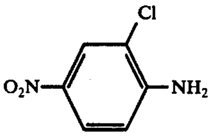 | $-(CH_2)_3-O-CH_2-C_6H_5$ | $-CH_2-CH_2-OH$ | red |

TABLE 4

Coupling component:

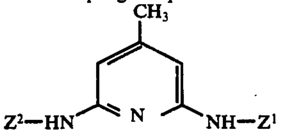

In coupling with these coupling components mixtures are formed because the coupling may take place in the 3-position and also in the 5-position of the pyridine ring:

| No. | Diazo component | $Z^1$ | $Z^2$ | Shade |
|---|---|---|---|---|
| 1454 | 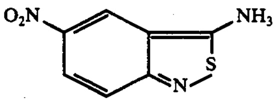 | $-(CH_2)_3-O-CH_2C_6H_5$ | $-CH_2-CH_2-OH$ | greenish blue |
| 1455 | " | " | $-(CH_2)_3-OH$ | " |
| 1456 | " | $-(CH_2)_3-O-C_2H_4-OC_2H_5$ | $-CH_2-CH_2-OH$ | " |
| 1457 | 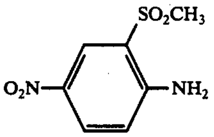 | $-(CH_2)_3-O-CH_2-C_6H_5$ | " | reddish violet |
| 1458 | 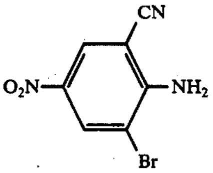 | " | " | " |
| 1459 | " | $-CH_2-CH-O-C_6H_5$<br>$CH_3$ | " | " |
| 1460 | 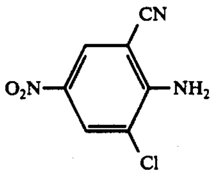 | " | " | " |
| 1461 | " | $-(CH_2)_4-O-CH_2-C_6H_5$ | " | " |

-continued

| No. | Diazo component | $Z^1$ | $Z^2$ | Shade |
|---|---|---|---|---|
| 1462 | 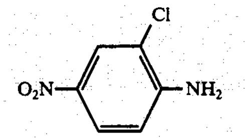 | $-CH_2)_3-O-CH_2-C_6H_5$ | $-(CH_2)_3-OH$ | bluish red |

The dyes set out in Table 5 are also particularly valuable. They are distinguished by high yield and high fastness to dry-heat pleating and setting.

TABLE 5

Coupling component:

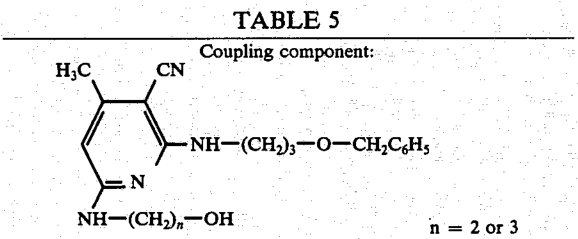

n = 2 or 3

| No. | Diazo component | | Shade |
|---|---|---|---|
| 1463 | 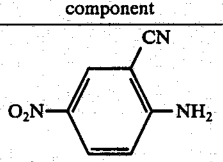 | 2 | red |
| 1464 | " | 3 | " |
| 1465 | 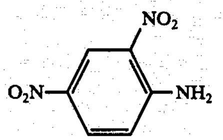 | 2 | bluish red |
| 1466 | " | 3 | " |
| 1467 | 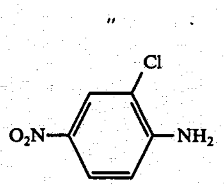 | 2 | yellowish red |
| 1468 | " | 3 | " |
| 1469 | 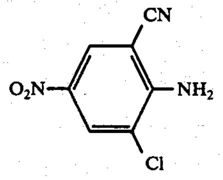 | 2 | bluish red |
| 1470 | " | 3 | " |
| 1471 | 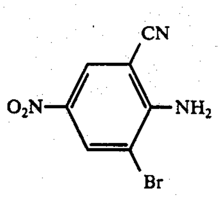 | 2 | " |
| 1472 | " | 3 | " |

TABLE 5-continued

Coupling component:

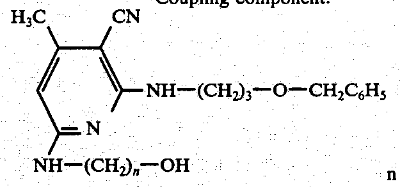

n = 2 or 3

| No. | Diazo component | | Shade |
|---|---|---|---|
| 1473 | 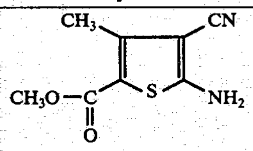 | 2 | " |
| 1484 | " | 3 | " |
| 1475 | 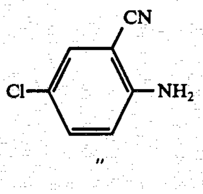 | 2 | yellow |
| 1476 | " | 3 | " |
| 1477 | 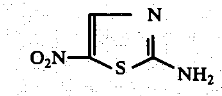 | 2 | reddish violet |
| 1478 | " | 3 | " |
| 1479 | 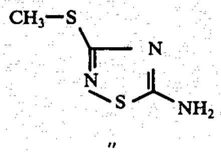 | 2 | orange |
| 1480 | " | 3 | " |
| 1481 | 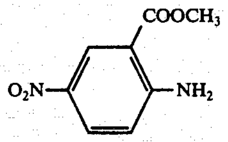 | 2 | red |
| 1482 | " | 3 | " |
| 1483 | 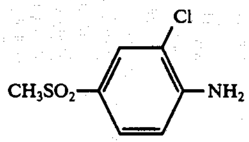 | 2 | orange |
| 1484 | " | 3 | " |

TABLE 6
Coupling component: 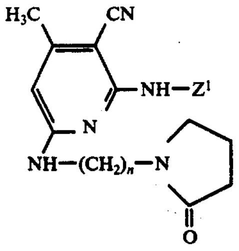
| No. | D-NH$_2$ | n | Z$^1$ | Shade |
|---|---|---|---|---|
| 1485 | 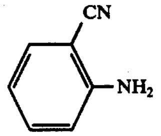 | 2 | $-(CH_2)_3-O-(CH_2)_2OH$ | yellow |
| 1486 | " | 3 | " | " |
| 1487 | " | 6 | " | " |
| 1488 | 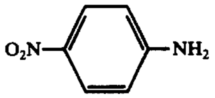 | 2 | " | orange |
| 1489 | " | 6 | " | " |
| 1490 | 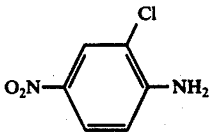 | 2 | " | yellowish red |
| 1491 | " | 3 | " | " |
| 1492 | 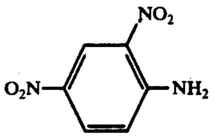 | 2 | " | bluish red |
| 1493 | " | 3 | " | " |
| 1494 | 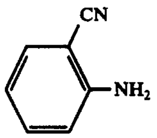 | 2 | $-(CH_2)_3-O-CH_2-C_6H_5$ | yellow |
| 1495 | 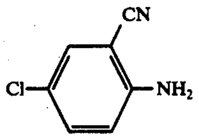 | 2 | " | " |
The dye of the formula:
1496 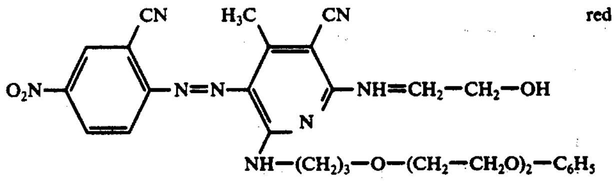 red TABLE 7
Coupling component: 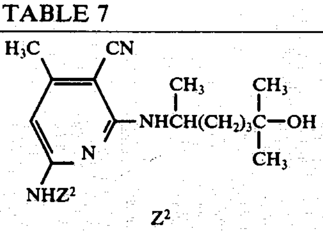
| No. | Diazo component | $Z^2$ | Shade |
|---|---|---|---|
| 1497 | 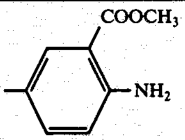 | $C_2H_4OC_2H_4OH$ | yellow |
| 1498 | " | $C_2H_4OC_2H_4OCH_3$ | " |
| 1499 | 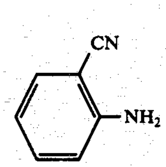 | $CH_2-CH(OH)-C_6H_5$ | " |
| 1500 | " | $C_2H_4OC_2H_4OH$ | " |
| 1501 | 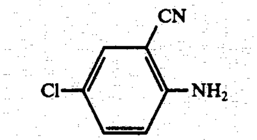 | " | " |
| 1502 | " | $CH_2-CH(OH)-C_6H_5$ | " |
| 1503 | 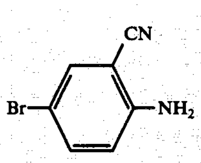 | $C_2H_4OC_2H_4OH$ | " |
| 1504 | 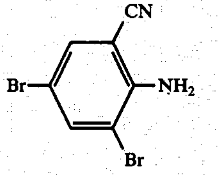 | " | orange |
| 1505 | 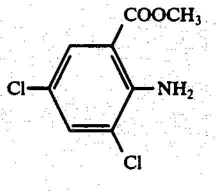 | " | " |
| 1506 | 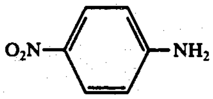 | " | orange |
| 1507 | " | $(CH_2)_3O(CH_2)_6OH$ | " |
| 1508 | 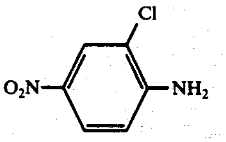 | $C_2H_4OC_2H_4OH$ | yellowish red |
| 1509 | " | $(CH_2)_3(OC_2H_4)_2OCH_3$ | " |

TABLE 7-continued
Coupling component:
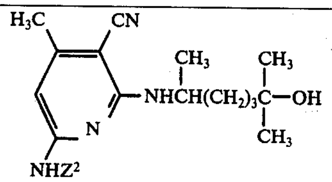
| No. | Diazo component | $Z^2$ | Shade |
|---|---|---|---|
| 1510 | 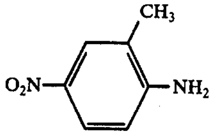 | $C_2H_4OC_2H_4OH$ | " |
| 1511 | 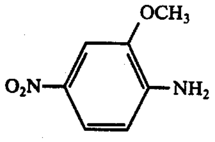 | " | " |
| 1512 | 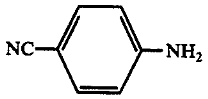 | " | yellow |
| 1513 | 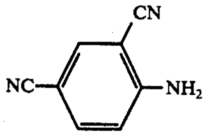 | " | orange |
| 1514 | 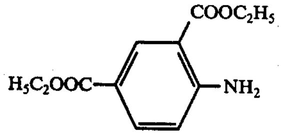 | " | yellow |
| 1515 | 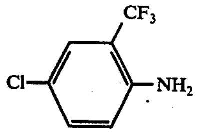 | " | " |
| 1516 | 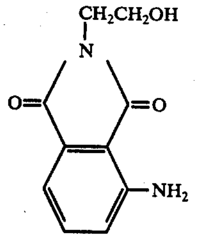 | " | " |
| 1517 | 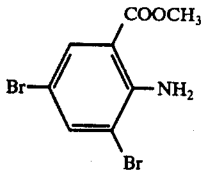 | " | orange |
| 1518 | 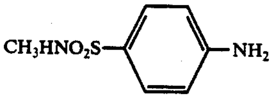 | " | yellow |
| 1519 | 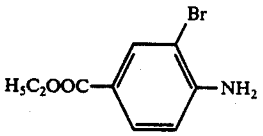 | " | " |

TABLE 7-continued
Coupling component: 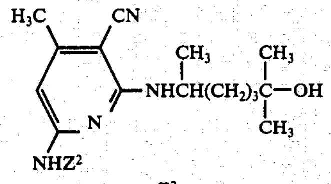
| No. | Diazo component | Z² | Shade |
|---|---|---|---|
| 1520 | 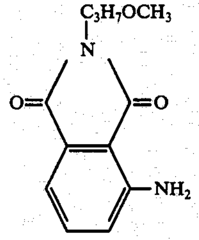 | ″ | ″ |
| 1521 | 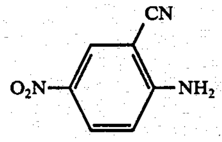 | ″ | yellowish red |
| 1522 | 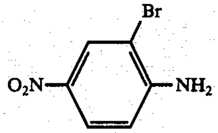 | ″ | ″ |
| 1523 | 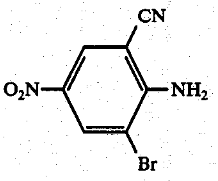 | ″ | red |
| 1524 | 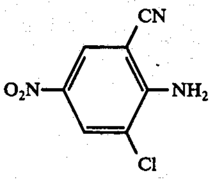 | ″ | ″ |
| 1525 | 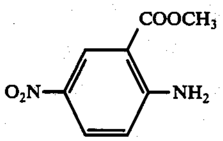 | ″ | ″ |
| 1526 | 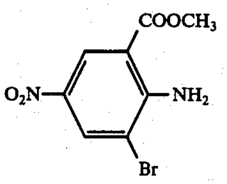 | ″ | ″ |
| 1527 | 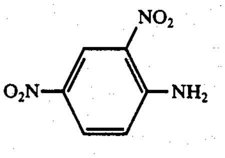 | ″ | ″ |

TABLE 7-continued
Coupling component:
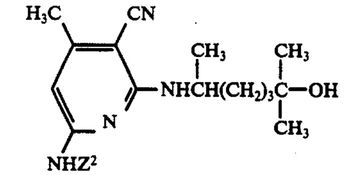
| No. | Diazo component | $Z^2$ | Shade |
|---|---|---|---|
| 1528 | 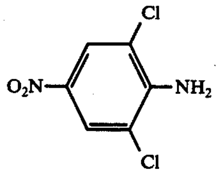 | ″ | yellowish red |
| 1529 | 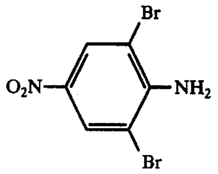 | ″ | ″ |
| 1530 | 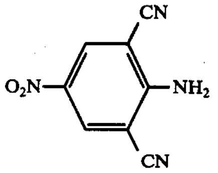 | ″ | bluish red |
| 1531 | 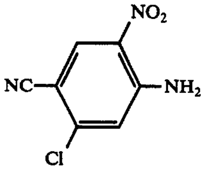 | ″ | red |
| 1532 | 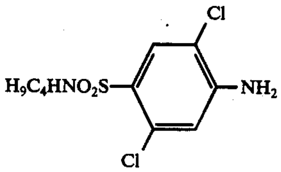 | ″ | yellow |
| 1533 | 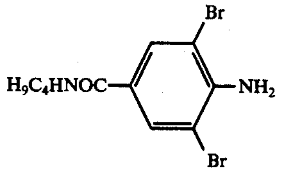 | ″ | ″ |
| 1534 | 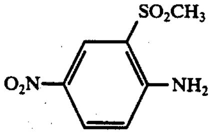 | $(CH_2)_3O(CH_2)_4OH$ | red |
| 1535 | 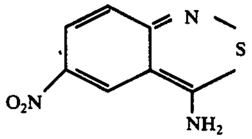 | ″ | reddish blue |
| 1536 | ″ | $C_2H_4OC_2H_4OH$ | ″ |

TABLE 7-continued
Coupling component:
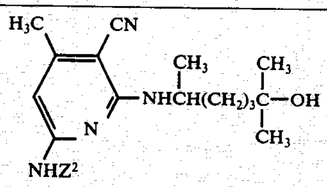
| No. | Diazo component | $Z^2$ | Shade |
|---|---|---|---|
| 1537 | 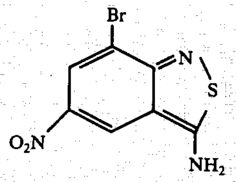 | ″ | ″ |
| 1538 | 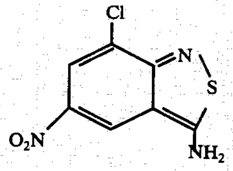 | ″ | ″ |
| 1539 | 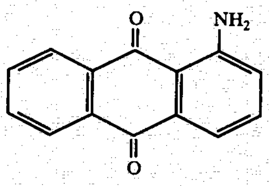 | ″ | yellowish blue |
| 1540 | 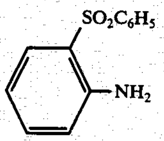 | ″ | yellow |
| 1541 | 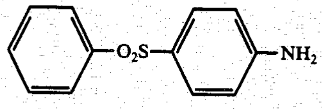 | ″ | ″ |
| 1542 | 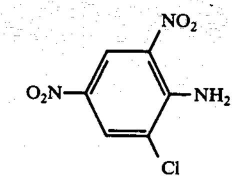 | ″ | bluish red |
| 1543 | 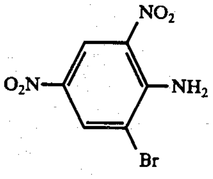 | ″ | ″ |
| 1544 | 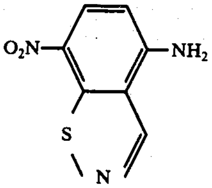 | ″ | ″ |
| 1545 | ″ | $(CH_2)_3O(CH_2)_4OH$ | ″ |

TABLE 7-continued
Coupling component:
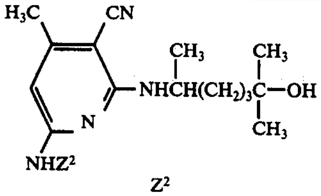
| No. | Diazo component | $Z^2$ | Shade |
|---|---|---|---|
| 1546 | 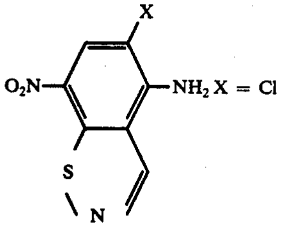 | $C_2H_4OC_2H_4OH$ | violet |
| 1547 | 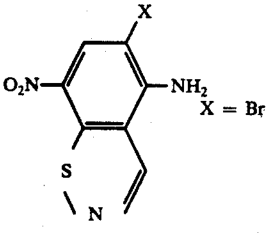 | $C_2H_4OC_2H_4OH$ | violet |
| 1548 | "X = CN | " | bluish violet |
| 1549 | 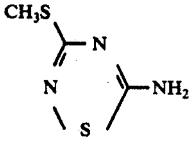 | " | orange |
| 1550 | 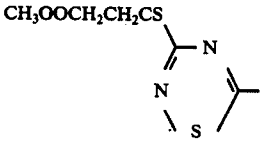 | " | " |
| 1551 | 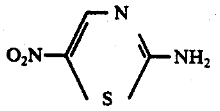 | " | violet |
| 1552 | 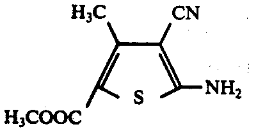 | " | bluish red |
| 1553 | 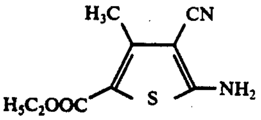 | " | " |
| 1554 | 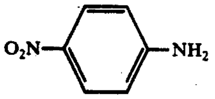 | 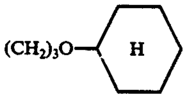 | orange |
| 1555 | " | $(CH_2)_3O(CH_2)_2OH$ | " |
| 1556 | " | 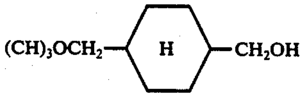 | " |

TABLE 7-continued

Coupling component:

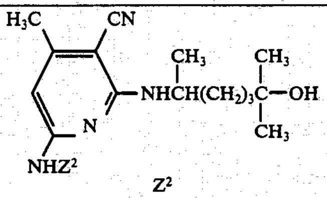

| No. | Diazo component | $Z^2$ | Shade |
|---|---|---|---|
| 1557 | " | $(CH_2)_3OCHCH_2OCH_3$<br>$CH_3$ | " |
| 1558 | " | $(CH_2)_3(OCH-CH_2)_2OCH_3$<br>$C_2$ | " |
| 1559 | " | $(CH_2)_3OC_6H_5$ | " |
| 1560 | " | $(CH_2)_3OCH_2C_6H_5$ | " |
| 1561 | " | $(CH_2)_3OC_2H_4C_6H_5$ | " |
| 1562 | " | $(CH_2)_3OC_2H_4OC_6H_5$ | " |
| 1563 | " | $CH_2CHOHC_6H_5$ | " |

When 2-cyano-4-chloroaniline is used in the case of Examples 1554 to 1563, compounds which give yellow shades are obtained.

TABLE 8

Coupling component:

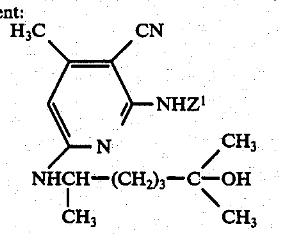

| No. | Diazo component | $Z^1$ | Shade |
|---|---|---|---|
| 1564 | 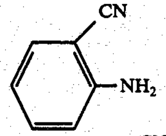 | $(CH_2)_3O(CH_2)_2OH$ | yellow |
| 1565 | 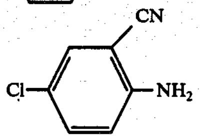 | 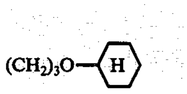 | " |
| 1566 | 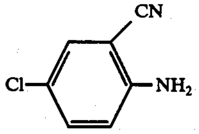 | $C_2H_4OC_2H_4OH$ | " |
| 1567 | 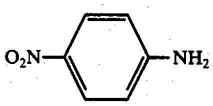 | " | orange |
| 1568 | 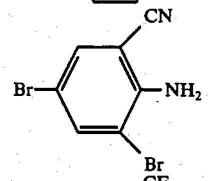 | " | " |
| 1569 | 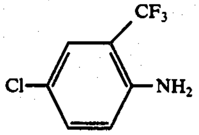 | " | yellow |

TABLE 8-continued

Coupling component:

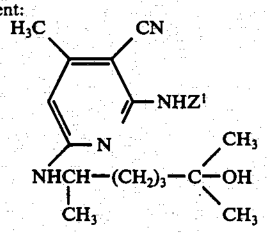

| No. | Diazo component | $Z^1$ | Shade |
|---|---|---|---|
| 1570 | 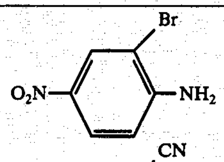 | " | yellowish red |
| 1571 | 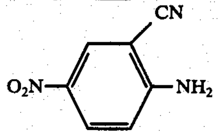 | " | " |
| 1572 | 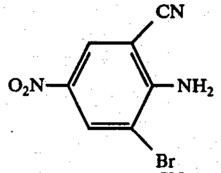 | " | red |
| 1573 | 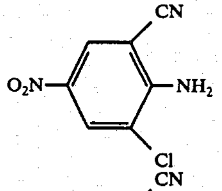 | " | " |
| 1574 | 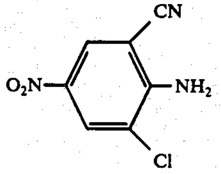 | $(CH_2)_3O(CH_2)_4OH$ | red |

TABLE 8-continued

Coupling component:

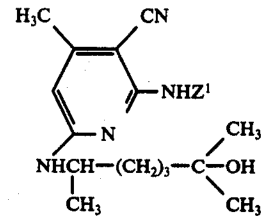

| No. | Diazo component | $Z^1$ | Shade |
|---|---|---|---|
| 1575 | 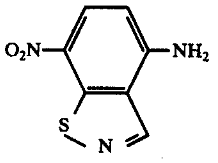 | $C_2H_4OC_2H_4OH$ | " |
| 1576 | 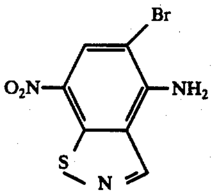 | " | violet |
| 1577 | 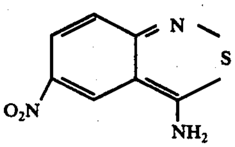 | " | reddish blue |
| 1578 | 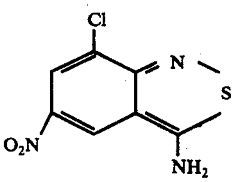 | " | blue |
| 1579 | 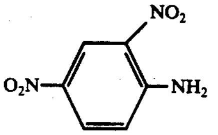 | " | red |
| 1580 | 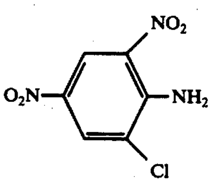 | " | bluish red |
| 1581 | 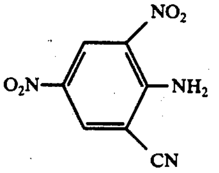 | " | bluish red |
| 1582 | 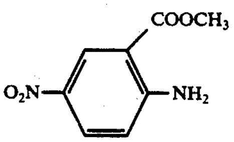 | " | red |

TABLE 9

Coupling component:

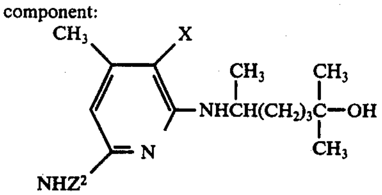

| No. | Diazo component | X | $Z^2$ | Shade |
|---|---|---|---|---|
| 1583 | 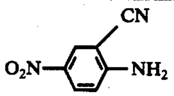 | H | $C_2H_4OC_2H_4OH$ | yellowish red |
| 1584 | 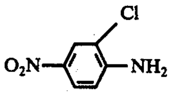 | H | " | " |
| 1585 | 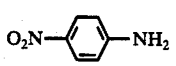 | H | " | orange |
| 1586 | 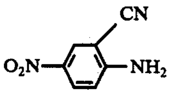 | $CONH_2$ | " | red |
| 1587 | 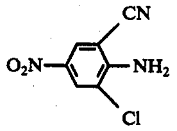 | " | " | reddish violet |

EXAMPLE 1588

A mixture of 187 parts of 2,6-dichloro-3-cyano-4-ethylpyridine, 500 parts of methanol and 135 parts of 2-phenylpropylamine-(1) is stirred for an hour at from about 25° to a maximum of 55° C, then 105 parts of triethylamine is added within fifteen minutes and the whole is stirred for another six hours at about 45° to 55° C. About 250 parts by volume of methanol is distilled off at subatmospheric pressure with the excess triethylamine, the whole is allowed to cool somewhat and the residue is added while stirring to a mixture of about 1500 parts of water, 500 parts of ice and 50 parts of concentrated hydrochloric acid. Stirring is continued for one hour and the precipitate is suction filtered and dried. About 265 parts of a colorless powder is obtained which melts at 85° to 90° C.

27.5 parts of this powder is stirred with about 60 parts of β-hydroxyethylamine for from four to five hours at 130° to 155° C. The whole is allowed to cool and 200 parts by volume of glacial acetic acid and 30 parts by volume of concentrated hydrochloric acid are added to the mixture. A solution of the coupling component of the probable formula:

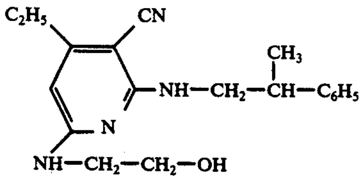

is obtained which contains a minor proportion of the coupling component of the probable formula:

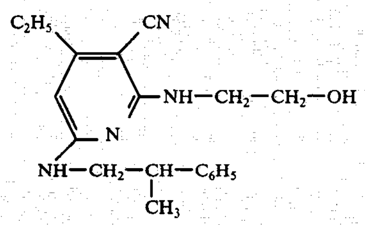

The coupling component mixture has about 50 parts of ice added to it and is cooled to about 0° C. Then there are added in portions at the same time about 100 parts of ice and a solution of diazotized 2-amino-4-nitro-benzonitrile which has been prepared as follows: 16.3 parts of 2-amino-5-nitrobenzonitrile is added while stirring at 0° to 4° C into a mixture of 50 parts of concentrated sulfuric acid and 13 parts of 23% nitrosylsulfuric acid so that the temperature does not at any time rise above 4° C. The whole is stirred for four hours at 0° to 5° C and then coupled as described above. In order to achieve rapid completion of the coupling, which should proceed at about 0° C, the pH of the mixture is adjusted to be from 1.5 to 2.5 by adding sodium acetate. If the mixture should become difficult to stir during the coupling, ice-water may be added.

The mixture is stirred for another hour, heated with steam to 60° to 80° C, suction filtered, washed with water and dried. About 47 parts of a reddish brown powder of the probable formula:

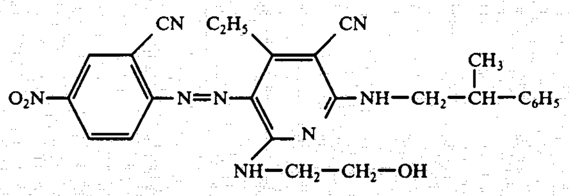

is obtained which contains a smaller dye fraction of the 2,6-alkyl-aminopyridine isomers. It dissolves in dimethylformamide with a red color and dyes polyethylene terephthalate cloth full red shades having excellent fastness properties.

TABLE 1

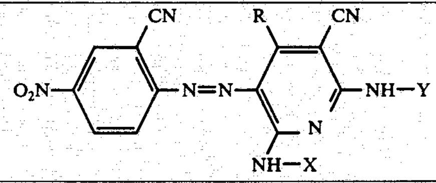

| No. | R | X | Y | Shade |
|---|---|---|---|---|
| 1589 | $-C_2H_5$ | $-CH_2-CH_2-OH$ | $-C_6H_5$ | bluish red |

TABLE 2

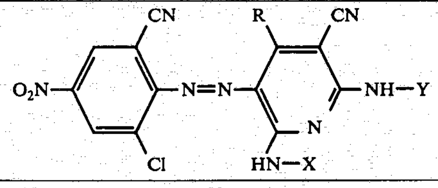

| No. | R | X | Y | Shade |
|---|---|---|---|---|
| 1590 | $-C_3H_7$ | $-CH_2-CH_2-OH$ | $-(CH_2)_3-O-CH_2-C_6H_5$ | red |
| 1591 | $-C_3H_7$ | $-H$ | $-C_6H_5$ | bluish red |

TABLE 3

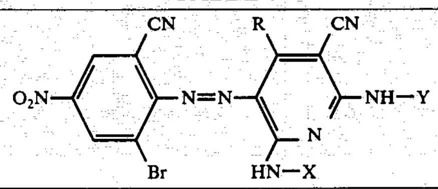

| No. | R | X | Y | Shade |
|---|---|---|---|---|
| 1592 | $-C_3H_7$ | $-CH_2-CH_2-OH$ | $-(CH_2)_3-O-CH_2-C_6H_5$ | red |
| 1593 | $-C_3H_7$ | $-H$ | $-C_6H_5$ | bluish red |

TABLE 4

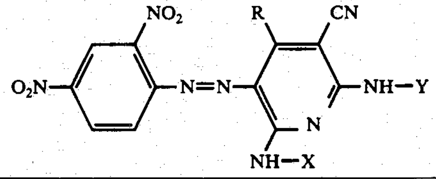

| No. | R | X | Y | Shade |
|---|---|---|---|---|
| 1594 | $-C_3H_7$ | $-CH_2-CH_2-OH$ | $-C_6H_5$ | bluish red |
| 1595 | $-C_3H_7$ | $-CH_2-CH_2-OH$ | $-CH_2-CH(CH_3)-C_6H_5$ | red |

TABLE 5

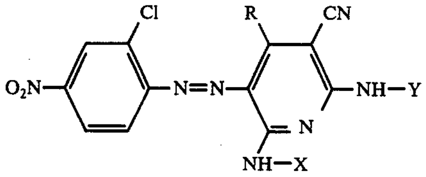

| No. | R | X | Y | Shade |
|---|---|---|---|---|
| 1596 | $-C_2H_5$ | $-CH_2-CH_2-O-CH_2CH_2-OH$ | $-C_6H_5$ | yellowish red |
| 1597 | $-C_2H_5$ | $-CH_2-CH_2-OH$ | $-C_6H_5$ | yellowish red |

TABLE 6

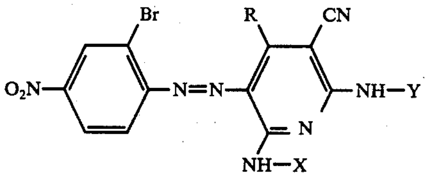

| No. | R | X | Y | Shade |
|---|---|---|---|---|
| 1598 | $-C_2H_5$ | $-CH_2-CH_2-O-CH_2-CH_2-OH$ | $-C_6H_5$ | yellowish red |
| 1599 | $-C_2H_5$ | $-CH_2-CH_2-OH$ | $-C_6H_5$ | yellowish red |

TABLE 7

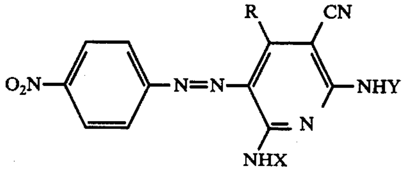

| No. | R | X | Y | Shade |
|---|---|---|---|---|
| 1600 | $-C_3H_7(n)$ | $-CH_2-CH_2-OH$ | $-CH_2-CH(CH_3)-O-C_6H_5$ | reddish orange |
| 1601 | $-C_3H_7(n)$ | $-CH_2-CH_2-OH$ | $-C_6H_5$ | yellowish red |
| 1602 | $-C_2H_5$ | $-CH_2-CH_2-OH$ | $-C_6H_5$ | yellowish red |
| 1603 | $-C_2H_5$ | $-CH_2-CH_2-O-CH_2-OH_2-OH$ | $-C_6H_5$ | yellowish red |

TABLE 8

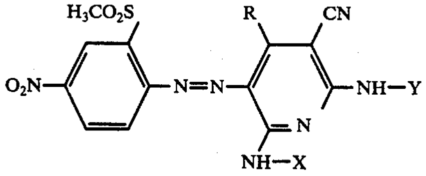

| No. | R | X | Y | Shade |
|---|---|---|---|---|
| 1604 | $-C_2H_5$ | $-CH_2-CH_2-OH$ | $-(CH_2)_3-O-(CH_2)_6-OH$ | red |
| 1605 | $-C_3H_7(n)$ | $-CH_2-CH_2-OH$ | $-CH_2-CH(CH_3)-C_6H_5$ | " |
| 1606 | $-C_2H_5$ | $-CH_2-CH_2-OH$ | $-CH_2-CH(CH_3)-C_6H_5$ | " |
| 1607 | $-C_3H_7(n)$ | $-CH_2-CH_2-OH$ | $-C_6H_5$ | " |
| 1608 | $-C_2H_5$ | $-CH_2-CH_2-OH$ | $-C_6H_5$ | " |
| 1609 | $-C_3H_7(n)$ | $-CH_2-CH_2-OH$ | $-CH_2-CH_2-CH(CH_3)-C_6H_5$ | " |
| 1610 | $-C_3H_7(n)$ | $-CH_2-CH_2-OH$ | $-CH(CH_3)-(CH_2)_3-C(CH_3)_2-OH$ | " |

TABLE 9

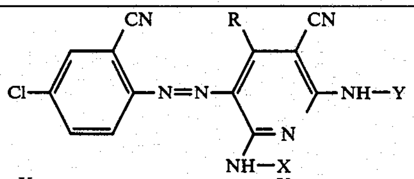

| No. | R | X | Y | Shade |
|---|---|---|---|---|
| 1611 | $-C_2H_5$ | $-CH_2-CH_2-CH_2-OH$ | $-C_6H_5$ | yellow to orange |
| 1612 | $-C_2H_5$ | $-CH_2-CH_2-OH$ | $-C_6H_5$ | " |
| 1613 | $-C_3H_7(n)$ | $-H$ | $-CH_2-CH(CH_3)-C_6H_5$ | yellow |
| 1614 | $-C_3H_7(n)$ | $-CH_2-CH(CH_3)-C_6H_5$ | $-H$ | " |
| 1615 | $-C_3H_7(n)$ | $-CH_2-CH(CH_3)-C_6H_5$ | $-CH_2-CH_2-OH$ | " |

TABLE 10

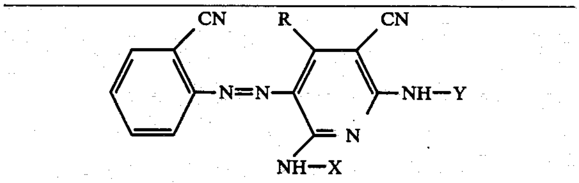

| No. | R | X | Y | Shade |
|---|---|---|---|---|
| 1616 | $-C_3H_7(n)$ | $-CH_2-CH_2-OH$ | $-C_6H_5$ | yellow |
| 1617 | $-C_3H_7(n)$ | $-CH_2-CH_2-CH_2-OH$ | $-C_6H_5$ | " |

TALE 12

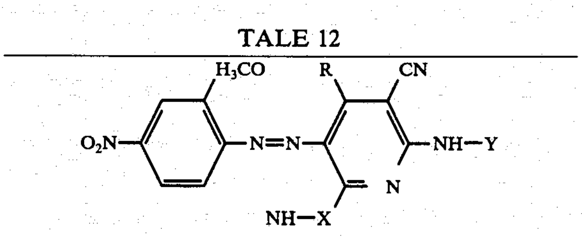

| No. | R | X | Y | Shade |
|---|---|---|---|---|
| 1625 | $-C_2H_5$ | $-CH_2-CH_2-OH$ | $-C_6H_5$ | red |

TABLE 13

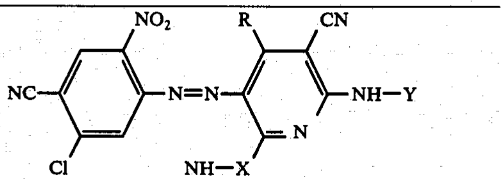

| No. | R | X | Y | Shade |
|---|---|---|---|---|
| 1626 | $-C_2H_5$ | $-CH_2-CH_2-OH$ | $-C_6H_5$ | red |

TABLE 11

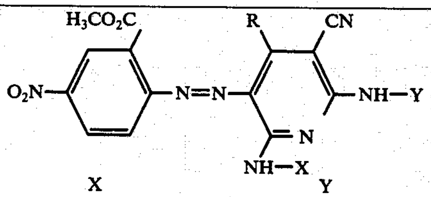

| No. | R | X | Y | Shade |
|---|---|---|---|---|
| 1618 | $-C_2H_5$ | $-H$ | $-(CH_2)_3-O-(CH_2)_6-OH$ | yellowish red |
| 1619 | $-C_3H_7(n)$ | $-CH_2-CH_2-OH$ | $-CH_2-CH(CH_3)-C_6H_5$ | red |
| 1620 | $-C_2H_5$ | $-CH_2-CH_2-OH$ | $-CH_2-CH(CH_3)-C_6H_5$ | " |
| 1621 | $-C_3H_7(n)$ | $-CH_2-CH_2-OH$ | $-C_6H_5$ | " |
| 1622 | $-C_2H_5$ | $-CH_2-CH_2-OH$ | $-C_6H_5$ | " |
| 1623 | $-C_3H_7(n)$ | $-CH_2-CH_2-OH$ | $-CH_2-CH_2-CH(CH_3)-C_6H_5$ | " |
| 1624 | $-C_3H_7(n)$ | $-CH_2-CH_2-OH$ | $-CH(CH_3)-(CH_2)_3-C(CH_3)_2-OH$ | " |

TABLE 14

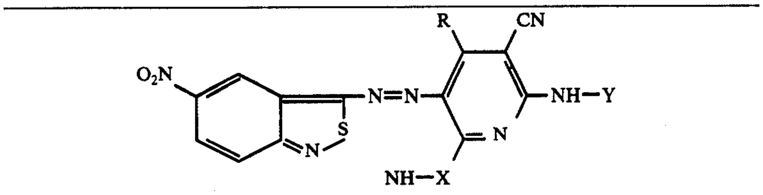

| No. | R | X | Y | Shade |
|---|---|---|---|---|
| 1627 | $-C_2H_5$ | $-CH_2-CH_2-O-CH_2-CH_2-OH$ | $-C_6H_5$ | blue |
| 1628 | $-C_2H_5$ | $-CH_2-CH_2-CH_2-OH$ | $-C_6H_5$ | blue |
| 1629 | $-C_2H_5$ | $-CH_2-CH_2-OH$ | $-C_6H_5$ | blue |
| 1630 | $-C_3H_7(n)$ | $-(CH_2)_3-O-(CH_2)_6-OH$ | $-H$ | violet |

TABLE 15

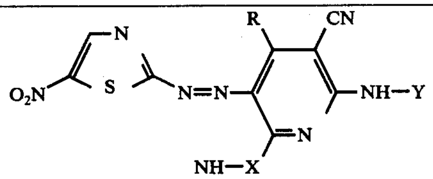

| No. | R | X | Y | Shade |
|---|---|---|---|---|
| 1631 | $-C_3H_7(n)$ | $-CH_2-CH_2-OH$ | $-(CH_2)_3-O-(CH_2)_2-O-(CH_2)_2-OCH_3$ | reddish violet |
| 1632 | $-C_3H_7(n)$ | $-H$ | $-C_6H_5$ | reddish violet |
| 1633 | $-C_3H_7(n)$ | $-CH_2-CH_2-OH$ | $-CH_2-CH(CH_3)-C_6H_5$ | reddish violet |
| 1634 | $-C_3H_7(n)$ | $-(CH_2)_2-O-(CH_2)_2-OH$ | $-CH_2-CH(CH_3)-C_6H_5$ | reddish violet |

TABLE 16

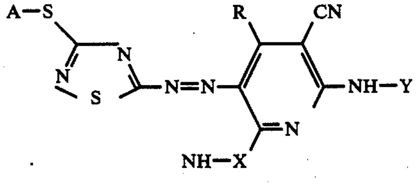

| No. | A | R | X | Y | Shade |
|---|---|---|---|---|---|
| 1635 | O<br>‖<br>$CH_3OC_2H_4-$<br>$CH_2-CH_2-$ | $-C_2H_5$ | $-CH_2-CH_2-OH$ | $-C_6H_5$ | orange |
| 1636 | O<br>‖<br>$CH_3OC_2H_4OC-$<br>$CH_2-CH_2-$ | $-C_3H_7(n)$ | $-CH_2-CH_2-OH$ | $-C_6H_5$ | orange |
| 1637 | O<br>‖<br>$CH_3OC_2H_4OC-$ | $-C_3H_7(n)$ | $-CH_2-CH_2-CH_2OH$ | $-C_6H_5$ | orange |
| 1638 | $CH_3OCOCH_2CH_2-$ | $-C_3H_7(n)$ | $-CH_2-CH_2-OH$ | $-CH_2-CH(CH_3)-C_6H_5$ | orange |

TABLE 17

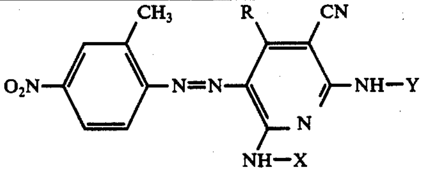

| No. | A | X | Y | Shade |
|---|---|---|---|---|
| 1639 | $-C_3H_7(n)$ | $-CH_2-CH_2-OH$ | $-CH_2-CH(CH_3)-O-C_6H_5$ | reddish orange |
| 1640 | $-C_3H_7(n)$ | $-CH_2-CH_2-OH$ | $-C_6H_5$ | yellowish red |

TABLE 17-continued

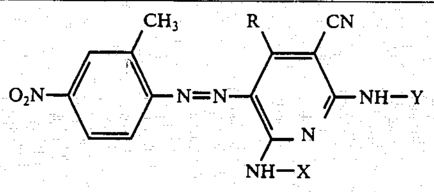

| No. | A | X | Y | Shade |
|---|---|---|---|---|
| 1641 | $-C_2H_5$ | $-CH_2-CH_2-OH$ | $-C_6H_5$ | yellowish red |
| 1642 | $-C_2H_5$ | $-CH_2-CH_2-O-CH_2-CH_2-OH$ | $-C_6H_5$ | yellowish red |

TABLE 18

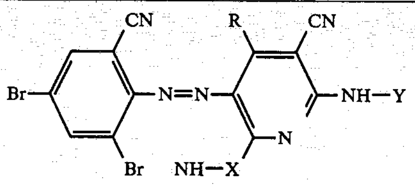

| No. | R | X | Y | Shade |
|---|---|---|---|---|
| 1643 | $-C_3H_7(n)$ | $-CH_2-CH_2-OH$ | $-CH_2-CH-O-C_6H_5$<br>$\quad\quad\quad\; \vert$<br>$\quad\quad\; CH_3$ | orange |
| 1644 | $-C_3H_7(n)$ | $-CH_2-CH_2-OH$ | $-C_6H_5$ | yellowish red |
| 1645 | $-C_2H_5$ | $-CH_2-CH_2-OH$ | $-C_6H_5$ | yellowish red |
| 1646 | $-C_2H_5$ | $-CH_2-CH_2-O-CH_2-CH_2-OH$ | $-C_6H_5$ | yellowish red |

TABLE 19

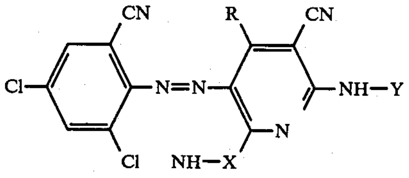

| No. | R | X | Y | Shade |
|---|---|---|---|---|
| 1647 | $-C_3H_7(n)$ | $-CH_2-CH_2-OH$ | $-CH_2-CH-O-C_6H_5$<br>$\quad\quad\quad\; \vert$<br>$\quad\quad\; CH_3$ | orange |
| 1648 | $-C_3H_7(n)$ | $-CH_2-CH_2-OH$ | $-C_6H_5$ | yellowish red |
| 1649 | $-C_2H_5$ | $-CH_2-CH_2-OH$ | $-C_6H_5$ | yellowish red |
| 1650 | $-C_2H_5$ | $-CH_2-CH_2-O-CH_2-CH_2-OH$ | $-C_6H_5$ | yellowish red |

TABLE 20

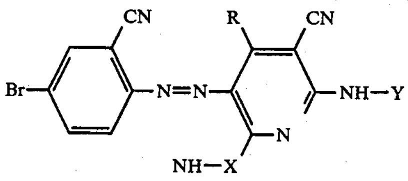

| No. | R | X | Y | Shade |
|---|---|---|---|---|
| 1651 | $-C_3H_6(n)$ | $-CH_2-CH_2-OH$ | $-CH_2-CH-O-C_6H_5$<br>$\quad\quad\quad\; \vert$<br>$\quad\quad\; CH_3$ | yellow |
| 1652 | $-C_3H_7(n)$ | $-CH_2-CH_2-OH$ | $-C_6H_5$ | orange |
| 1653 | $-C_2H_5$ | $-CH_2--CH_2-OH$ | $-C_6H_5$ | orange |
| 1654 | $-C_2H_5$ | $-CH_2-CH_2-O-CH_2-CH_2-OH$ | $-C_6H_5$ | orange |

TABLE 21

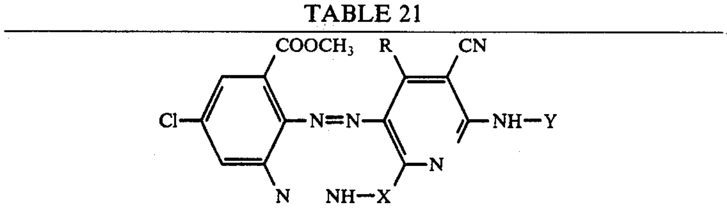

| No. | R | X | Y | Shade |
|---|---|---|---|---|
| 1655 | $-C_2H_5$ | $-CH_2-CH_2-CH_2-OH$ | $-C_6H_5$ | yellow to orange |
| 1656 | $-C_2H_5$ | $-CH_2-CH_2-OH$ | $-C_6H_5$ | yellow to orange |
| 1657 | $-C_3H_7(n)$ | $-H$ | $-CH_2-CH(CH_3)-C_6H_5$ | yellow |
| 1658 | $-C_3H_7(n)$ | $-CH_2-CH(CH_3)-C_6H_5$ | $-H$ | yellow |
| 1659 | $-C_3H_7(n)$ | $-CH_2-CH(CH_3)-C_6H_5$ | $-CH_2-CH_2-OH$ | yellow |

TABLE 22

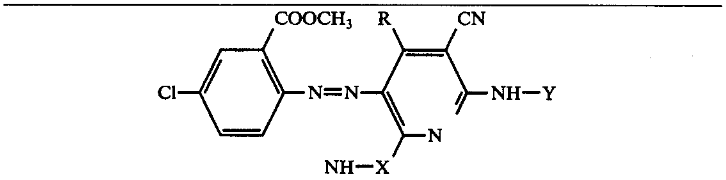

| No. | R | X | Y | Shade |
|---|---|---|---|---|
| 1660 | $-C_2H_5$ | $-CH_2-CH_2-CH_2-OH$ | $-C_6H_5$ | yellow to orange |
| 1661 | $-C_2H_5$ | $-CH_2-CH_2-OH$ | $-C_6H_5$ | yellow to orange |
| 1662 | $-C_3H_7(n)$ | $-H$ | $-CH_2-CH(CH_3)-C_6H_5$ | yellow |
| 1663 | $-C_3H_7(n)$ | $-CH_2-CH(CH_3)-C_6H_5$ | $-H$ | yellow |
| 1664 | $-C_3H_7(n)$ | $-CH_2-CH(CH_3)-C_6H_5$ | $-CH_2-CH_2-OH$ | yellow |

TABLE 23

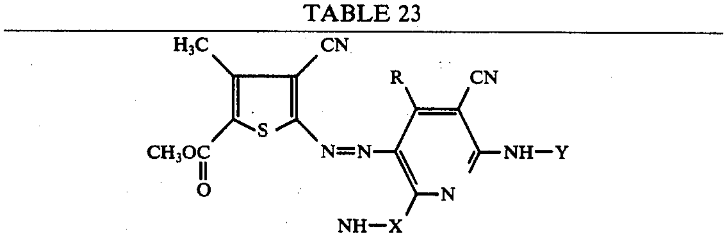

| No. | R | X | Y | Shade |
|---|---|---|---|---|
| 1665 | $-C_3H_7$ | $-CH_2-CH_2-OH$ | $-(CH_2)_3-O-CH_2-C_6H_5$ | bluish red |
| 1666 | $-C_3H_7(n)$ | $-H$ | $-C_6H_5$ | bluish red |

TABLE 24

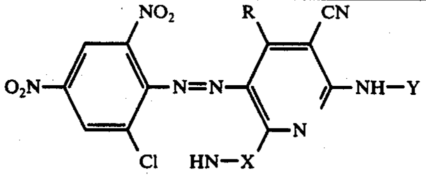

| No. | R | X | Y | Shade |
|---|---|---|---|---|
| 1667 | $-C_3H_7(n)$ | $-CH_2-CH_2-OH$ | $-(CH_2)_3-O-CH_2-C_6H_5$ | bluish red |

TABLE 24-continued

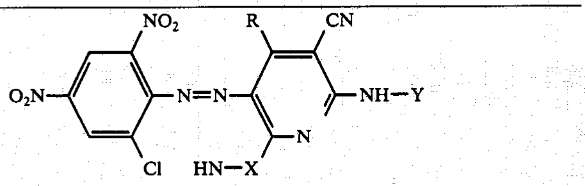

| No. | R | X | Y | Shade |
|---|---|---|---|---|
| 1668 | $-C_3H_7$ | $-H$ | $-C_6H_5$ | bluish red |

TABLE 25

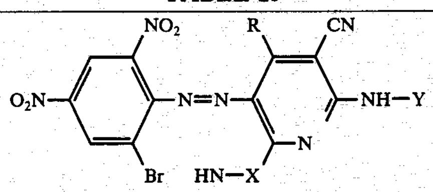

| No. | R | X | Y | Shade |
|---|---|---|---|---|
| 1669 | $-C_3H_7(n)$ | $-CH_2-CH_2-OH$ | $-(CH_2)_3-O-CH_2-C_6H_5$ | bluish red |
| 1670 | $-C_3H_7(n)$ | $-H$ | $-C_6H_5$ | bluish red |

TABLE 26

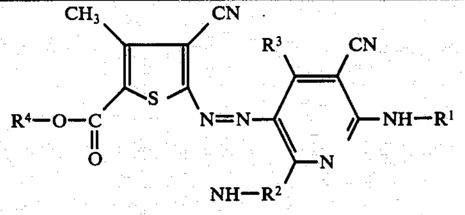

| No. | $R^1$ | $R^2$ | $R^3$ | $R^4$ | Shade |
|---|---|---|---|---|---|
| 1671 | | $(CH_2)_3O(CH_2)_2OH$ | $C_2H_5$ | $CH_3$ | pink |
| 1672 | H | $(CH_2)_3O(CH_2)_6OH$ | $C_3H_7$ | $CH_3$ | pink |
| 1673 | H | $(CH_2)_3O(CH_2)_6OH$ | $CH_3$ | $CH_3$ | pink |
| 1674 | H | $CH(CH_2)_3C-(CH_3)_2$<br>$CH_3$ OH | $CH_3$ | $CH_3$ | pink |
| 1675 | H | $(CH_2)_3O(CH_2)_2OH$ | $CH_3$ | $CH_3$ | pink |
| 1676 | H | $(CH_2)_3O-CH_2C_6H_5$ | $CH_3$ | $CH_3$ | pink |
| 1677 | H | $(CH_2)_3OCH_2CH_2OCH_2$<br>$C_6H_5$ | $CH_3$ | $CH_3$ | pink |
| 1678 | $(CH_2)_3OCH_2C_6H_5$ | $CH_2CH_2OH$ | $C_2H_5$ | $CH_3$ | bluish red |
| 1679 | $(CH_2)_3OCH_2C_6H_5$ | $(CH_2)_3OH$ | $C_2H_5$ | $CH_3$ | bluish red |
| 1680 | $(CH_2)_3OCH_2C_6H_5$ | $(CH_2)_3OH$ | $CH_3$ | $CH_3$ | bluish red |
| 1681 | $(CH_2)_3OCH_2C_6H_5$ | $CH_2CH_2OH$ | $CH_3$ | $CH_3$ | bluish red |
| 1682 | $(CH_2)_3OCH_2C_6H_5$ | $CH_2CH_2OH$ | $CH_3$ | $C_2H_5$ | bluish red |
| 1683 | $(CH_2)_3OCH_2C_6H_5$ | $(CH_2)_3OH$ | $CH_3$ | $C_2H_5$ | bluish red |
| 1684 | $CH_3$<br>$(CH_2)_3OCH_2CH0C_6H_5$ | $(CH_2)_3OH$ | $CH_3$ | $C_2H_5$ | bluish red |
| 1685 | $CH_3$<br>$(CH_2)_3OCH_2CHOC_6H_5$ | $CH_2CH_2OH$ | $CH_3$ | $C_2H_5$ | bluish red |
| 1686 | $CH_3$<br>$(CH_2)_3OCH_2CHOC_6H_5$ | $CH_2CH_2OH$ | $CH_3$ | $CH_3$ | bluish red |
| 1687 | $CH_3$<br>$(CH_2)_3OCH_2CHOC_6H_5$ | $(CH_2)_3OH$ | $C_2H_5$ | $CH_3$ | bluish red |

We claim:

1. A dye of the formula

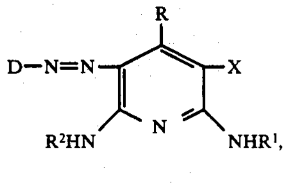

wherein:

D is phenyl substituted by chlorine, bromine, trifluoromethyl, methyl, methoxy, nitro, cyano, methylsulfonyl, phenylsulfonyl, carbalkoxy of a total of 2 to 5 carbon atoms, carbo-β-alkoxy-ethoxy, said alkoxy having 1 to 4 carbon atoms, or N,N-dialkyl- or N-monoalkyl-substituted sulfamoyl, each alkyl having 1 to 4 carbon atoms; phenylazophenyl;

phenylazophenyl substituted by methyl, chlorine, bromine or nitro; benzthiazolyl; benzthiazolyl substituted by nitro, cyano, methylsulfonyl or ethylsulfonyl; benzisothiazolyl substituted by chlorine, bromine, cyano or nitro; thiazolyl substituted by cyano or nitro; thienyl substituted by methyl, cyano, nitro or carbalkoxy of a total of 2 to 5 carbon atoms; or thiadiazolyl substituted by phenyl, methyl, chlorine, bromine, methylmercapto, ethylmercapto or alkoxycarbonylethylmercapto, said alkoxy having 1 to 4 carbon atoms;

R is alkyl of 1 to 3 carbon atoms;

X is carbamoyl or cyano;

$R^1$ and $R^2$ may be the same or different with the proviso that one of $R^1$ and $R^2$ is $C_6H_5$;

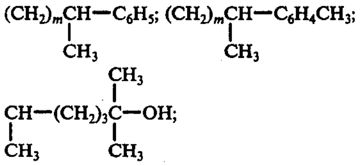

$(CH_2)_3OCH_2CH_2OH$; $(CH_2)_3O(CH_2)_6OH$;

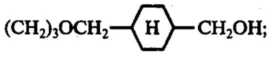

$(CH_2)_3OC_2H_4OR^7$, $(CH_2)_3(OC_2H_4)_qOR^8$, $(CH_2)_3OR^9$;

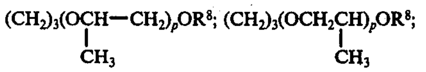

$C_2H_4OC_6H_5$, $C_2H_4OC_6H_4CH_3$;

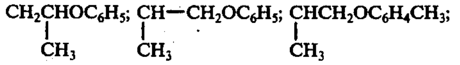

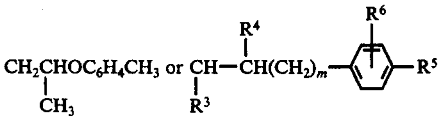

and the other of $R^1$ and $R^2$ is hydrogen;

alkyl of 1 to 8 carbon atoms; alkyl of 2 to 8 carbon atoms substituted by hydroxy, alkoxy of 1 to 8 carbon atoms, formyloxy, acetoxy, propionyloxy, carboxy, cyclohexoxy, benzyloxy, phenylethoxy, phenoxy or pyrrolidonyl; cyclohexyl; methylcyclohexyl; benzyl; phenylethyl; β-phenyl-β-hydroxyethyl; phenyl; tolyl; $CH_2CH_2OCH_2CH_2OH$; $(CH_2)_3OC_6H_5—CH_3$; $(CH_2)_3O(CH_2)_4OH$;

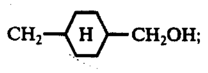

$(CH_2)_3OC_2H_4OCH_3$; $(CH_2)_3OC_2H_4OC_6H_5$;

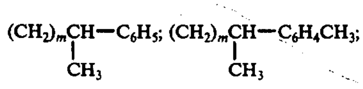

$(CH_2)_3OCH_2CH_2OH$; $(CH_2)_3O(CH_2)_6OH$;

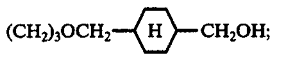

$(CH_2)_3OC_2H_4OR^7$; $(CH_2)_3(oc_2H_4)_qOR^8$;

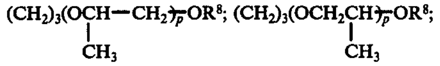

$C_2H_4OC_6H_4CH_3$;

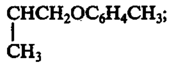

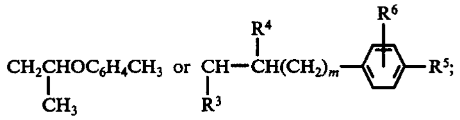

$R^3$ is alkyl of one to three carbon atoms, hydroxymethyl or hydroxyethyl;

$R^4$ is hydrogen, alkyl of one to three carbon atoms, hydroxymethyl or hydroxyethyl;

$R^5$ is hydrogen or hydroxyl;

$R^6$ is hydrogen, alkyl of 1 to 4 carbon atoms, methoxy, ethoxy or chloro; one of $R^3$ to $R^5$ providing a hydroxy group;

$R^7$ is ethyl, propyl, butyl, cyclohexyl, benzyl, phenylethyl or methylphenyl;

$R^8$ is hydrogen, alkyl of one to four carbon atoms, cyclohexyl, phenyl, methylphenyl, benzyl or phenylethyl;

$R^9$ is cyclohexyl, phenyl, methylphenyl, benzyl or phenylethyl;

*m* is 1 or 2;

*n* is zero, 1 or 2;

*q* is 2, 3 or 4; and

*p* is 1, 2, 3 or 4.

2. A dye as claimed in claim 1 of the formula

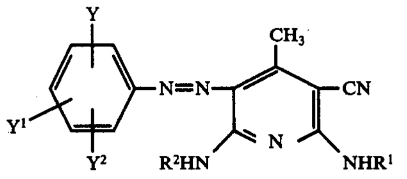

wherein:

Y is nitro, cyano, chloro, bromo, carbomethoxy, carboethoxy, β-methoxycarboethoxy, methylsulfonyl, ethylsulfonyl, methyl, methoxy or phenylazo;

$Y^1$ is hydrogen, nitro, chloro, bromo, cyano, methyl, methoxy, carbomethoxy, carboethoxy, methylsulfonyl or ethylsulfonyl; and $Y^2$ is hydrogen, chloro, bromo, cyano, methyl, methoxy, carbomethoxy or carboethoxy; and $R^1$ and $R^2$ have the same meanings as given in claim 1.

3. A dye as claimed in claim 1 wherein X is cyano.

4. A dye as claimed in claim 1 wherein:

X is cyano;

said one of $R^1$ and $R^2$ is $C_6H_5$;

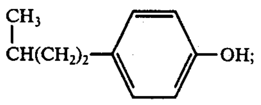
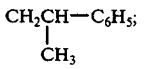
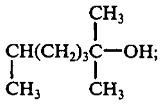
$(CH_2)_3OC_2H_4OH$, $(CH_2)_3O(CH_2)_6OH$,
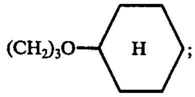
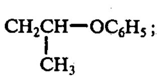
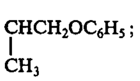
$(CH_2)_3OC_2H_4OCH_2C_6H_5$; $(CH_2)_3(OC_2H_4)_2OR^8$;
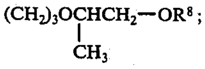
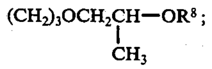
$(CH_2)_3OC_6H_5$; $(CH_2)_3OCH_2C_6H_5$ or $(CH_2)_3OC_2H_4C_6H_5$; and said other of $R^1$ and $R^2$ is hydrogen; or alkyl of 2 to 8 carbon atoms substituted by hydroxy, alkoxy of 1 to 4 carbon atoms, formyloxy, acetoxy or propionyloxy.
5. The dye of the formula
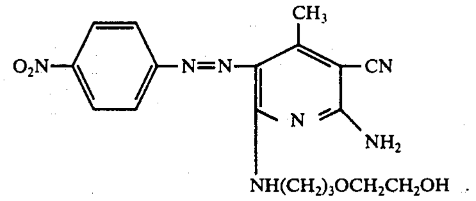
6. The dye of the formula
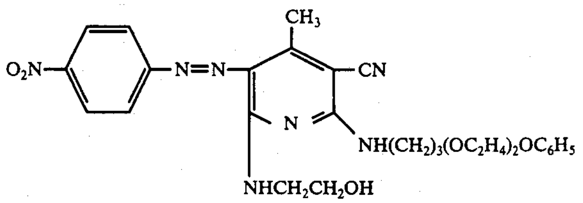
7. The dye of the formula
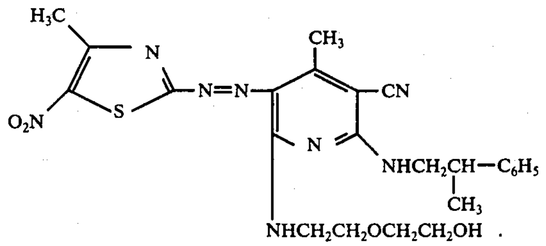
8. The dye of the formula
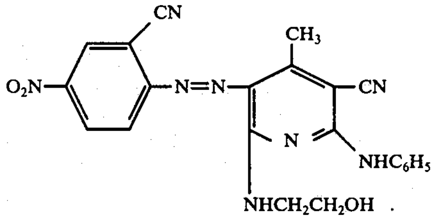
* * * * *